United States Patent [19]
Boger

[11] Patent Number: 5,985,908
[45] Date of Patent: Nov. 16, 1999

[54] MCBI ANALOGS OF CC-1065 AND THE DUOCARMYCINS

[75] Inventor: Dale L. Boger, La Jolla, Calif.

[73] Assignee: The Scripps Research Institute, La Jolla, Calif.

[21] Appl. No.: 09/142,337

[22] PCT Filed: Mar. 7, 1997

[86] PCT No.: PCT/US97/03641

§ 371 Date: Sep. 4, 1998

§ 102(e) Date: Sep. 4, 1998

[87] PCT Pub. No.: WO97/32850

PCT Pub. Date: Sep. 12, 1997

Related U.S. Application Data

[60] Provisional application No. 60/013,024, Mar. 8, 1996.

[51] Int. Cl.⁶ .......................... C07D 403/14; A61K 31/40

[52] U.S. Cl. .......................... 514/410; 514/411; 548/425; 548/427

[58] Field of Search .................................. 548/425, 427; 514/410, 411

[56] References Cited

PUBLICATIONS

Boger, J Org Chem 61(5) 1710, May 1996.

*Primary Examiner*—Robert Gerstl
*Attorney, Agent, or Firm*—Donald G. Lewis

[57] ABSTRACT

MCBI (7-methoxy-1,2,9a-tetra-hydrocyclopropa[c]benz[e] indol-4-one) is employable as a DNA alkylating agent and can be incorporated into analogs of CC-1065 and the duocarmycins for constructing regioselective DNA alkylating agents.

11 Claims, 20 Drawing Sheets

| | k (s⁻¹, pH 3) | $t_{1/2}$ | IC$_{50}$(L1210) |
|---|---|---|---|
| 5 | 1.1 x 10⁻⁶ | 177 h | 6 nM |
| 4 | 1.5 x 10⁻⁶ | 133 h | 80 nM |
| 6 | 5.3 x 10⁻⁶ | 37 h | 330 nM |
| 7 | 1.7 x 10⁻⁵ | 11 h | 1000 nM |
| 8 | 9.1 x 10⁻⁵ | 2 h | 4000 nM |
| 9 | 2.0 x 10⁻² | 0.01 h | 18000 nM |

| Agent | $k$ (s$^{-1}$, pH 3)[a] | $t_{1/2}$(h, pH 3)[a] | IC$_{50}$(μM, L1210) | UV, $\lambda_{max}$ nm (ε) | IR (C=O, cm$^{-1}$) |
|---|---|---|---|---|---|
| 5 | 1.08 x 10$^{-6}$ | 177 | 0.006 | 339 (18000)[b]<br>301 (14000)<br>255 (10000) | 1719, 1610[c] |
| 4 | 1.45 x 10$^{-6}$ | 133[g] | 0.08 | 300 (19000)[d]<br>264 (5700) | 1718, 1628<br>1602[e] |
| 2 3 8 | 1.75 x 10$^{-6}$ | 110[h] | 0.09 | 301 (25000)[d]<br>270 (20000)<br>312 (18000)[b]<br>275 (16000) | 1724, 1622<br>1599[e] |
| 6 | 5.26 x 10$^{-6}$ | 37 | 0.3 | 344 (12000)[b]<br>278 (17000) | 1725, 1570[f] |
| 7 | 1.75 x 10$^{-5}$ | 11 | 1 | nd | nd |
| 8 | 9.07 X 10$^{-5}$ | 2.1 | 2 | 314 (19000)[b]<br>260 (9000)<br>218 (17000) | 1705, 1639<br>1604[c] |
| 9 | 1.98 x 10$^{-2}$ | 0.01 | 18 | 294 (14000)[d]<br>258 (21000) | 1705, 1617[c] |

FIG. 8

| Agent | IC$_{50}$(L1210) | Agent | IC$_{50}$(L1210) |
|---|---|---|---|
| Natural Enantiomers | | | |
| 238 (+)-N-BOC-MCBI | 90 nM | (+)-N-BOC-CBI | 80 nM |
| 254 (+)-MCBI-TMI | 12 pM | (+)-CBI-TMI | 30 pM |
| 258 (+)-MCBI-indole$_2$ | 10 pM | (+)-CBI-indole$_2$ | 10 pM |
| 262 (+)-MCBI-CDPI$_1$ | 6 pM | (+)-CBI-CDPI$_1$ | 5 pM |
| 266 (+)-MCBI-CDPI$_2$ | 6 pM | (+)-CBI-CDPI$_2$ | 5 pM |
| Unnatural Enantiomers | | | |
| 238 (−)-N-BOC-MCBI | 200 nM | (−)-N-BOC-CBI | 900 nm |
| 254 (−)-MCBI-TMI | 400 pM | (−)-CBI-TMI | 2000 pM |
| 258 (−)-MCBI-indole$_2$ | 30 pM | (−)-CBI-indole$_2$ | 4000 pM |
| 262 (−)-MCBI-CDPI$_1$ | 10 pM | (−)-CBI-CDPI$_1$ | 380 pM |
| 266 (−)-MCBI-CDPI$_2$ | 10 pM | (−)-CBI-CDPI$_2$ | 40 pM |

FIG. 10

| Agent | Rel IC$_{50}$ (L1210)[a] | Rel DNA Alkylation Intensity[b] |
|---|---|---|
| CI-TMI | 1 | 0.5-2.0 |
| duocarmycin SA | 10 | 10 |
| MCBI-TMI | 50 | 50 |
| CBI-TMI | 100 | 100 |
| duocarmycin A | >100 | >100 |

FIG. 12

MCBI ANALOGS OF CC-1065 AND THE DUOCARMYCINS

This application claims benefit of Provisional Application 60/013,024 Mar. 8, 1996.

This invention was made with government support under Contract Nos. CA 41986 and CA 55276 by the National Institutes of Health. The government has certain rights in the invention.

FIELD OF INVENTION

The invention relates to antitumor antibiotics. More particularly, the invention relates to analogs of CC-1065 and the duocarmycins having antitumor antibiotic activity.

BACKGROUND (+)-CC-1065 (1) and the duocarmycins represent the initial members of a class of exceptionally potent antitumor antibiotics that derive their biological effects through the reversible, stereoelectronically-controlled sequences alkylation of DNA (Boger et al. *J. Org. Chem.* 1990, 55, 4499; Boger et al. *J. Am. Chem. Soc.* 1990, 112, 8961; Boger et al. *J. Am. Chem. Soc.* 1991, 113, 6645; Boger et al. *J. Am. Chem. Soc.* 1993, 115, 9872; Boger et al. *Bioorg. Med. Chem. Lett.* 1992, 2, 759). Subsequent to their initial disclosure, extensive efforts have been devoted to establish their DNA alkylation selectivity and its structural origin. Efforts have also been devoted to establish the link between DNA alkylation and the ensuing biological properties, i.e., to define the fundamental principles underlying the relationships between structure, chemical reactivity, and biological properties (FIG. 1; 1–3).

CBI (1,2,9,9a-tetrahydrocyclopropa[c]benz[e]indol-4-one) has been identified as an alkylation subunit which corresponds to the alkylation subunit of CC-1065 and the duocarmycins. (Boger et al. *J. Am. Chem. Soc.* 1989, 111, 6461; Boger D. L.; Ishizaki et al. *J. Org. Chem.* 1990, 55, 5823). Agents which include the CBI-based analogs have proven especially useful as DNA alkylating agents. This was significant since preceding studies had attributed such unique characteristics to the naturally occurring alkylation subunits that they left the perception that even small structural perturbations, let alone deep-seated structural changes, would have detrimental effects on the properties. (Hurley et al. *Science* 1984, 226, 843; Reynolds et al. *Biochemistry* 1985, 24, 6228; Hurley et al. *Biochemistry* 1988, 27, 3886; Hurley et al. *J. Am. Chem. Soc.* 1990, 112, 4633; Warpehoski et al. *Biochemistry* 1992, 31, 2502.) Not only has this proven inaccurate, but the natural enantiomers of the CBI-based analogs of (+)-CC-1065 have proven chemically more stable (4×), biological more potent and considerably more synthetically accessible than the corresponding agents incorporating the natural CPI alkylation subunit of CC-1065. (Boger et al. *J. Org. Chem.* 1990, 55, 5823; Boger et al. *J. Org. Chem.* 1992, 57, 2873; Boger et al. *J. Org. Chem.* 1995, 60, 1271.) Moreover, selected agents within the series of CBI analogs not only exhibited potent cytotoxic activity but also potent and efficacious in vivo antitumor activity. (Boger et al. *Bioorg. Med. Chem. Lett.* 1991, 1, 115).

The natural enantiomers of the CBI-based analogs have been shown to alkylate DNA with an unaltered sequence selectivity at an enhanced rate and with a greater efficiency than the corresponding CPI analog. (Boger et al. *Bioorg. Med. Chem. Lett.* 1991, 1, 115; Boger et al. *J. Am. Chem. Soc.* 1991, 113, 2779; Boger et al. *J. Am. Chem. Soc.* 1992, 114, 5487.) This indicates that the simplified CBI alkylation subunit offers important advantages over the natural alkylation subunit of CC-1065. In recent studies, models of the DNA alkylation reactions of CC-1065 and the duocarmycins have been developed. (Boger et al. *J. Org. Chem.* 1990, 55, 4499; Boger et al. *J. Am. Chem. Soc.* 1990, 112, 8961; Boger et al. *J. Am. Chem. Soc.* 1991, 113, 6645; Boger et al. *J. Am. Chem. Soc.* 1993, 115, 9872; Boger et al. *Bioorg. Med. Chem. Lett.* 1992, 2, 759; Boger et al. *J. Am. Chem. Soc.* 1994, 116, 1635. ) These models accomodate the reversed and offset AT-rich adenine $N_3$DNA alkylation selectivity of the enantiomeric agents and their structural analogs. The diastereomeric adducts derived from the unnatural enantiomers have been found to suffer a significant destabilizing steric interaction between the CPI C7 center ($CH_3$) or the CBI C8 center with the base adjacent to the alkylated adenine which is not present with the natural enantiomer adducts. Consistent with this observation, the distinguishing features between the natural and unnatural enantiomers diminish or disappear as the inherent steric bulk surrounding this center is reduced or removed. (Boger et al. *J. Am. Chem. Soc.* 1994, 116, 7996.) Because of the unnatural enantiomer sensitivity to destabilizing steric interactions surrounding the CPI C7 or CBI C8 center, the unnatural enantiomers of the CBI-based analogs are more effective than the corresponding CPI analog displaying an even more enhanced relative rate and efficiency of DNA alkylation.

There is a direct relationship between functional stability and cytotoxic potency. (Boger et al. *J. Am. Chem. Soc.* 1994, 116, 6461; Boger et al. *J. Am. Chem. Soc.* 1994, 116, 11335; Mohamadi et al. *J. Med. Chem.* 1994, 37, 232; Boger et al. *J. Org. Chem.* 1994, 59, 4943; Boger et al. *J. Am. Chem. Soc.* 1989, 111, 6461; Boger et al. *J. Org. Chem.* 1990, 55, 5823). In an ongoing series of studies conducted with agents containing deep-seated modifications in the alkylation subunit which to date include 4–9 (FIG. 2), the agents possessing the greatest solvolysis stability have been found to exhibit the most potent cytotoxic activity. Moreover, this direct relationship between functional stability and biological potency has been observed with both simple and advanced analogs of the natural products. A subsequent validation of this relationship was observed with a series of simple $N^2$ substituted CBI derivatives. (Boger et al. *J. Am. Chem. Soc.* 1994, 116, 5523.) Predictable linear relationships between solvolysis stability (–log k), cytotoxic potency (log $1/IC_{50}$, L1210) and the electron-withdrawing properties of the $N^2$ substituent (Hammett $\sigma_p$ constant) were observed (FIG 2; 4–9).

What is needed is an alternative alkylating agent having an altered reactivity as compared to CBI which may be incorporated into analogs of CC-10665 and the duocarjycins.

SUMMARY OF THE INVENTION

One aspect of the invention is directed to alkylating agents represented by either of the following structures:

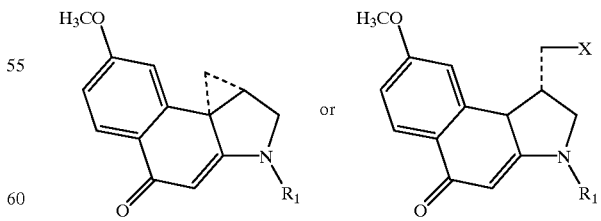

In the above structures, X is selected from the group consisting of chlorine, bromine, iodine, and OTOS and $R_1$ is selected from the group consisting of hydrogen, tert-butoxycarbonyl and a radical represented by the following structure:

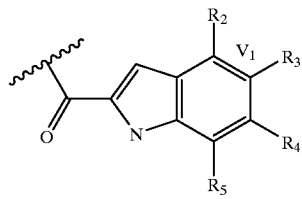

In the above radical, $R_2$ is selected from the group consisting of hydrogen, hydroxyl, O-alkyl (C1–C6), and a first N-substituted pyrrolidine ring; $R_3$ is selected from the group consisting of hydrogen, hydroxyl, O-alkyl (C1–C6), the first N-substituted pyrrolidine ring and a radical represented by the following structure:

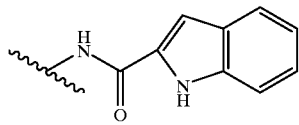

$R_4$ is selected from the group consisting of hydrogen, hydroxyl and O-alkyl (C1–C6); and $R_5$ is selected from the group consisting of hydrogen, hydroxyl and O-alkyl (C1–C6). $V_1$ represents a first vinylene group between $R_2$ and $R_3$. However, the following provisos pertain:

1. If $R_2$ participates in the first N-substituted pyrrolidine ring, then $R_3$ also participates in the first N-substituted pyrrolidine ring;
2. If $R_3$ participates in the first N-substituted pyrrolidine ring, then $R_2$ also participates in the first N-substituted pyrrolidine ring;
3. If $R_2$ and $R_3$ participate in the first N-substituted pyrrolidine ring, then $R_4$ and $R_5$ are hydrogen; and
4. If $R_2$ is hydrogen, then $R_4$ and $R_5$ are hydrogen and $R_3$ is a radical represented by the following structure:

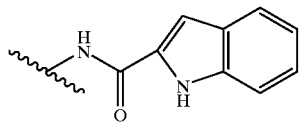

wherein the first N-substituted pyrrolidine ring is fused to the first vinylene group between $R_2$ and $R_3$ and is represented by the following structure:

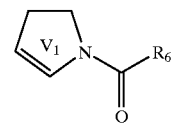

wherein $V_1$ represents the first vinylene group between $R_2$ and $R_3$. In the above radical, $R_6$ is selected from the group consisting of —$NH_2$ and a radical represented by the following structure:

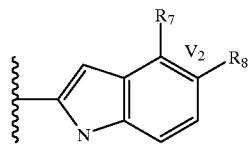

$R_7$ is selected from the group consisting of hydrogen, hydroxyl, O-alkyl (C1–C6), and a second N-substituted pyrrolidine ring; $R_8$ is selected from the group consisting of hydrogen, hydroxyl, O-alkyl (C1–C6), and the second N-substituted pyrrolidine ring; and $V_2$ represents the second vinylene group between $R_7$ and $R_8$. However, the following provisos pertain:

1. If $R_7$ participates in the N-substituted pyrrolidine ring, then $R_8$ also particlates in the N-substituted pyrrolidine ring; and
2. If $R_8$ participates in the N-substituted pyrrolidine ring only if $R_7$ also particlates in the N-substituted pyrrolidine ring; wherein the second N-substituted pyrrolidine ring is fused to the second vinylene group between $R_7$ and $R_8$ and is represented by the following structure:

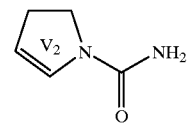

wherein $V_2$ represents the second vinylene group between $R_7$ and $R_8$.

Preferred embodiments of the invention include the following compounds:

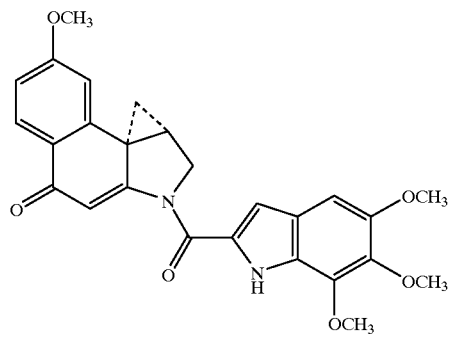

-continued
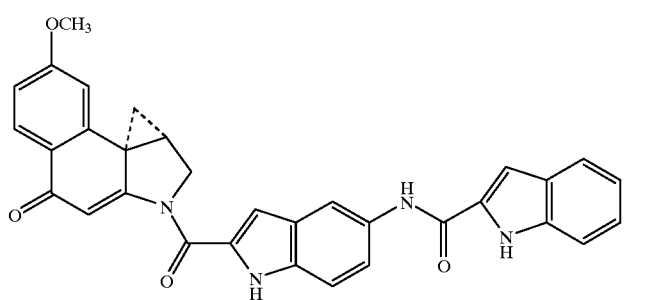
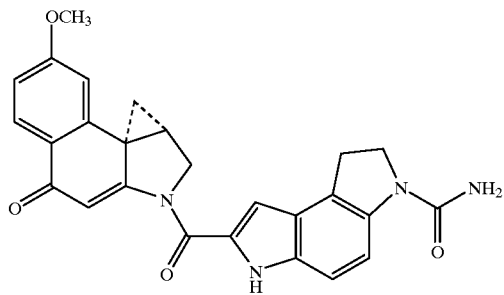
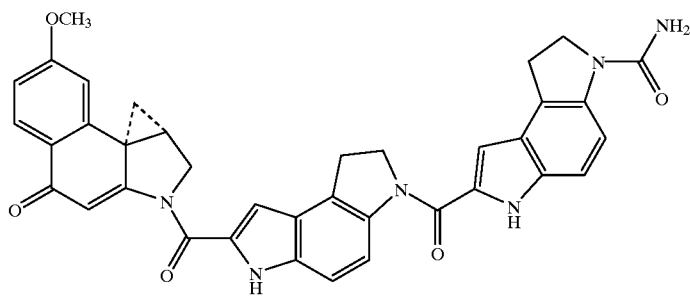
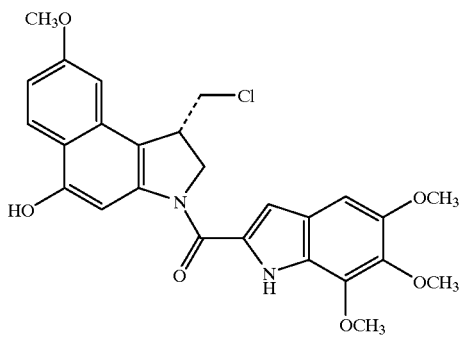
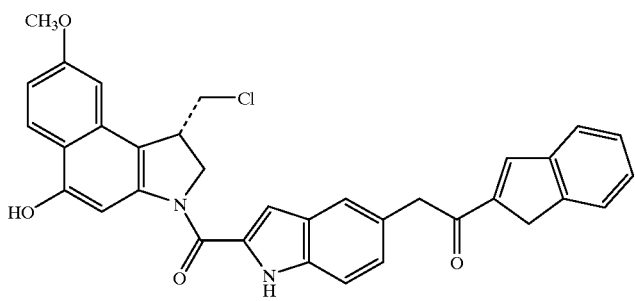

-continued

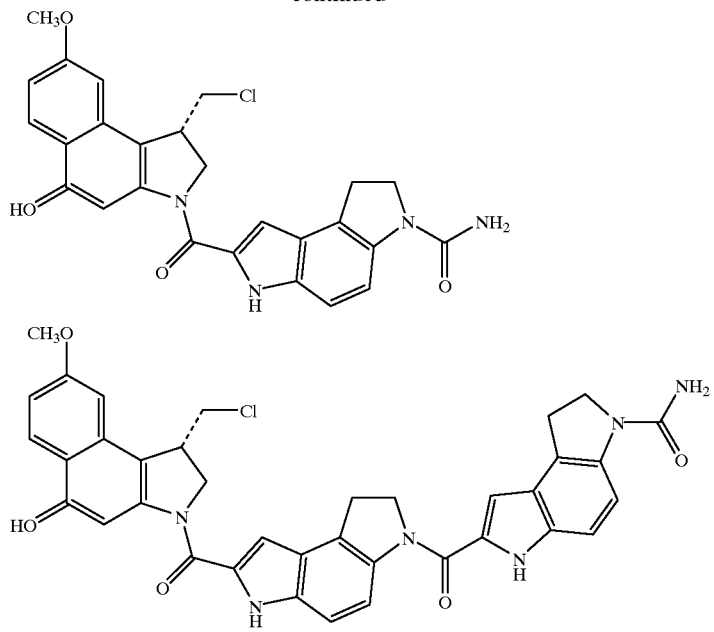

A second aspect of the invention is directed to the use of the above indicated compounds for alkylation of DNA.

MCBI (7-methoxy-1,2,9,9a-tetra-hydrocyclopropa[c]benz[e]indol-4-one) is a substituted CBI derivative bearing C7 methoxy group para to the C4 carbonyl. The core structure of the MCBI alkylation subunit was prepared by a modified Stobbe condensation-Friedel-Crafts acylation for generation of the appropriately functionalized naphthalene precursors (210 and 220) followed by 5-exo-trig aryl radical-alkene cyclization (228 to 230, 246 to 248) for completion of the synthesis of the 1,2-dihydro-3H-benz[e]indole skeleton and final Ar-3' alkylation of 236 for introduction of the activated cyclopropane. Two approaches to the implementation of the key 5-exo-trig free radical cyclization are detailed with the former proceeding with closure of 228 to provide 230 in which the required product functionalization was introduced prior to cyclization and the latter with Tempo trap of the cyclization product of the unfunctionalized alkene substrate 246 to provide 248. The latter concise approach provided the MCBI subunit and its immediate precursor in 12–13 steps in superb overall conversions (27–30%). Resolution of an immediate MCBI precursor and its incorporation into both enantiomers of 257–266, analogs of CC-1065 and the duocarmycins, are detailed. A study of the solvolysis reactivity and regioselectivity of N-BOC-MCBI (238) is described and the introduction of the C7 methoxy group was found to accelerate the rate of solvolysis by only 1.6×. This surprisingly modest effect suggests that protonation of the C4 carbonyl is not the rate determining step of solvolysis or acid-catalyzed nucleophilic addition, that little differential charge buildup occurs in the transition state and further supports the suggestion that the cyclopropane ring opening reaction requires the presence and assistance of a nucleophile (SN2 mechanism). No doubt this contributes to the DNA alkylation selectivity of this class of agents and implies that the positioning of an accessible nucleophile (adenine $N_3$) and not $C_4$ carbonyl protonation may be the rate determining event. This remarkably small electronic effect on the solvolysis rate had no impact on the solvolysis regioselectivity and stereoelectronically-controlled nucleophilic addition to the least substituted carbon of the activated cyclopropane was observed exclusively.

BRIEF DESCRIPTION OF THE DRAWINGS

FIG. 8 illustrates a table of agents examined wherein k represents the solvolysis rate constant measured at pH 3; $t_{1/2}$ represents the half life of the agent measured at pH 3 with the indicated $IC_{50}$ values and ultraviolate and infrared spectral data. The noted superscripts are defined as follows: (a) pH=3:50% $CH_3OH$-buffer, buffer is 4:1:20 (v:v:v) 0.1 M citric acid, 0.2 M $Na_2HPO_4$, and $H_2O$, respectively; (b) $CH_3OH$; (c) KBr; (d) THF; (e) Film; (f) Nujol; (g) at pH 2, k=1.53×10$^{-5}$ s$^{-1}$, $t_{1/2}$=12.5 hours; (h) at pH 2, k=1.62×10$^{-5}$ s$^{-1}$, $t_{1/2}$=11.5 hours.

FIG. 10 illustrates in vitro cytotoxic activity of MCBI agents examined and are shown in comparison with CBI agents.

FIG. 12 illustrates enantiomer distinctions which reveals that the MCBI-TMI enantiomers were found to exhibit analogous distinctions but somewhat smaller than those observed with CBI-TMI.

DETAILED DESCRIPTION

Figure 2:
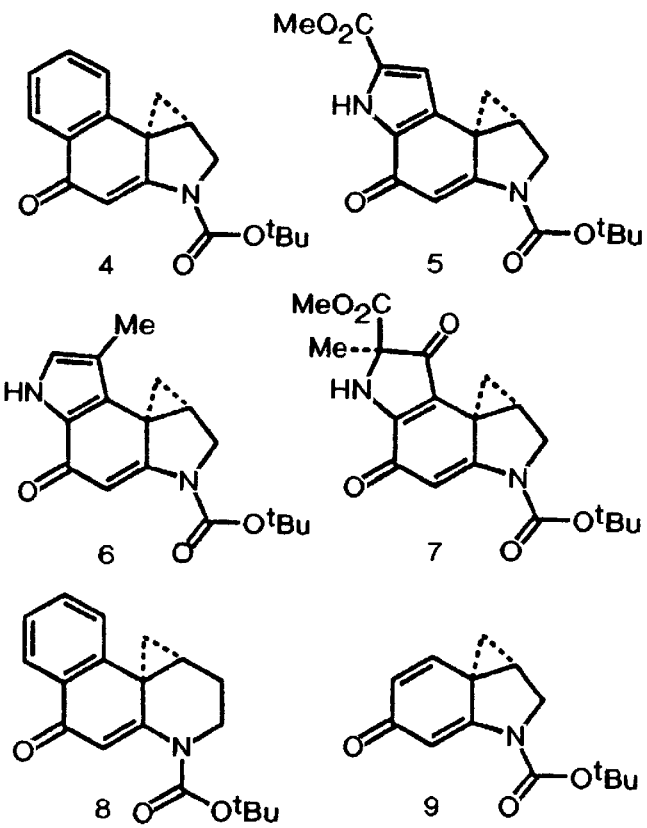
FIG. 2 illustrates the structures of agents 4–9 containing deep-seated modifications in the alkylation subunit. The lower scheme shows a direct comparison of MCBI with CBI.
Figure 2:
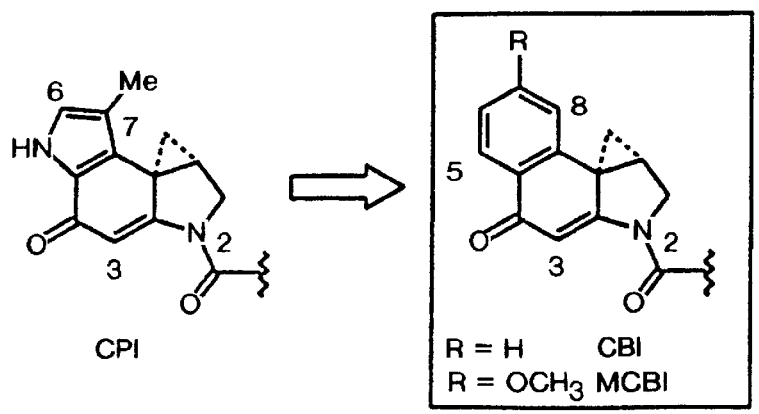

The invention embodies the first synthesis of substituted MCBI derivatives, 7-methoxy-1,2,9,9a-tetra-hydrocyclopropa[c]benz[e]-indol-4-one (MCBI), bearing a C7 methoxy substituent para to the C4 carbonyl. The direct comparison of MCBI with CBI was anticipated to permit an assessment of the magnitude of the electronic effects of the C7 substituent on chemical reactivity and, ultimately, the relationship of this functional reactivity with the biological properties (FIG. 2; MCBI structure).

Synthesis of MCBI (240) and N-BOC-MCBI (238)

Figure 1:
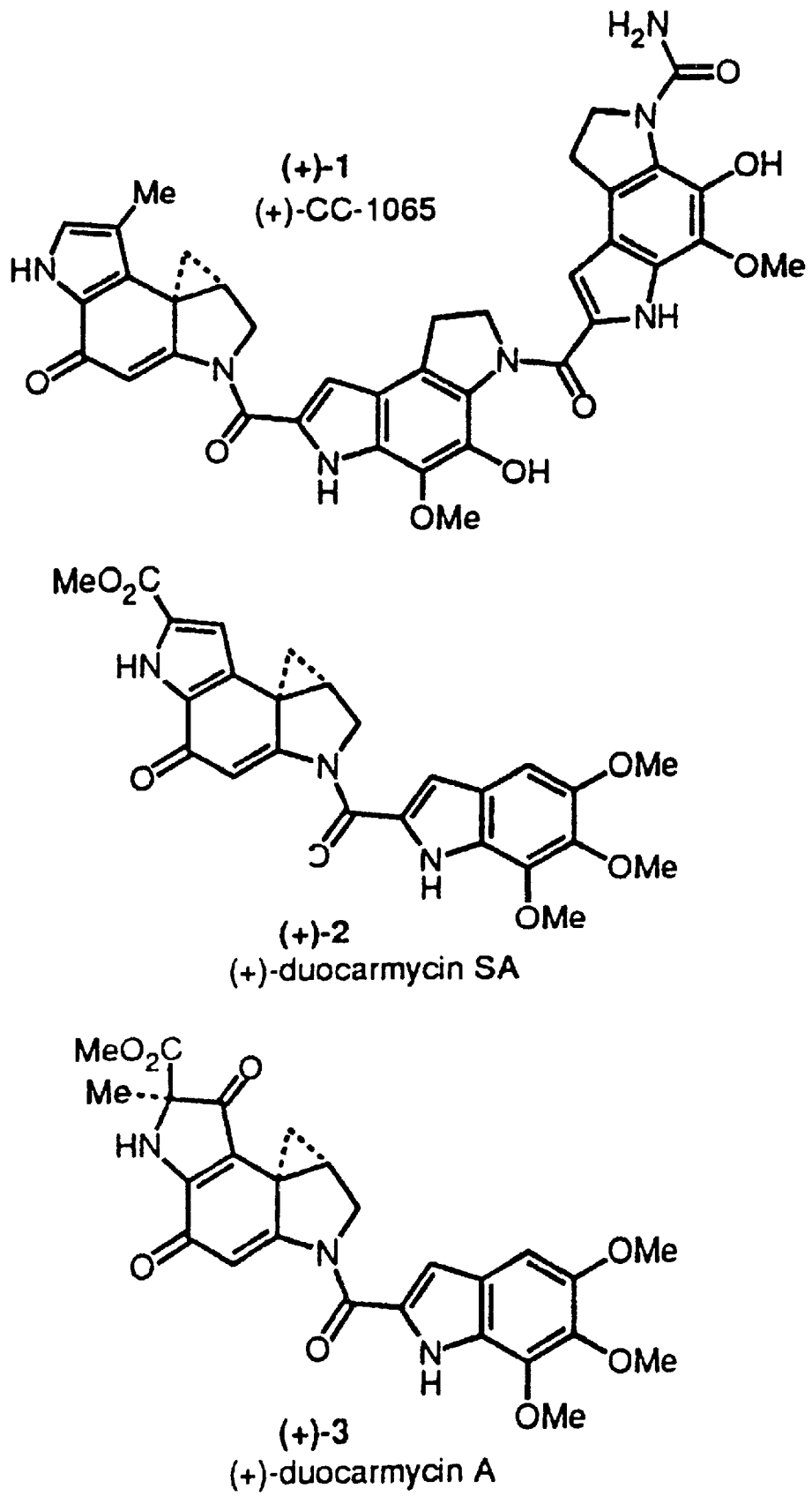
FIG. 1 illustrates the structures of (+)CC-1065 (1), and the duocarmycins 2–3.
Figure 3:
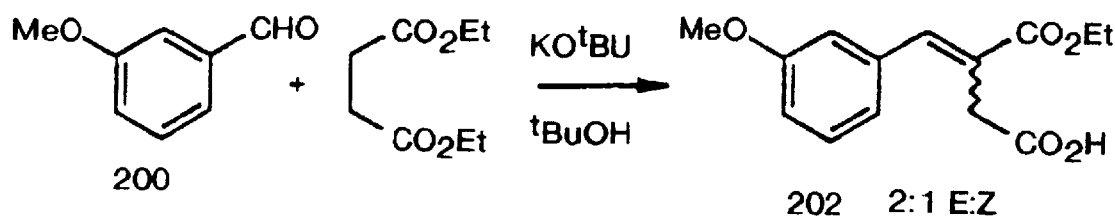
FIG. 3 illustrates the synthesis of early intermediate compounds 204, 206, 208 and 210.
Figure 3:
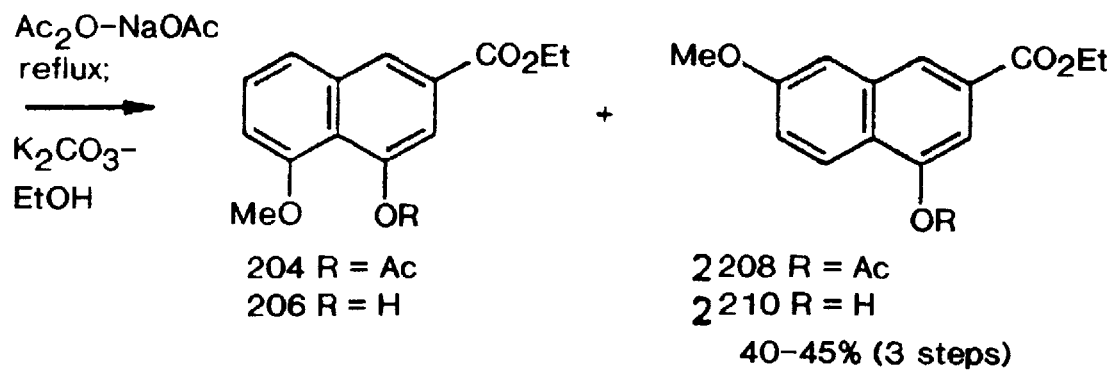
Figure 3:
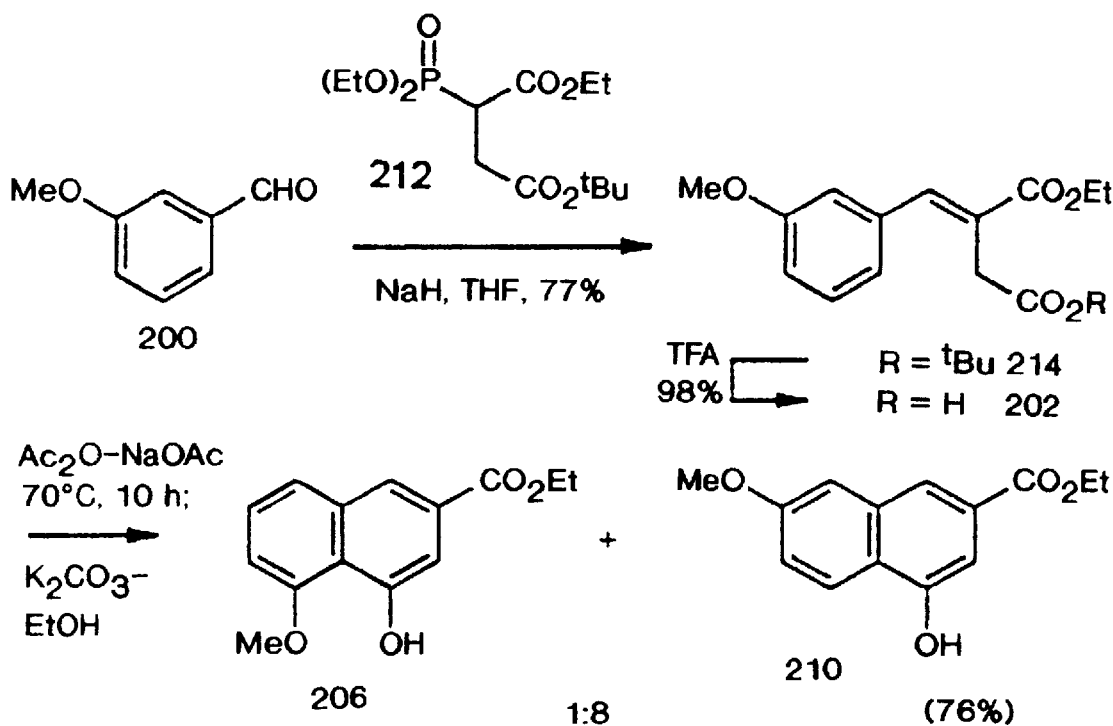

Stobbe (Stobbe, H. Chem. Ber. 1893, 26, 2312; Johnson et al. Org. React. 1951, 6, 1) condensation of 3-methoxybenzaldehyde (200; FIG. 3) with diethyl succinate (3–6 equiv) effected by treatment with t-BuOK (Johnson et al. Org. React. 1951, 6, 1; Baghos et al. Helv. Chim. Acta 1979, 62, 90) (2–4 equiv, t-BuOH, reflux, 1–2 hours, 74%) provided a 2:1 mixture of half esters 202 which were subjected to Friedel-Crafts acylation (1.0 equiv NaOAc, Ac$_2$O, reflux 5 hours) to provide a mixture of 210, its corresponding O-acetate 208 and significant amounts of the isomeric Friedel-Crafts products 204–206 (FIG. 3). Subsequent ethanolysis (K$_2$CO$_3$, EtOH) of the resulting mixture served to hydrolyze the O-acetates 204 and 208 providing a mixture of 210 and its isomer 206 which were readily separated by chromatography. Use of this approach provided 210 in a satisfactory 40–45% overall yield from 200 without deliberate purification of the intermediates 202 or 208 but suffered from erratic conversions and the preparative separation of the final isomeric products. The best conversions were observed when the Friedel-Crafts acylation was conducted under moderately dilute reaction conditions (0.1 versus 0.5 M). In part, the 2:1 E:Z mixture of initial half esters 202 dictated a harsh set of Friedel-Crafts acylation conditions capable of isomerization and cyclization of the unproductive Z-isomer. Attempts to improve the ratio of isomeric products using milder reaction conditions generally afforded lower overall conversions to 210 due to the less effective cyclization of the Z-isomer under the conditions examined (FIG. 1; top).

This was improved significantly by conducting the Stobbe condensation in a more controlled manner. Condensation of 200 with the Wadsworth-Horner-Emmons reagent 212 (Owten et al. Synth. Commun. 1993, 23, 2119; Gallagher et al. Tetrahedron Lett. 1994, 35, 289; Hughes et al. J. Chem. Soc., Perkin Trans. 1 1989, 449; Comber et al. J. Chem. Soc., Perkin Trans. 1 1991, 2783) (1 equiv, 1.05 equiv NaH, THF, 0 to 25° C., 10 hours, 81%) provided 214 in which the desired E-isomer predominated ≧20:1 (FIG. 3). Selective acid-catalyzed deprotection of the t-butyl ester (98%) followed by Friedel-Crafts acylation effected by treatment with Ac$_2$O—NaOAc (reflux, 1 hour) provided a mixture of 202–210. Subsequent hydrolysis of the O-acetates (K$_2$CO$_3$, EtOH) provided 210 (68% overall) and 206. Notably, the reaction time required for completion of the Friedel-Crafts acylation was significantly reduced with use of the pure E isomer of 202 and the yield of 210 improved as well. Moreover, this permitted the use of milder Friedel-Crafts reaction conditions (Ac$_2$O, 1.1 equiv NaOAc, 70° C., 10 hours) and this modification further improved the conversions and ratio of 210:206 (8:1). Following this protocol, 210 was isolated in 76% overall yield from 202. Similarly, treatment of 202 with TFAA-NaOAc (Bonnett-Delpon et al. J. Org. Chem. 1988, 53, 754) (reflux, 30 hours, 57%) provided 210 in slightly lower conversions as a 9:1 mixture of 210:206. Alternative efforts to first convert 202 to the corresponding acid chloride (2 equiv (COCl)$_2$) followed by Lewis acid-catalyzed cyclization (AlCl$_3$, 38%; FeCl$_3$, 46%; SnCl$_4$, 54%) did not improve on these conversions. Not only was the overall conversion of 200 to 210 improved using this modification of the Stobbe condensation, but the ability to isolate and characterize pure intermediates in route to 210 permitted an accurate assessment and optimization of each reaction step (FIG. 3).

Figure 4A:
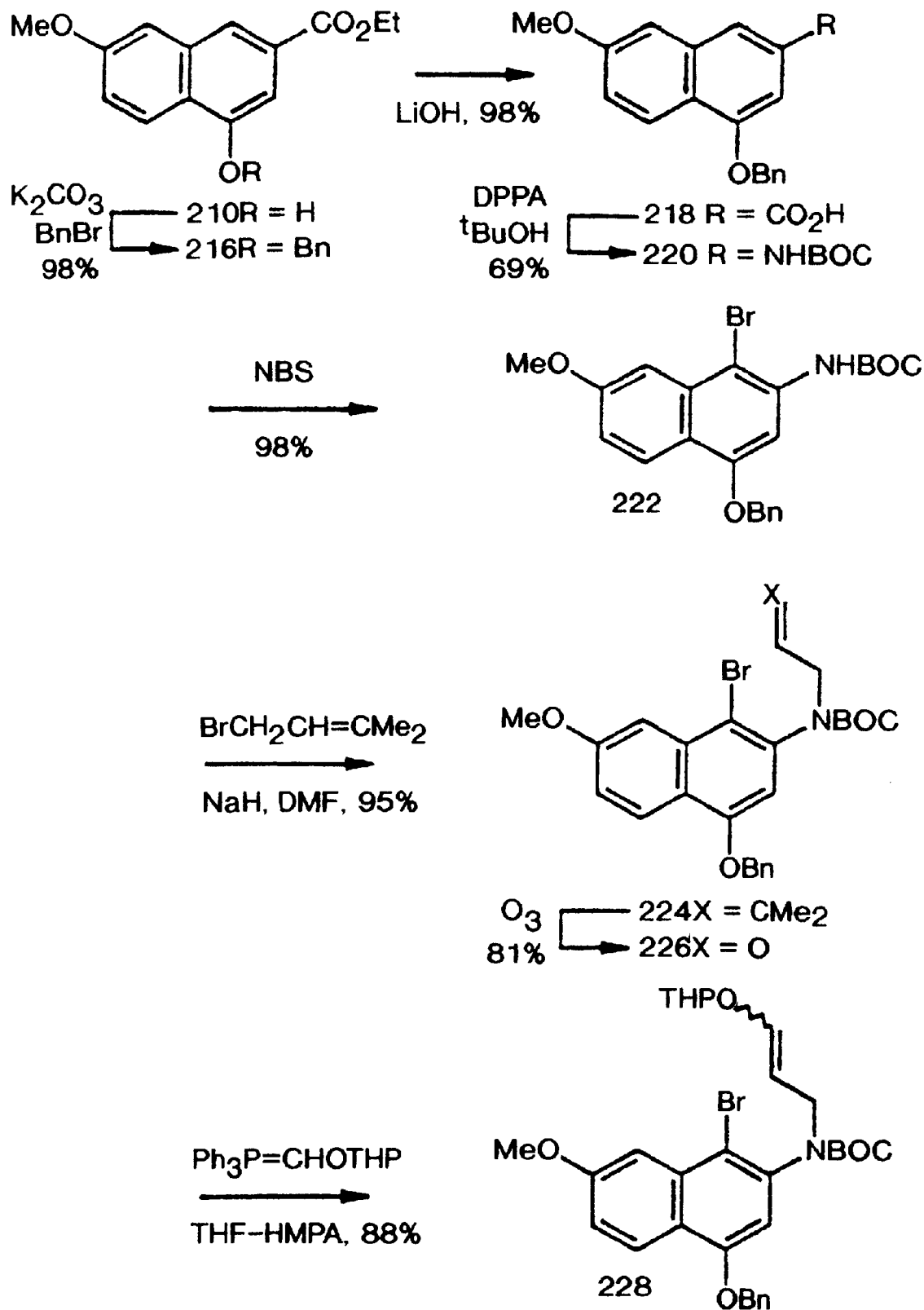
FIG. 4 illustrates the synthesis of advanced intermediate MCBI compounds 238 and 240.
Figure 4B:
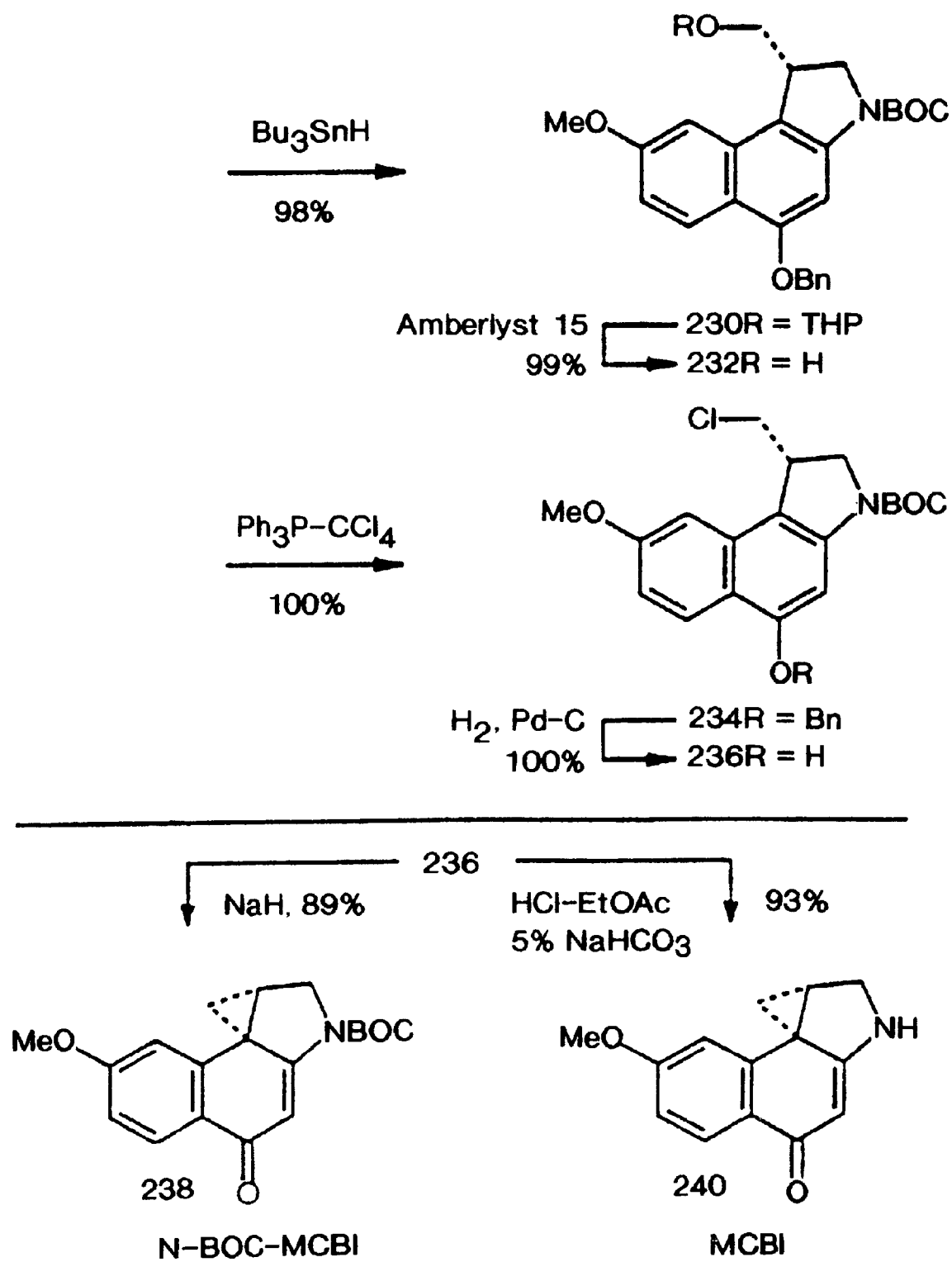

Protection of the phenol 210 as its benzyl ether 216 (98%) followed by hydrolysis of the ethyl ester (98%) and Curtius rearrangement of the resulting carboxylic acid 218 employing the Shioiri-Yamada reagent (DPPA; Shioiri et al. *J. Am. Chem. Soc.* 1972, 94, 6203; Ninomiya et al. *Tetrahedron* 1974, 30, 2151) in t-BuOH provided the carbamate 220 directly in excellent conversions (69%), FIG. 4. Low temperature, acid-catalyzed C-4 bromination of 220 (1.2 equiv NBS, cat $H_2SO_4$, THF, $-78°$ C., 5 hours, 98%) clearly provided 222 whose structure was confirmed with observation of a diagnostic $C_3$—H/OCH$_2$PH NOE cross peak in the 2D $^1$H—$^1$H NMR spectrum. Alkylation of the sodium salt of 222 (1.3 equiv NaH, DMF, 25° C., 30 minutes) with 1-bromo-3-methyl-2-butene (3 equiv, DMF, 25° C., 8 hours, 95%) followed by a carefully monitored, low-temperature ozonolysis of 224 and subsequent reductive workup (Me$_2$S) of the crude ozonide provided 226 (81%). In the optimization of the ozonolysis reaction, the use of more extended reaction times without an immediate, low temperature quench of excess $O_3$ was found to lead to the rapid generation of a further oxidation product. Consequently, adherence to the reaction conditions and particularly the reaction time detailed were critical to the success of the conversion of 224 to 226. Wittig introduction of the vinyl ether 228 proved most effective with low temperature generation of $Ph_3P=CHOTHP$ (Schlude, H. *Tetrahedron* 1975, 31, 89) in THF followed by reaction with 226 in THF-HMPA over a sustained reaction period and provided a mixture of E:Z olefin isomers in excellent yield (88%). Treatment of 228 with Bu$_3$SnH (2 equiv, C$_6$H$_6$, cat AIBN, 80° C., 2 hours, 95–98%) provided 230, the product of 5-exo-trig aryl radical-alkene cyclization, in superb yield. Subsequent THP deprotection (Bongini et al. *Synthesis,* 1979, 618) of 230 provided the free alcohol 232 (99%) and was accomplished without evidence of N-BOC deprotection. Conversion of 232 to the primary chloride 234 (2 equiv Ph$_3$P, 6 equiv CCl$_4$, CH$_2$Cl$_2$, 25° C., 20 hours, 99–100%; Hooz et al. *Can. J. Chem.* 1968, 46, 86) followed by transfer hydrogenolysis (Beig et al. *Synthesis* 1985, 76) of the benzyl ether (99–100%) and subsequent spirocyclization effected by treatment of 236 with NaH (3 equiv, THF, 0° C., 30 minutes, 89%) provided N-BOC-MCBI (238). Similarly, acid-catalyzed deprotection of 236 (3N HCl-EtOAc, 25° C., 20 minutes) followed by spirocyclization of the crude indoline hydrochloride salt upon exposure to 5% aqueous NaHCO$_3$-THF (1:1, 25° C., 1.5 hours, 93%) cleanly provided MCBI (240); (FIG. 4).

Figure 5:
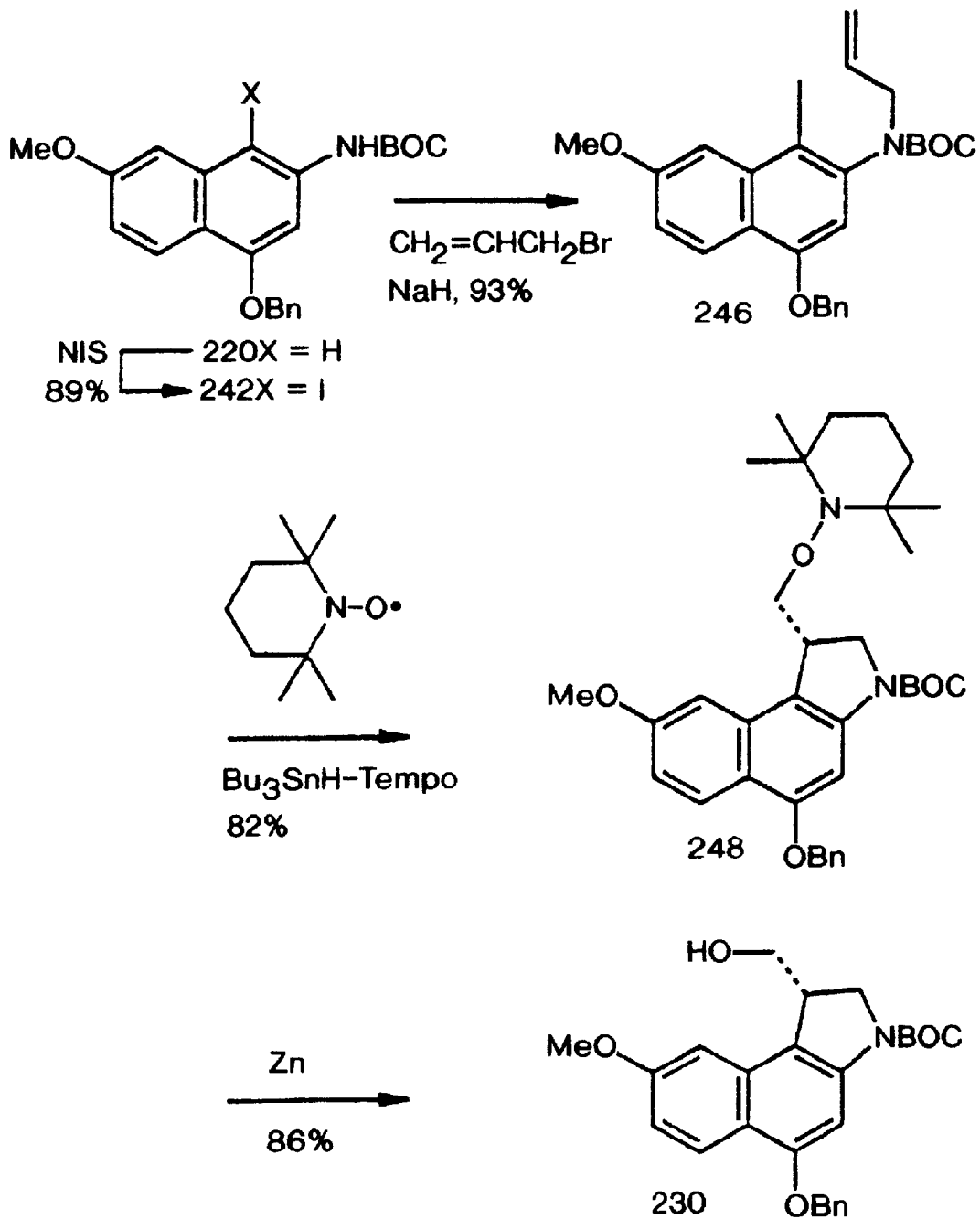
FIG. 5 illustrates the synthesis of advanced intermediate MCBI compound 230.

Subsequent to the completion of this synthesis of 238 and 240, alternative methods to effect the key 5-exo-trig aryl radical alkene cyclization were investigated (Boger et al. *J. Org. Chem.* 1995, 60, 1271) In our initial approach, the cyclization of the enol ether 238 proceeded in excellent conversion in part due to the use of an activated acceptor alkene which accelerates the rate of ring closure and reinforces the inherent preference for 5-exo-trig cyclization. In addition, the vinyl ether incorporates into the cyclization substrate the full functionalization required in the desired cyclization product. However, the natural limitation of this approach is the requirement to incorporate the product functionality into the acceptor alkene of the free radical cyclization substrate and this entailed a carefully defined ozonolysis reaction and subsequent Wittig reaction with a functionalized methylenetriphenylphosphorane. A shorter, more efficient preparation of 232 was accomplished based on the successful Tempo trap (Boger et al. *J. Org. Chem.* 1995, 60, 1271) of an aryl radical-alkene 5-exo-trig cyclization of an unactivated alkene that precludes the need for alkene functionalization prior to cyclization. Selective, acid-catalyzed C4 iodination of 220 effected by low-temperature treatment with NIS (1.1 equiv, cat TsOH, THF-CH$_3$OH, $-78°$ C., 3 hours, 89%) followed by alkylation of the sodium salt of 242 (1.25 equiv NaH, DMF, 0° C., 50 minutes) with allyl bromide (3 equiv, DMF, 25° C., 3h, 93%) provided 246 (FIG. 5). Treatment of a mixture of 246 and Tempo (6 equiv) in benzene with Bu$_3$SnH (5×1.0 equiv, 70° C., 1 hour) provided 248 (82%) cleanly. Similarly, treatment of 246 and Tempo (6 equiv) in toluene with (Me$_3$Si)$_3$SiH (5×1 equiv, 80° C., 10 hours) provided 248 (84%) in a reaction that required slightly longer reaction times for completion. Tempo hydrogen atom abstraction from Bu$_3$SnH or (Me$_3$Si)$_3$SiH (Bu$_3$SnH>(Me$_3$Si)$_3$SiH) presumably serves to initiate the reaction cascade of tributyltin radical abstraction of iodide from 246, 5-exo-trig aryl radical-alkene cyclization which proceeds at an exceptionally fast rate and suffers no competitive reduction or intermolecular Tempo trap, and final Tempo trap of the cyclization product primary radical without competitive hydrogen atom abstraction from Bu$_3$SnH. The competitive reaction of tributyltin radical with Tempo versus 246 presumably accounts for the requirements for excess Bu$_3$SnH (3–5 equiv) and Tempo (6 equiv). Reductive cleavage of 248 to provide 230 was effected by treatment with Zn (12 equiv, 3:1:1 HOAc-THF-H$_2$O, 70° C., 2 hours, 86%) (FIG. 5).

Resolution. The advanced synthetic intermediate 236, the penultimate intermediate to the MCBI-based analogs, was directly and efficiently resolved on an analytical or preparative Daicel Chiralcel OD column ($\alpha$=1.17) (Boger et al. *J. Am. Chem. Soc.* 1994, 116, 7996) This convenient procedure which avoids diastereomeric derivatization, separation, and dederivatization was found to be best conducted with 236 although 234 ($\alpha$=1.12) and N-BOC-MCBI (238, $\alpha$=1.16) were also capable of direct resolution on the Chiralcel OD columns. For our purposes, 236 could be separated on a semipreparative 10 $\mu$m, 2×25 cm OD HPLC column (2% i-PrOH-hexane, 5 mL/min) with a 90–100% recovery of the total sample. Conversion of natural (1S)- and ent-(1R)-236 to (+)- and ent-(−)-N-BOC-CBI (238), and (+)- and ent-(−)-CBI (240 ) followed the experimental procedures detailed in FIG. 4.

The assignment of the absolute configuration was based initially on the relative cytotoxic potencies of natural (+)- and ent-(−)-N-BOC-MCBI and related analogs with the former exhibiting more potent activity consistent with observations made with 4–9. Ultimately, this was confirmed in a preliminary examination of the DNA alkylation selectivity of the enantiomers of the advanced analogs 257–266. Notably, the sign of rotation for the natural and unnatural enantiomers of N-BOC-MCBI and MCBI as well as those of the advanced analogs were found to be the same as those observed with 4–7 and 9 and their advanced analogs.

MCBI-TMI (254), MCBI-indole$_2$ (258), MCBI-CDPI$_1$ (262), and MCBI-CDPI$_2$ (266)

Figure 6:
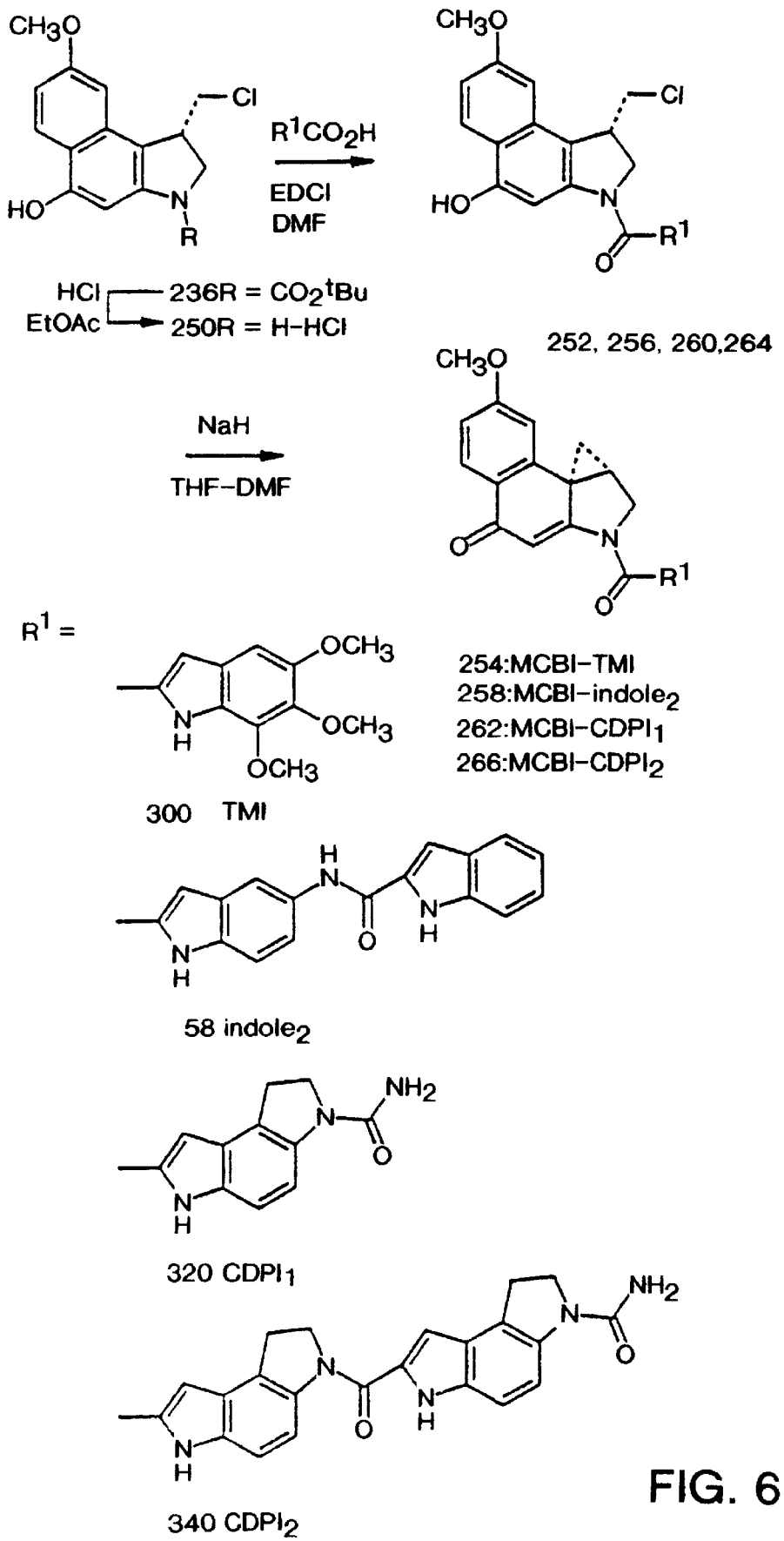
FIG. 6 illustrates the synthesis of MCBI coupled agents 252, 254, 256, 258, 260, 262, 264, and 266.

The MCBI alkylation subunit was incorporated into the CC-1065 and the duocarmycin analogs as detailed in FIG. 6. Acid-catalyzed deprotection of 236 (4M HCl-EtOAc, 25° C., 30 minutes) followed by immediate coupling of the unstable amine hydrochloride salt 250 with 5,6,7-trimethoxyindole-2-carboxylic acid (300, 3 equiv EDCI, DMF, 25° C., 10 hours, 85%; Boger et al. *J. Org. Chem.* 1990, 55, 4499), 58 (3 equiv EDCI, DMF, 25° C., 10 hours, 78%; Boger et al. *J. Org. Chem.* 1984, 49, 2240), CDPI$_1$ (320, 3 equiv EDCI, DMF, 25° C., 12 hours, 71%; Boger *J. Org. Chem.* 1987, 52, 1521), and CDPI$_2$ (340, 3 equiv EDCI, DMF, 25° C., 6 hours, 68%; Boger et al. *J. Org. Chem.* 1987, 52, 1521; Boger et al. *J. Org. Chem.* 1984, 49, 2240) deliberately conducted in the absence of added base which promotes competitive closure of 250 to 240 provided the immediate precursors 257, 256, 260, and 264, respectively. Notably, the ease of the couplings of 250 with the carboxylic acids 300–340 diminished as their solubility decreased (300, 58>320>340) which necessarily shows the rate of reaction. Subsequent treatment of the coupled agents with NaH (3.0 equiv, THF-DMF 3:1, 0° C., 30 minutes) provided MCBI-TMI (254, 90%), MCBI-indole$_2$ (258, 86%), MCBI-CDPI$_1$ (262, 90%), and MCBI-CDPI$_2$ (266, 94%), respectively, in excellent conversions. Optimal conversions were observed when the workup of the spirocyclization reaction was conducted with an aqueous phosphate buffer (0.2 M, pH 7) at low temperature (0° C.). Under these conditions the adventitious hydrolysis of MCBI (240) was minimized (FIG. 6).

Chemical Solvolysis: Reactivity

Two fundamental characteristics of the alkylation subunits have proven important in the studies of 4–9 to date. The first is the stereoelectronically-controlled acid-catalyzed ring opening of the activated cyclopropane which dictates preferential addition of nucleophile to the least substituted cyclopropane carbon. The second is the relative rate of acid-catalyzed solvolysis which has been found to accurately reflect the functional reactivity of the agents and to follow a fundamental, direct relationship between solvolysis stability and in vitro cytotoxic potency (Boger et al. *J. Am. Chem. Soc.* 1994, 116, 6461; Boger et al. *J. Am. Chem. Soc.* 1994, 116, 11335).

Provided the C7 substitution of the CBI nucleus would not perturb the stereoelectronic effects on the acid-catalyzed ring opening, this subtle structural change of introducing a C7 methoxy substituent was anticipated to increase the solvolytic reactivity of the agents through electronic activation of C4 carbonyl protonation required of solvolysis. Moreover, it was anticipated that solvolysis would still occur with exclusive cleavage of the C8b-C9 bond with addition of a nucleophile to the least substituted C9 cyclopropane carbon rather than by cleavage of the C8b-C9a bond with ring expansion and addition of a nucleophile to C9a. Notably, the latter cleavage would place the developing positive charge on a preferred secondary versus primary center and, in preceding agents, this preference was overridden by the inherent stereoelectronic control.

Figure 9A:
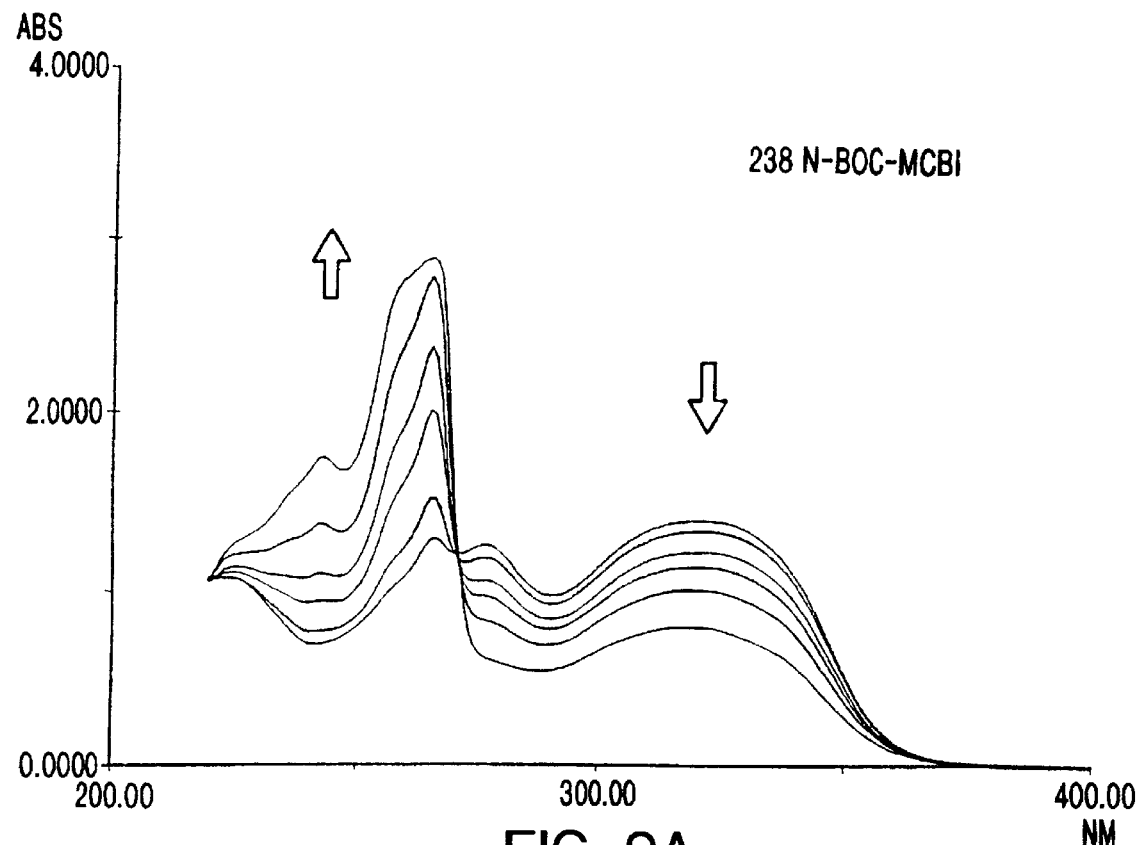
FIG. 9 illustrates a solvolysis study (UV spectra) of N-BOC-MCBI (238, top) and MCBI (240, bottom) in 50% $CH_3OH$-aqueous buffer (pH 3.0, 4:1:20 (v/v/v) 0.1 M citric acid, 0.2 M $NaH_2PO_4$, and $H_2O$, respectively). The spectra were recorded at regular intervals and only a few are shown for clarity. Top: 1, 0 hour; 2, 4 hours; 3, 27 hours; 4, 70 hours; 5, 105 hours; 6, 177 hours. Bottom: 1, 0 hour; 2, 4 hours; 3, 27 hours; 4, 70 hours; 5, 177 hours; 6, 752 hours.
Figure 9B:
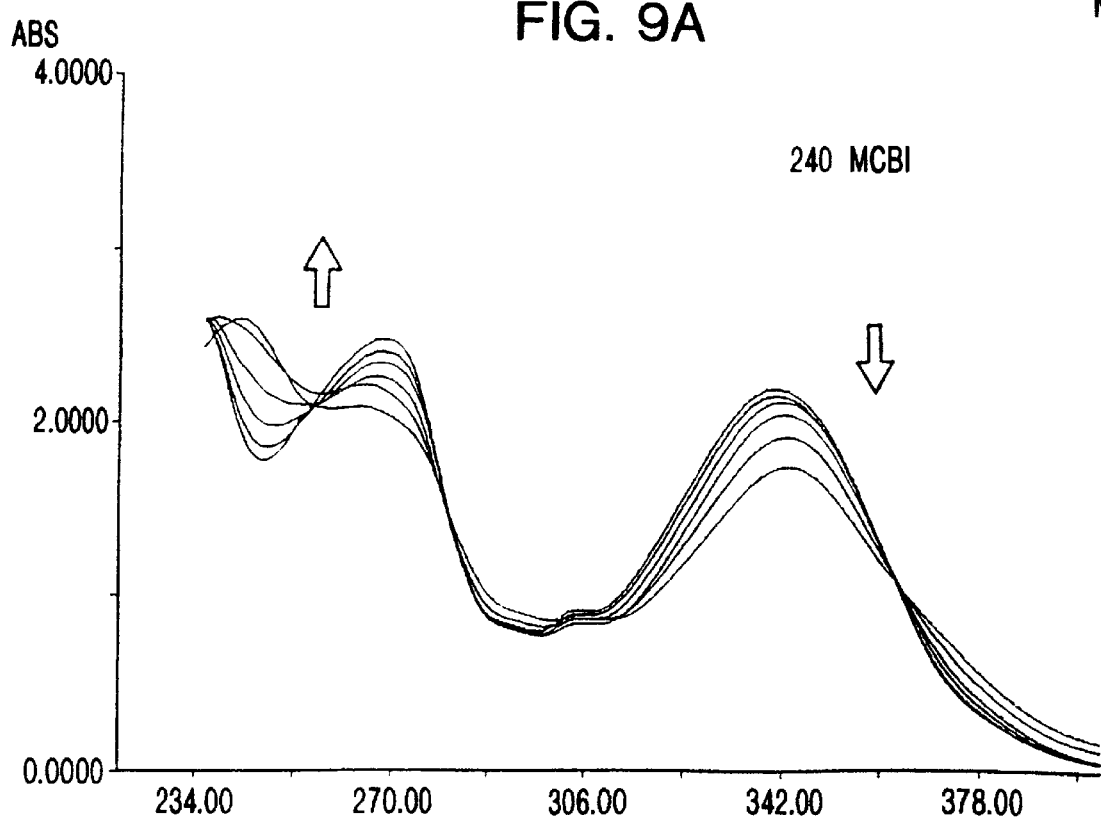
Figure 11A:
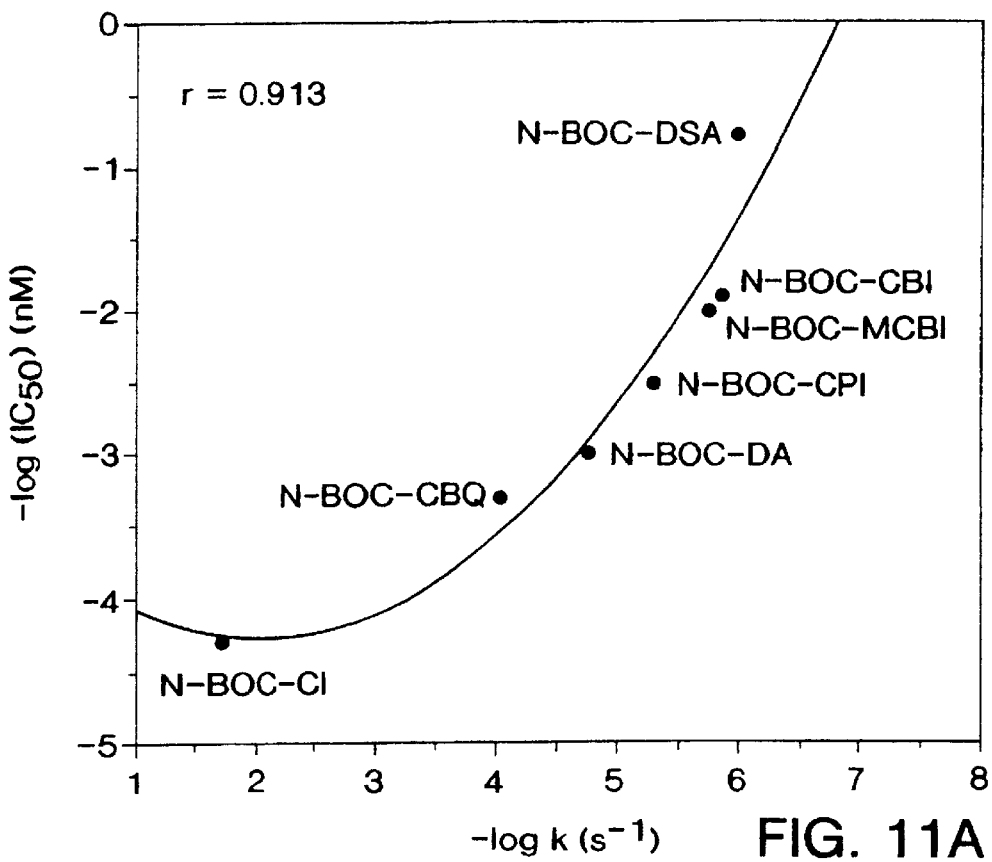
FIG. 11 illustrates that the agents examined are found to follow a direct relationship between functional stability ($-\log k$) and cytotoxic potency ($-\log (IC_{50})$).
Figure 11B:
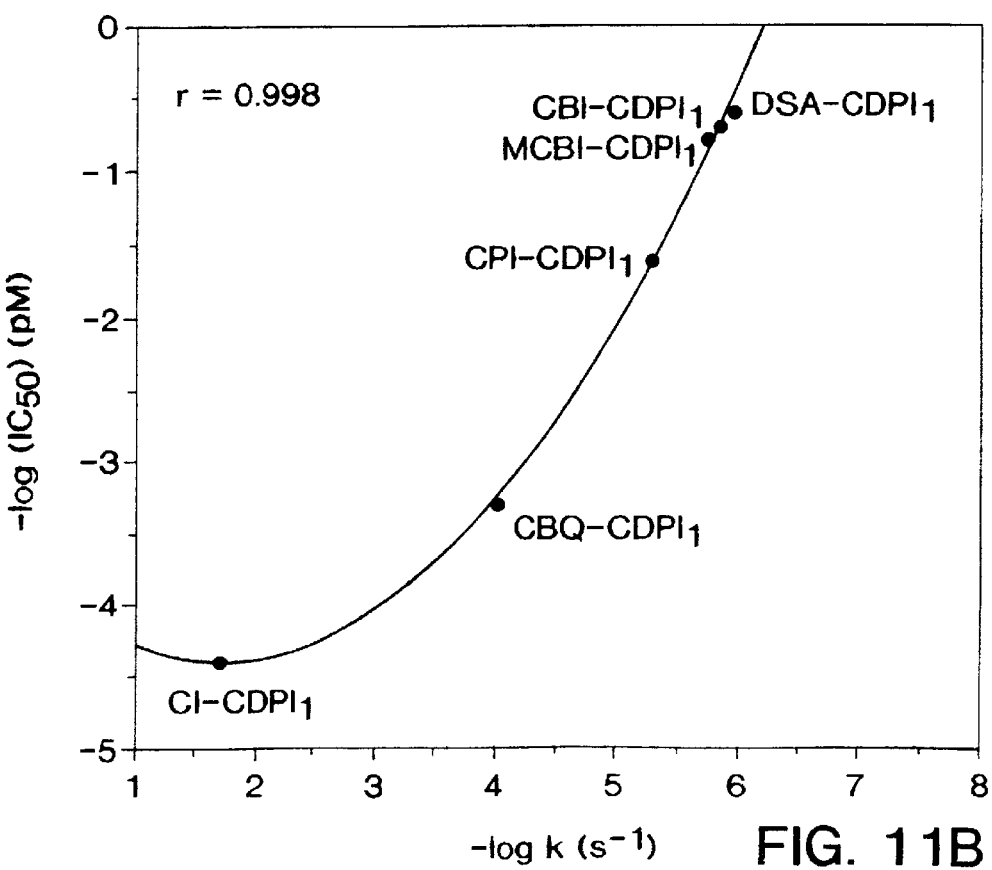
Figure 11C:
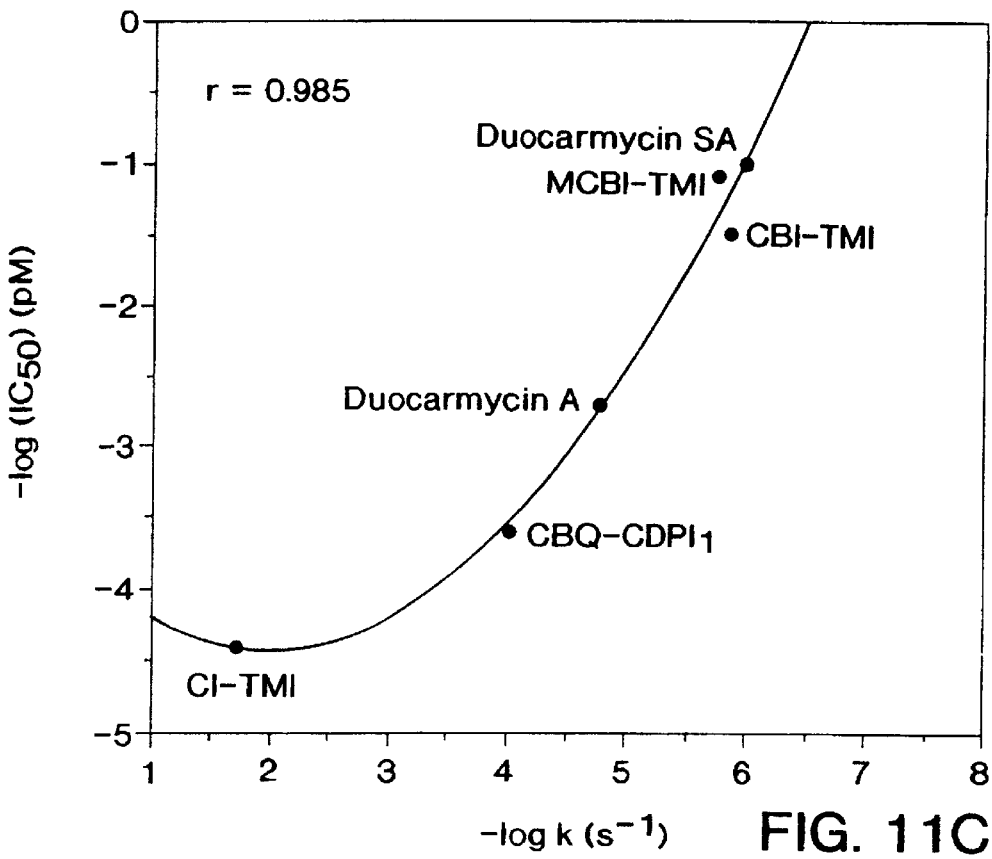
Figure 11D:
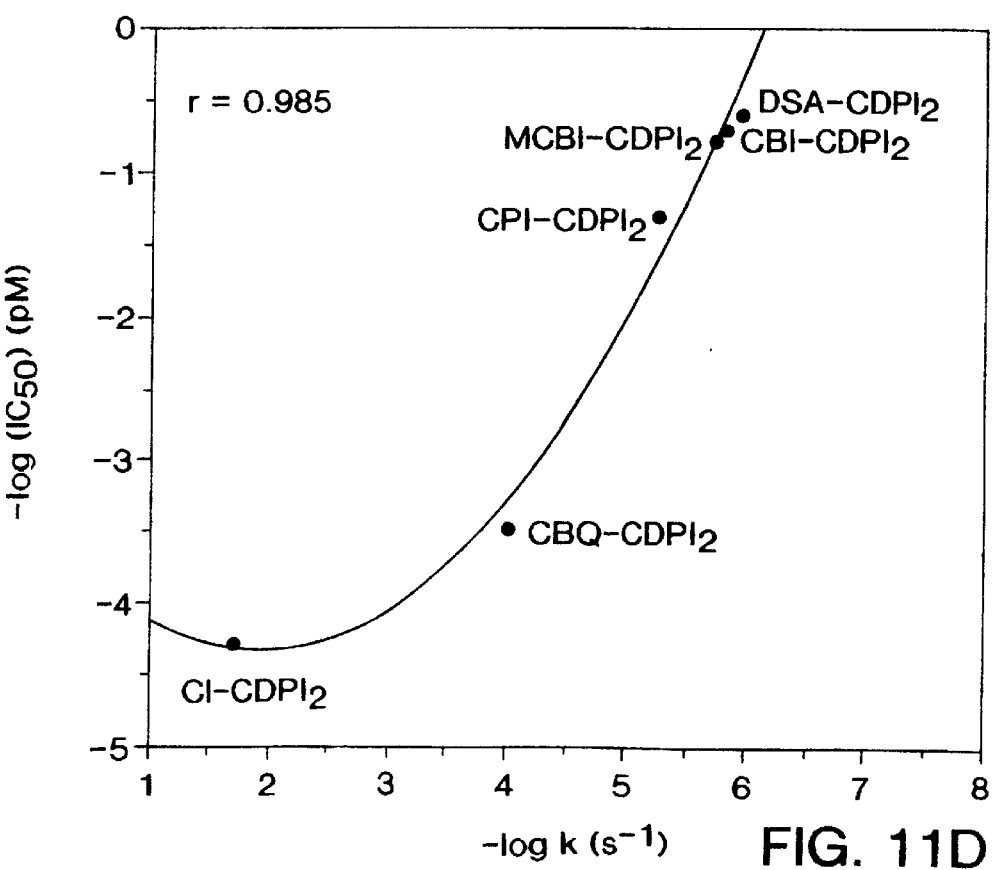

Consistent with expectations, N-BOC-MCBI (238, $t_{1/2}$=80 hours, k=2.41×10$^{-6}$ s$^{-1}$) proved to be more reactive toward chemical solvolysis at pH 3 than N-BOC-CBI (4, $t_{1/2}$=133 hours) but the difference was much less pronounced than anticipated and 238 was still substantially more stable than N-BOC-CPI (6, $t_{1/2}$=36.7 hours), FIG. 8. Thus, N-BOC-MCBI exhibits a half-life only 0.6 times shorter than that of the parent agent N-BOC-CBI (4) at pH 3. At pH 7 (1:1 H$_2$O—CH$_3$OH) where 4–7 show no evidence of solvolysis when monitored for 1–2 weeks, N-BOC-MCBI (238) similarly did not show evidence of solvolysis. The solvolysis was followed spectrophotometrically by UV with the disappearance of the long-wavelength absorption band of the MCBI chromophore (324 nM) and with the appearance of a short-wavelength absorption band (266 nm) attributable to seco-N-BOC-MCBI (FIG. 9). Like CPI and CBI, MCBI (240, $t_{1/2}$=334 hours, k=5.76×10$^{-7}$ s$^{-1}$) proved substantially more stable to solvolysis than N-BOC-MCBI (238) and this is presumably the result of preferential N$^3$-protonation versus O-protonation that is required for solvolysis catalysis. Nearly identical to the trends exhibited by 4–9, MCBI (240, $t_{1/2}$=334 hours, k=5.76×10$^{-7}$ s$^{-1}$) proved to be only slightly more reactive than CBI ($t_{1/2}$=930 hours, k=2.07×10$^{-7}$ s$^{-1}$)$^{25}$ and 6–7× more reactive than DSA ($t_{1/2}$=2150 hours, k=8.9×10$^{-8}$ s$^{-1}$)$^{16}$ but less reactive than CPI (FIGS. 8–9).

Thus, the rate of acid-catalyzed solvolysis of N-BOC-MCBI (238) was predictably faster than that of N-BOC-CBI (4) due to the electronic activation by the C7 methoxy substituent, but the magnitude of this effect is remarkably modest (1.6×) and revealing. First and foremost, it suggests that protonation of the C4 carbonyl is not the rate determining step of solvolysis or acid-catalyzed nucleophilic addition. Using the $\alpha_{p+}$ value of –0.78 for the methoxy substitute, this provides a remarkably small ρ value of –0.28 for the acid-catalyzed solvolysis reaction. Although this small value for ρ is based on a single comparison and subject to error, it is analogous to a similarly low ρ value derived from a larger set of comparisons (–0.30). Although many mechanistic interpretations of ρ are acknowledged, the most general states that it is a measure of the charge seen by the substituent in the reaction but encompasses other factors including the electron demand, the charge delocalization, the transition state position, and transmission of substituent effects for the reaction under study (Bradamante, S.; Pagani, G. A. *J. Org. Chem.* 1980, 45, 10) Since these factors are not independent, it is not often possible to distinguish the effects. However, an unusually small negative ρ value of –0.3 may indicate little differential positive charge buildup at the reaction center and suggest a strict SN2 mechanism for ring opening. Qualitatively, this is easily appreciated by recognizing that the C7 methoxy substitute of 238 and 240 has only a very modest 1.6-fold effect on the rate of acid-catalyzed solvolysis. The observation of clean SN2 solvolysis reaction products for the abnormal ring expansion addition to the activated cyclopropane of the closely related 8 coupled with the surprisingly small ρ value exhibited by the reaction suggests that little differential charge buildup occurs in the transition state and that the observation of reaction requires the presence and assistance of the nucleophile. No doubt this contributes to the DNA alkylation selectivity of this class of agents and implies that the positioning of an accessible nucleophie (adenine N3) and not C4 carbonyl protonation may be the rate determining event.

Chemical Solvolysis: Regioselectivity

Figure 7:
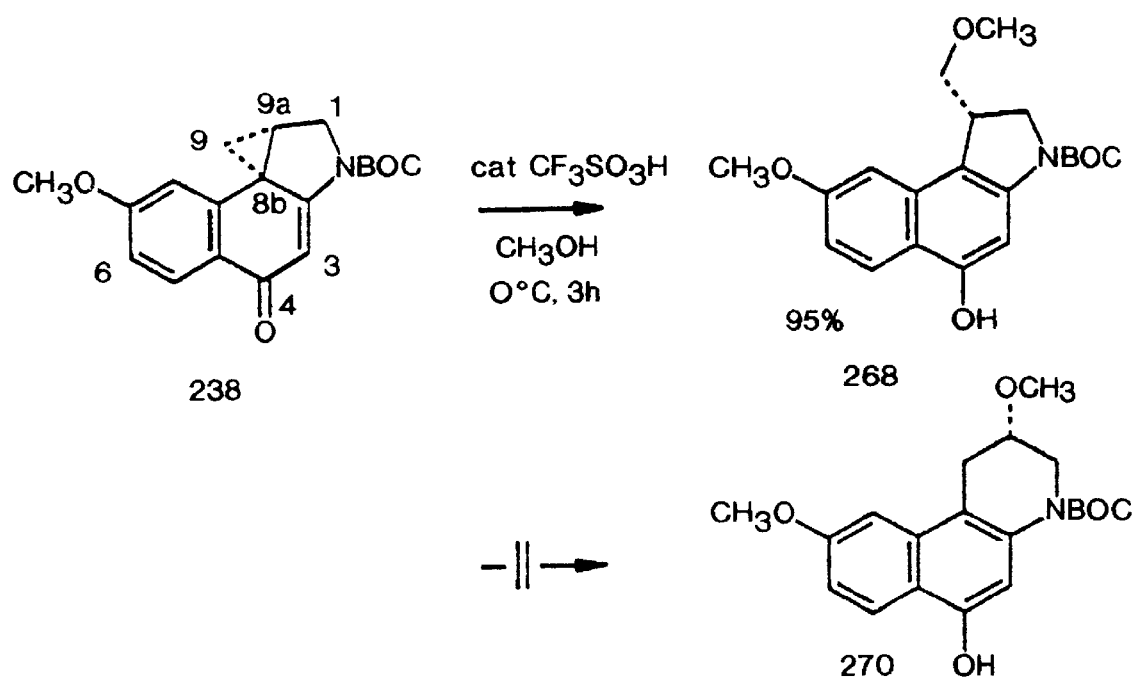
FIG. 7 illustrates the solvolysis of advanced intermediate MCBI compound 29 to a single product compound 47.

Treatment of N-BOC-MCBI (238) with 0.1 equiv CF$_3$SO$_3$H in CH$_3$OH (0° C., 3 hours) resulted in the clean solvolysis to provide a single product 238 (95%), FIG 7. No N-BOC deprotection or olefin was observed and the methanolysis proceeded without alteration of the stereoelectronically-controlled regioselectivity. Clean cleavage of the C8b-C9 bond with addition of CH$_3$OH to the least substituted C9 cyclopropane carbon was observed to provide 268 and no cleavage of the C8b-C9a bond with a ring expansion and addition of CH$_3$OH to C9a to provide 270 was detected (>20:1). Notably, this is in sharp contrast to solvolysis studies of the more reactive alkylation subunits of CC-1065, duocarmycin A, and CBQ where significant amounts of the abnormal ring expansion solvolysis products have been detected. Nonetheless, the observations are consistent with our prior studies of N-BOC-CBI (4) where no (>20:1) ring expansion solvolysis product was detected (Boger et al. *J. Org. Chem.* 1990, 55, 5823). To date the abnormal ring expansion solvolysis products have only been detected with the chemically more reactive agents, i.e. 6–8, and are only especially prevalent in one such system where the stereoelectronic alignment of both cyclopropane bonds are equivalent, i.e. 8 (Boger et al. *J. Am. Chem. Soc.* 1994, 116, 6461; Boger et al. *J. Am. Chem. Soc.* 1994, 116, 11335). Importantly, this stereoelectronically-controlled acid-catalyzed nucleophilic addition to the CBI-based agents including the MCBI-based agents which proceeds with >20:1 regioselectivity provides an additional advantage of the agents over the CPI-based analogs of CC-1065 which have been found to exhibit a more modest 4:1 selectivity (Warpehoski et al. *J. Am. Chem. Soc.* 1994, 116, 7573).

In Vitro Cytotoxic Activity

The natural enantiomers of the MCBI-based agents have been found to exhibit a cytotoxic potency that is slightly less potent or not distinguishable from that of the corresponding CBI-based agent (FIG. 10). Although the magnitude of the reactivity differences are too small and the variabilities in the cytotoxic assays too large to permit a critical comparison of the CBI and MCBI agents, the qualitative trends are generally those expected. Importantly and consistent with their relative reactivity, the agents were found to follow the well established direct relationship between functional stability and cytotoxic potency observed in prior studies with the full set of agents that have been examined to date (FIG. 11). Analogous to prior observations, the corresponding seco precursors 236, 252, 256, 260 and 264 exhibited cytotoxic activity indistinguishable from the cyclopropane containing agents.

DNA Alkylation Selectivity, Efficiency, and Relative Rates

The DNA alkylation properties of the agents were examined within four 150 base-pair segments of duplex DNA for which comparative results are available for related agents. Four clones of phage M13mp10 were selected for study and contain the SV40 nucleosomal DNA inserts w794 (nucleotide no. 5238-138) and its complement w836 (nucleotide no. 5189-91) and c988 (nucleotide no. 4359-4210) and its complement c820 (nucleotide no. 4201-4356). The alkylation site identification and the assessment of the relative selectivity among the available sites were obtained by thermally-induced strand cleavage of the singly 5'end-labeled duplex DNA after exposure to the agents. Following treatment of the end-labeled duplex DNA with a range of agent concentrations, the unbound agent was removed by EtOH precipitation of the DNA. Redissolution of the DNA in aqueous buffer, thermolysis (100° C., 30 minutes) to induce strand cleavage at the sites of DNA alkylation, denaturing high resolution polyacrylamide gel electrophoresis (PAGE) adjacent to Sanger dideoxynucleotide sequencing standards, and autoradiography led to identification of the DNA cleavage and alkylation sites. The full details of this procedure have been disclosed and discussed elsewhere (10). The DNA alkylation reaction selectivities observed under the incubation conditions of 25° C. (24 hours) for the agents detailed herein have proven identical to the alkylation selectivities observed with shorter or extended reaction periods or when the reactions were conducted at different temperatures (37 or 4° C., 0.5–7 days). As discussed below, the rates and efficiencies but not final relative efficiencies of DNA alkylation were altered by changing the reaction temperatures.

DNA Alkylation Properties of the Natural Enantiomers of MCBI-TMI (254), MCBI-indole$_2$ (258), MCBI-CDPI$_1$ (262) and MCBI-CDPI$_2$ (266)

Figure 17:
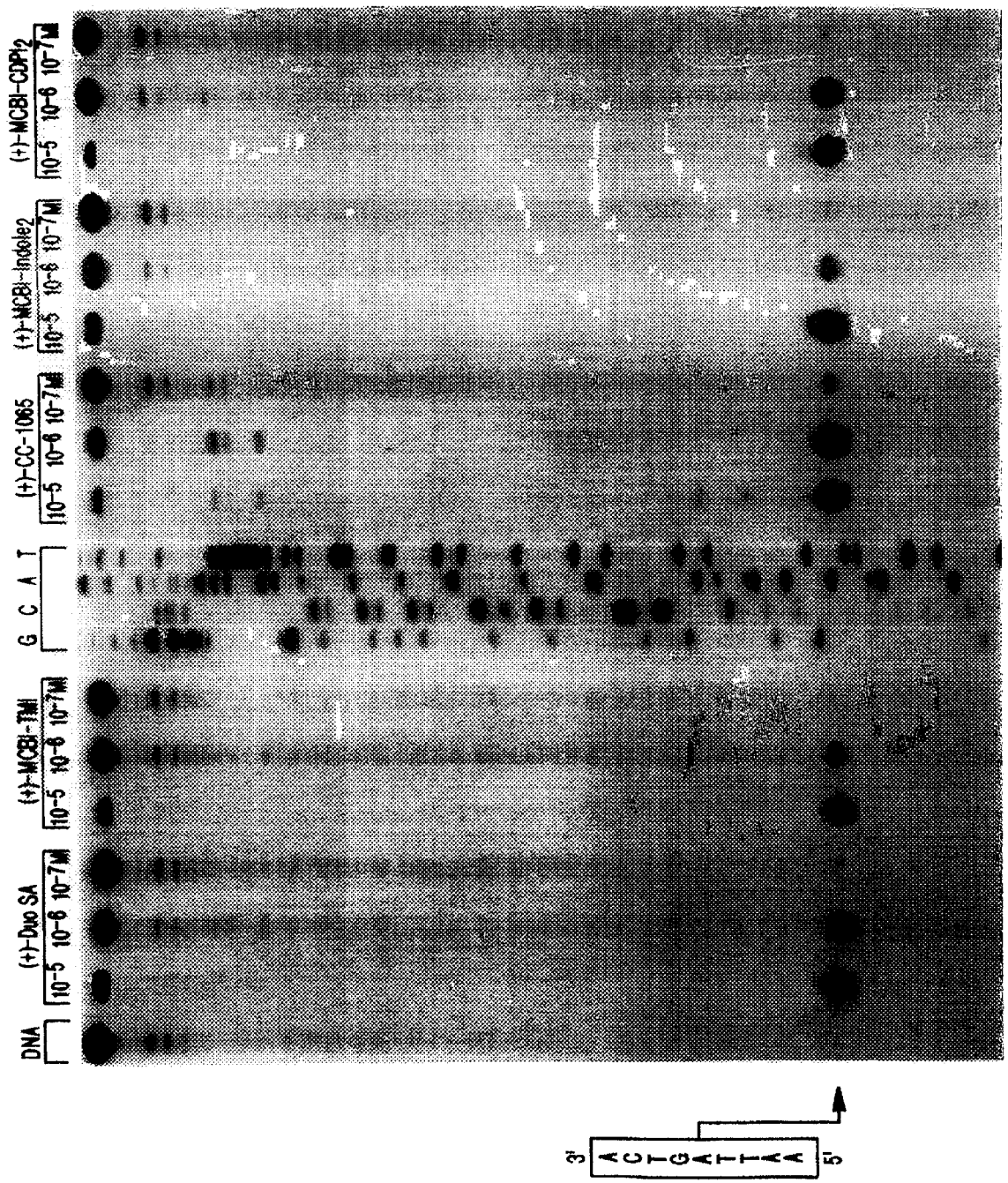
FIG. 17 illustrates thermally-induced strand cleavage of double-stranded DNA (SV40 DNA fragment, 144 bp, nucleotide no. 5238-138, clone w794) after 24 hours incubation of agent-DNA at 25° C. followed by removal of unbound agent and 30 minutes incubation at 100° C; 8% denaturing PAGE and autoradiography. Lane 1, control DNA; lanes 2–4, (+)-duocarmycin SA (2, $1 \times 10^{-5}$ to $1 \times 10^{-7}$ M); lanes 5–7, (+)-MCBI-TMI (254, $1 \times 10^{-5}$ to $1 \times 10^{-7}$ M); lanes 8–11, Sanger G, C, A and T reactions; lanes 12–14, (+)-CC-1065 (1, $1 \times 10^{-5}$ to $1 \times 10^{-7}$ M); lanes 15–17, (+)-MCBI-indole$_2$ (258, $1 \times 10^{-5}$ to $1 \times 10^{-7}$ M); lanes 18–20, (+)-MCBI-CDPI$_2$ (266, $1 \times 10^{-5}$ to $1 \times 10^{-7}$ M).

A comparison of the DNA alkylation by the natural enantiomers of 254, 258, 262, and 266 alongside the natural products (+)-duocarmycin SA (2) and (+)-CC-1065 (1) within w794 DNA is illustrated in FIG. 17 and is representative of the full set of comparisons that have been made with the agents. In the comparisons, (+)-duocarmycin SA (2) and (+)-MCBI-TMI (254) were indistinguishable and the two agents exhibited the same selectivity and efficiency of DNA alkylation. This is illustrated nicely within w794 DNA in FIG. 17 where the two agents detectably alkylate the same high affinity site of 5'-AATTA at $10^{-6}$ to $10^{-7}$ M, both alkylate the three additional minor sites to comparable extent only at higher concentrations, and both exhibit the same extent of alkylation throughout the concentration range examined. This is exactly analogous to the observations made in our prior comparisons of duocarmycin SA (2) and CBI-TMI (Boger et al. *J. Am. Chem. Soc.* 1994, 116, 7996).

Similarly, (+)-MCBI-CDPI$_2$ (266) and )+)-CC-1065 (1) proved essentially indistinguishable in our comparisons. This is illustrated nicely in FIG. 17 with w794 DNA where the two agents detectably alkylate the high affinity site of 5'-AATTA at $10^{-7}$ M, both alkylate the additional minor sites to comparable extents at higher agent concentrations, and both exhibit the same extent of alkylation throughout the concentration range examined. This is most apparent in the comparison of the amount of unreacted DNA present at each of the reaction concentrations. Similarly, (+)-MCBI-indole$_2$ (258) alkylates DNA detectable at $10^{-7}$ Molar.

Although this is not as pronounced within w794 where only subtle distinctions in the alkylation selectivity are observed with the relative efficiencies of alkylation of minor sites, the distinctions between duocarmycin SA/MCBI-TMI versus CC-1065/MCBI-CDPI$_2$ are more evident in the additional segments of DNA examined. In these comparisons the smaller agents including duocarmycin SA, MCBI-TMI, and MCBI-CDPI$_1$ exhibit a clear 3.5 base-pair AT-rich alkylation selectivity while the longer agents including CC-1065 and MCBI-CCPI$_2$ more strongly prefer the larger 5 base-pair AT-rich alkylation sites. These observations are analogous to those made in the direct comparisons of the CBI-based agents with CC-1065 or the duocarmycins (Boger et al. *J. Am. Chem. Soc.* 1994, 116, 7996) and no features which distinguish the behavior of the natural enantiomers of the MCBI- and CBI-based agents were detected. These alkylation selectivities have been documented and described in detail elsewhere (Boger et al. *J. Am. Chem. Soc.* 1994, 116, 7996) and each alkylation site detected was adenine followed by two 5' A or T bases in a three base-pair site that follows the following preference: 5'-AAA>5'-TTA>5'-TAA>5'-ATA. For the shorter agents MCBI-TMI and MCBI-CDPI$_1$, there was also a strong preference but no absolute requirement for the fourth 5' base to be A or T versus G or C and this preference distinguished many of the high versus low affinity sites (e.g., 5'-AAAA). For the longer agent MCBI-CDPI$_2$, not only was there a stronger preference for the fourth base to be A or T but that preference extended to include a fifth 5' A or T base (e.g., 5'-AAAAA). Thus, like the preceding agents, the MCBI-based agents exhibited AT-rich adenine N3 alkylation selectivities that start at the 3' adenine N3alkylation site with agent binding in the minor groove in the 3'–5' direction covering 3.5 or 5 base pairs.

Figure 15A:
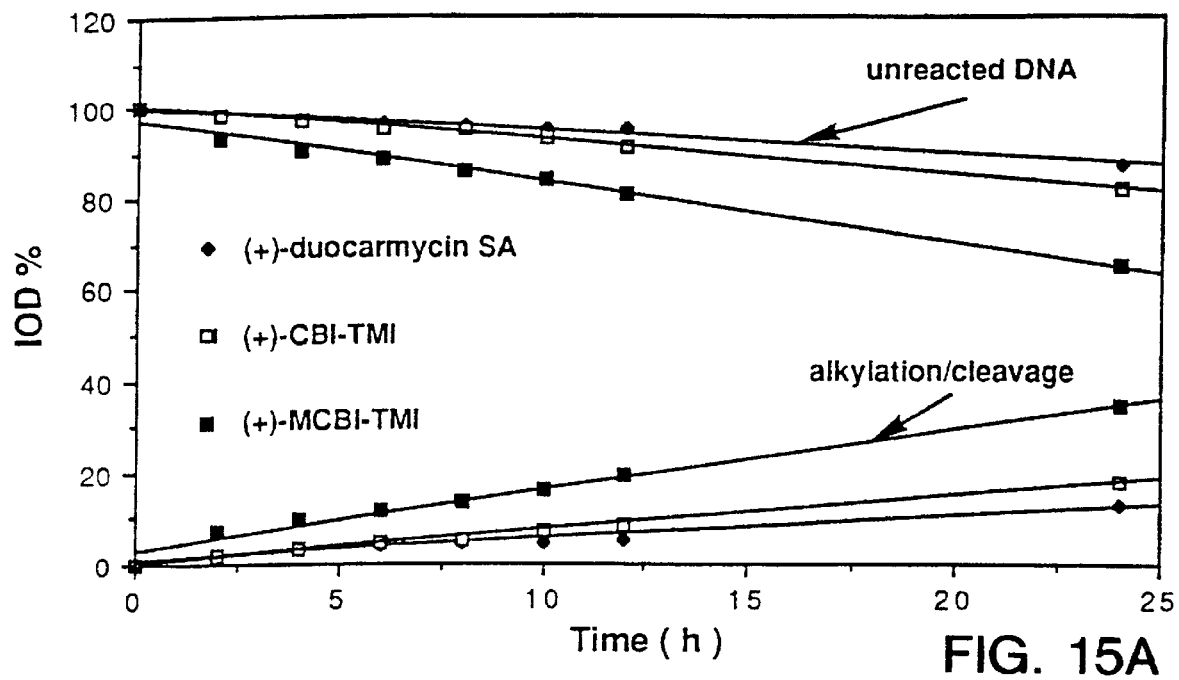
FIG. 15 illustrates a plot of percent integrated optical density (% IOD) versus time established through autoradiography of 5'-$^{32}$P and labeled DNA and used to monitor the relative rate of w794 alkylation at the 5'-AATTA high-affinity site for 1, 254, 258, (+)-CBI-TMI and (+)-DSA-indole$_2$.
Figure 15B:
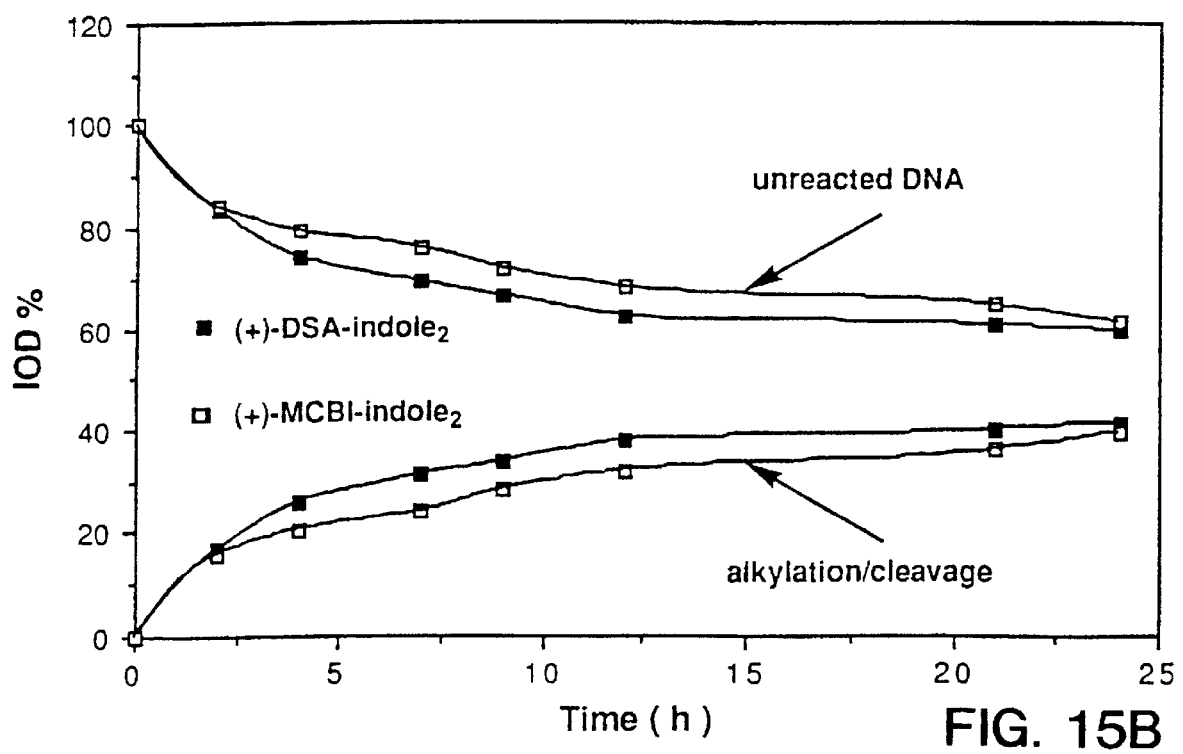

Analogous to the relative rates of DNA alkylation established for (+)-duocarmycin SA (1) and (+)-CBI-TMI at the w794 high affinity site, 5'-AATTA, the relative rates of DNA alkylation for (+)-duocarmycin SA (1), (+)-CBI-TMI, and (+)-MCBI-TMI (254) were measured (4° C., 0–48 hours, $10^{-6}$ M agent concentration) and the three agents proved nearly indistinguishable. (+)-MCBI-TMI was found to alkylate the 5'-AATTA high affinity site kinetically faster at 4° C. than duocarmycin SA or CBI-TMI although the distinctions are quite small: k(254):k(CBI-TMI):k(2)=1.8:1.0:0.9 (FIG. 15). Similar relative rates were observed in the prior comparisons of duocarmycin SA and CBI-TMI and the three agents are so close that accurate distinctions between CBI-TMI and MCBI-TMI are not readily achievable. At 25° C., the distinctions are even more difficult to observe and the three agents are essentially indistinguishable consistent with the relative reactivities of the agents established in the chemical solvolysis studies.

Representative of this difficulty in detecting distinguishing relative rates for the three classes of agents, a similar rate comparison of (+)-DSA-indole$_2$ and (+)-MCBI-indole$_2$ (258) conducted at 25° C. (0–24 hours) and at $10^{-6}$ M agent concentration revealed an essentially indistinguishable rate: k(DSA-indole$_2$)/k(MCBI-indole)$_{2=}$1.05 (FIG. 15). Importantly, these two comparisons suggest that little if any experimentally distinguishable differences in the relative rates of DNA alkylation is observed with the natural enantiomers of the DSA-, CBI-, or MCBI-based agents. In sharp contrast, all three kinetically alkylate DNA much faster than the corresponding CPI-based agent (10–50x) where the distinctions are much more pronounced and easily experimentally distinguished.

DNA Alkylation Properties of the Unnatural Enantiomers of MCBI-TMI (254), MCBI-indole$_2$ (258), MCBI-CDPI$_1$ (262), and MCBI-CDPI$_2$ (266)

Figure 13:
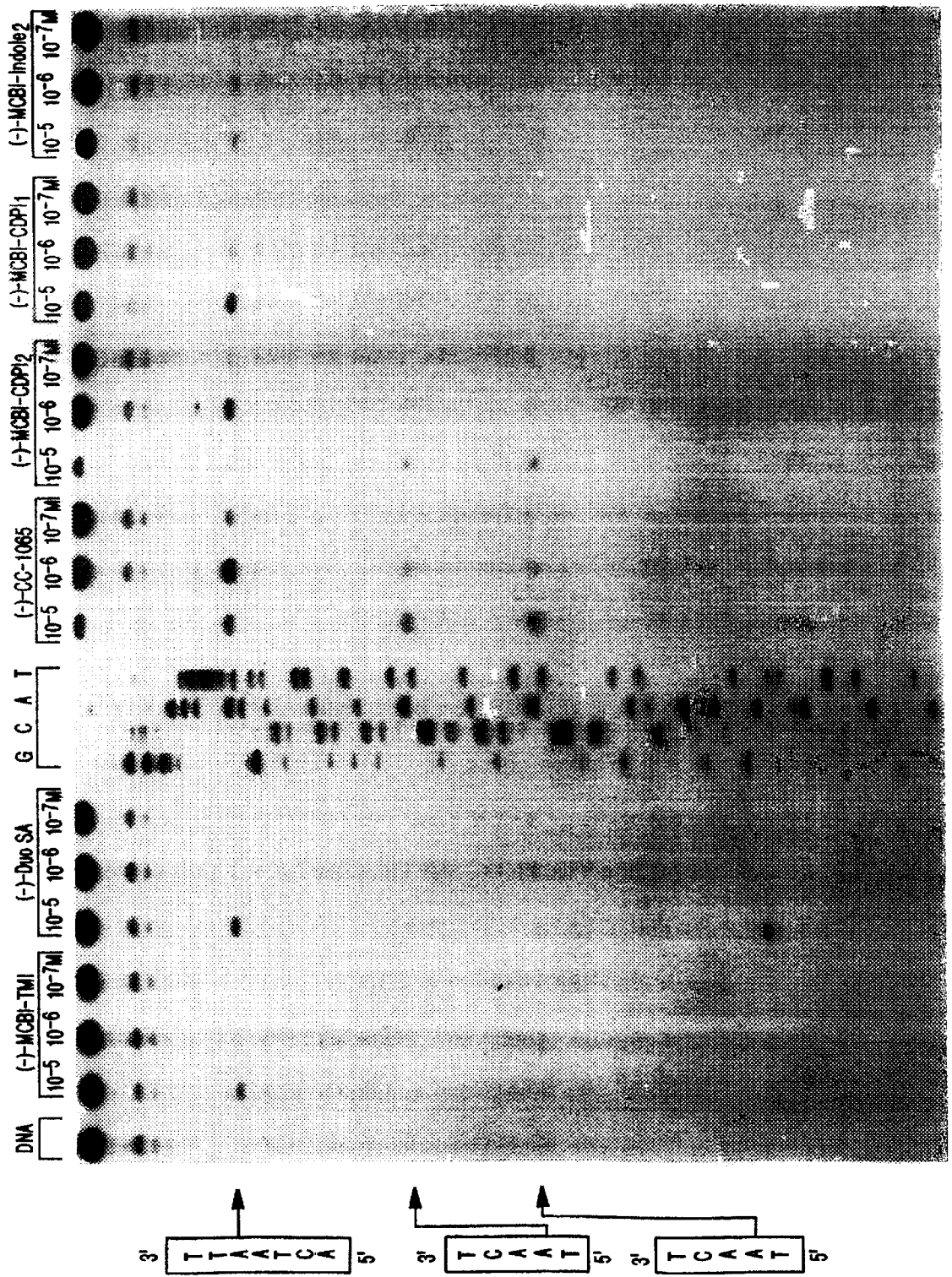
FIG. 13 illustrates thermally-induced strand cleavage of double-stranded DNA (SV40 DNA fragment, 144 bp, nucleotide no. 5238-138, clone w794) after 72 hours incubation of agent-DNA at 37° C. followed by removal of unbound agent and 30 minutes incubation at 100° C.; 8% denaturing PAGE and autoradiography. Lane 1, control DNA; lanes 2–4, (−)-MCBI-TMI (254, $1 \times 10^{-5}$ to $1 \times 10^{-7}$ M); lanes 5–7, (−)-duocarmycin SA (2, $1 \times 10^{-5}$ to $1 \times 10^{-7}$ M); lanes 8–11, Sanger G, C, A and T reactions; lanes 12–14, (−)-CC-1065 (1, $1 \times 10^{-5}$ to $1 \times 10^{-7}$ M); lanes 15–17, (−)-MCBI-CDPI$_2$ (266, $1 \times 10^{-5}$ to $1 \times 10^{-7}$ M); lanes 18–20, (−)-MCBI-CDPI$_1$ (262, $1 \times 10^{-5}$ to $1 \times 10^{-7}$ M); lanes 21–23 (−)-MCBI-indole$_2$ (258, $1 \times 10^{-5}$ to $1 \times 10^{-7}$ M).
Figure 14A:
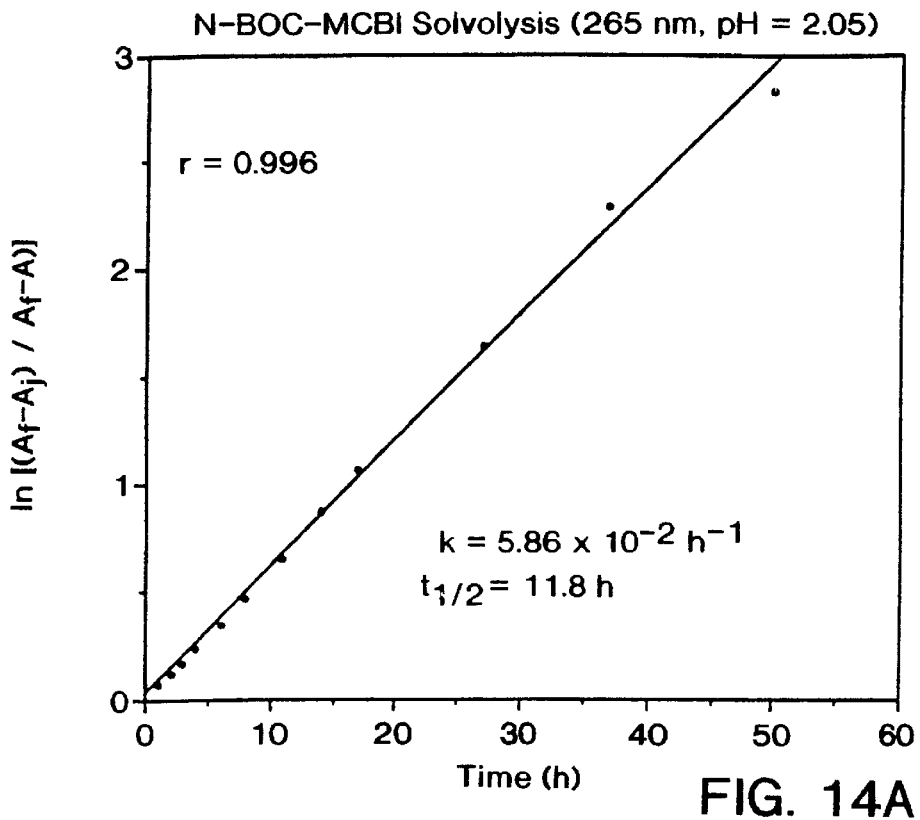
FIG. 14 illustrates the linear relationship between $\ln[(A_f-A_i)/(A_f-A)]$; solvolysis study (UV spectra) of N-BOC-MCBI (238, top) and MCBI (240, bottom) in 50% CH$_3$OH-aqueous buffer (pH 3.0, 4:1:20 (v/v/v) 0.1 M citric acid, 0.2 M Na$_2$HPO$_4$, and H$_2$O, respectively). The spectra were recorded at regular intervals and only a few are shown for clarity. Top: 1, 0 hour; 2, 4 hours; 3, 27 hours; 4, 70 hours; 5, 105 hours; 6, 177 hours. Bottom: 1, 0 hour; 2, 4 hours; 3, 27 hours; 4, 70 hours; 5, 177 hours; 6, 752 hours.
Figure 14B:
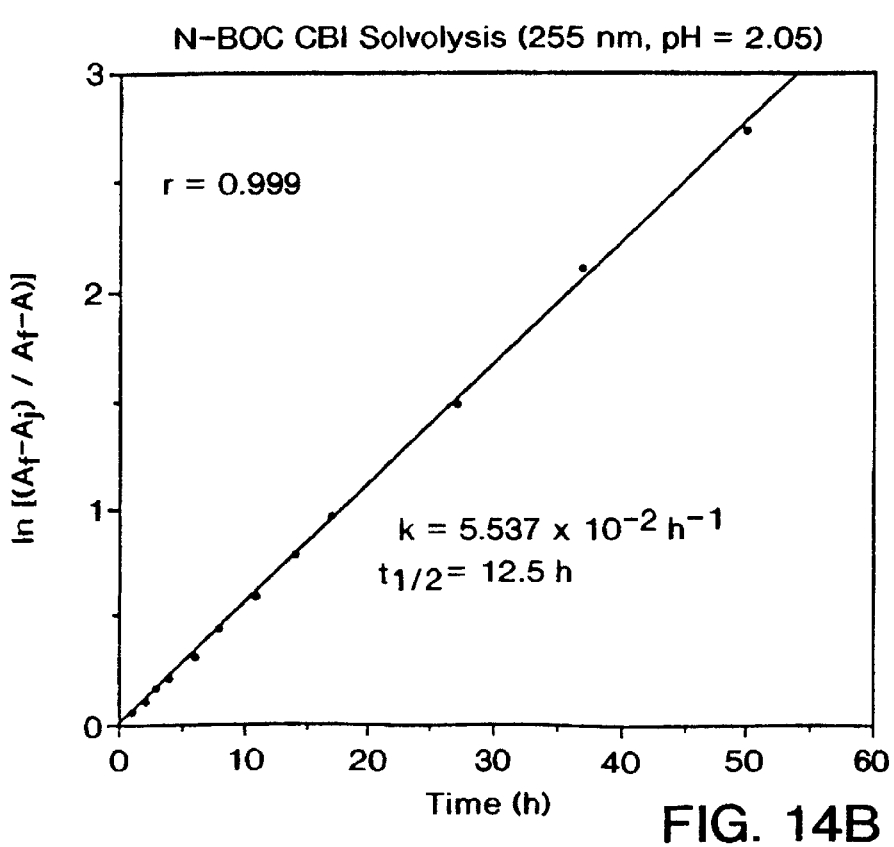

A representative comparison of the DNA alkylation by the unnatural enantiomers of the MCBI-based agents alongside the unnatural enantiomers of duocarmycin SA (2) and CC-1065 (1) with the same w794 segment of DNA is illustrated in FIG. 13. Several important observations analogous to those made in our prior studies with the CBI-based agents are also observed with the MCBI-based agents. First, the unnatural enantiomer DNA alkylation is considerably slower and the results shown in FIG. 13 for the unnatural enantiomers were obtained with incubation at 37° C. (72 hours) versus incubation at 25° C. (24 hours, FIG. 17) for the natural enantiomers. Even with the more vigorous reaction conditions, the extent of alkylation by the unnatural enantiomers is lower requiring higher agent concentrations to detect. Even longer reaction times at 37° C. were required to achieve the same efficiency of alkylation that was observed with the natural enantiomers at 25° C. (24 hours). This distinguishing difference in the rate of DNA alkylation was most prominent with the small agents MCBI-TMI (254) and duocarmycin SA (2), readily perceptible but less prominent with the intermediate sized agents MCBI-CDPI$_1$ (262) and MCBI-indole$_2$ (258), and perceptible but even less prominent with the largest agents MCBI-CDPI$_2$ (266) and CC-1065 (1). This trend is similar to that observed in the relative cytotoxic potency of pairs of enantiomers. (+)-MCBI-TMI is 50xmore potent than the corresponding unnatural enantiomer while the natural enantiomers of the larger agents (258, 262, 266) are only 1–3x more potent with the enantiomers of 262 and 266 being essentially indistinguishable. This is illustrated nicely in the w794 DNA alkylation in FIG. 13 where MCBI-TMI and duocarmycin SA exhibit detectable alkylation at $10^{-5}$ M, while that of MCBI-CDPI$_3$, MCBI-indole$_2$ and MCBI-CDPI$_2$ are detectable at $10^{-6}$ to $10^{-7}$ M. Under the conditions of 25° C. (24 hours), the natural enantiomers all alkylate w794 detectably at $10^{-6}$ to $10^{-7}$ M (FIG. 17).

The DNA alkylation selectivity and efficiency of (-)-MCBI-TMI (254) and ent-(-)-duocarmycin SA (2) were nearly indistinguishable with the latter agent being slightly more effective. This observation is analogous to that made in our prior comparisons of (-)-CBI-TMI and ent-(-)-duocarmycin SA (2) except the distinction was larger (10x). Similarly, (-)-MCBI-CDPI$_2$ (266) and ent-(-)-CC-1065 were nearly indistinguishable as were (-)-MCBI-indole$_2$ and (-)-MCBI-CDPI$_1$. This is perhaps most apparent in comparing the relative extent of labeled DNA consumed at $10^{-5}$ M in FIG. 13. Again, no distinctions in the DNA alkylation selectivity of the unnatural enantiomers of MCBI-based agents and the agents described previously were perceptible. Each of the alkylation sites proved to be adenine which was flanked on both sides nearly always by an A or T base and the preference for this three base AT-rich site was 5'-AAA>5'-TAA>5'-AAT>5'-TAT. For the shorter agents, there was a strong preference for the second 3' base to be A or T (e.g., 5'-AAAA) which for the larger agents extended to the third 3' base as well (e.g., 5'-AAAAA). Thus, each alkylation site for the unnatural enantiomers proved consistent with adenine N$_3$ alkylation with agent binding in the minor groove in the reverse 5'–3' direction across a 3.5 or 5 base-pair AT-rich site surrounding the alkylation site. This is analogous to the natural enantiomer alkylation selectivity except that it extends in the reverse 5'–3' direction in the minor groove and, because of the diastereomeric nature of the adducts, is offset by one base-pair relative to the natural enantiomers.

DNA Alkylation Properties of (+)- and ent-(-)-N-BOC-MCBI

Figure 16:
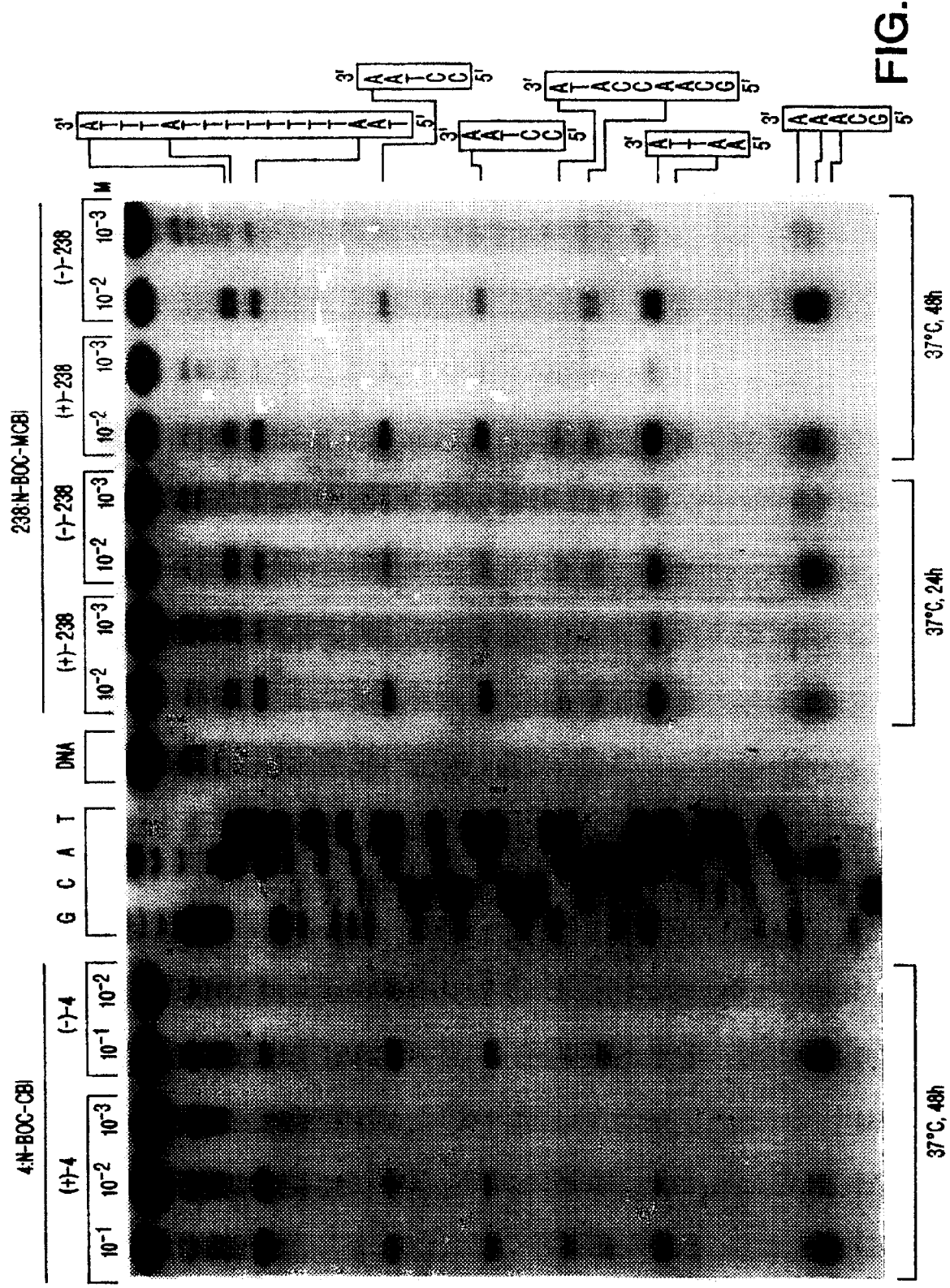
FIG. 16 illustrates thermally induced strand cleavage of 5' end labeled DNA (SV40 DNA fragment, 144 bp, nucleotide no. 5238-138, clone w794). As indicated, the DNA-agent incubation was conducted at 37° C. for 24 or 48 hours, followed by removal of unbound agent and 30 minutes incubation at 100° C.; 8% denaturing PAGE and autoradiography.

A representative comparison of the DNA alkylation properties of both enantiomers of N-BOC-MCBI (238) within the same w794 DNA segment is illustrated in FIG. 16. No substantial distinctions between N-BOC-CBI (4) and N-BOC-MCBI (238) were detected except that the relative efficiency of DNA alkylation by the unnatural enantiomer of 238 was essentially indistinguishable from that of its natural enantiomer under the assay conditions and significantly better than the unnatural enantiomer of N-BOC-CBI: (+)-N-BOC-CBI/ent-(-)-N-BOC-CBI (5–10x)[34] versus (+)-N-BOC-MCBI/ent-(-)-N-BOC-MCBI (1–2x). The two enantiomers of 238 alkylated DNA much less efficiently than 257–266 ($10^{4x}$; FIG. 6) providing detectable alkylation at $10^{-2}$ to $10^{-3}$ M (37° C., 24–48 hours), much less selectively than 257–266 exhibiting a two base-pair AT-rich alkylation selectivity (5'-AA>5'-TA), and did so with alkylation of the same sites. This unusual behavior of the two enantiomers alkylating the same sites is analogous to past observations made with 4–9. It is a natural consequence of the reversed binding orientations of the two enantiomers and the diastereomeric relationship of the two adducts which result in the two enantiomers covering the exact same binding site surrounding the alkylated adenine. N-BOC-MCBI (238) conforms nicely to these past observations and models.

Enantiomer Distinctions

Prior studies have suggested an attractive explanation for the confusing behavior of enantiomeric pairs of agents which we have proposed may be attributed to a single structural feature—the degree of steric bulk surrounding the CPI/DSA C7 or CBI/MCBI C8 center in the alkylation subunit for which the unnatural enantiomers are especially sensitive. The enantiomer differences have proven distinguishable with simple derivatives of the alkylation subunits themselves (i.e., N-BOC-MCBI), are most prominent with the dimer based agents (i.e., MCBI-TMI), and are less prominent or not readily distinguishable with the larger trimer or tetramer based agents (i.e., MCBI-CDPI$_2$). In general, less distinction in the biological potency and relative DNA alkylation efficiency was observed with the CI and duocarmycin SA enantiomeric pairs, both which lack substituents or steric bulk at this position.

Moreover, the distinctions among the enantiomeric CI-based agents which lack the pyrrole ring altogether are small and less pronounced than those observed with the DSA-based agents (DSA>CI). In contrast, the CPI-, CBI-, and DA-based agents exhibit more pronounced distinctions (CPI>DA>CBI) following an order that reflects the relative steric differences. Consistent with these observations, the MCBI-TMI enantiomers were found to exhibit analogous but smaller distinctions than those observed with CBI-TMI (FIG. 12). This distinguishing behavior of the unnatural enantiomers is derived from a pronounced steric interaction of the CPI/DSA C7 or CBI/MCBI C8 center with the 5' base adjacent to the adenine N3 alkylation site present in the unnatural enantiomeric 5'–3' binding model.

Importantly, the only major distinction between the CBI- and MCBI-based agents was observed with the unnatural enantiomers where the MCBI derivatives were found to be 4–40× more potent in cytotoxic assays and more efficient at alkylating DNA than the corresponding CBI derivative. In addition, the unnatural enantiomers of MCBI-CDPI$_1$, MCBI-indole$_2$, and MCBI-CDPI$_2$ were nearly equipotent with the corresponding natural enantiomers in the cytotoxic assays. Although such behavior has been observed with (+)-CC-1065/ent-(−)-CC-1065 and some of the more advanced analogs (e.g., CPI-CDPI$_2$), the unnatural enantiomers of the indole$_2$ and CDPI$_1$ derivatives of various alkylation subunits have been less potent than the natural enantiomers. The comparisons of the cytotoxic properties of the unnatural enantiomers of the CBI derivatives detailed in FIG. 10 versus those of MCBI-indole$_2$, MCBI-CDPI$_1$, and MCBI-CDPI$_2$ are representative of such past and present observations. In contrast to the CBI-based agents where the unnatural enantiomers were 8–400× less potent than the natural enantiomers with only the two enantiomers of CBI-CDPI$_2$ exhibiting comparable potencies, both enantiomers of MCBI-indole$_2$, MCBI-CDPI$_1$, and MCBI-CDPI$_2$ were comparable in cytotoxic potency (1–3×) and the distinctions essentially absent with the tighter binding CDPI$_1$ and CDPI$_2$ derivatives.

These observations may be important in distinguishing the origin of the biological potencies of this class of reversible DNA alkylating agents. Two proposals have been advanced in which the biological potencies have been suggested to be related to either the rate of DNA alkylation or to the thermodynamic stability of the adducts and the resulting relative efficiency of DNA alkylation. Clearly not only do the rates of DNA alkylation between the various natural enantiomers of the MCBI derivatives vary widely, but the rates of DNA alkylation between the enantiomeric pairs vary to an even larger extent. The near equivalent cytotoxic potencies among the full set of MCBI natural enantiomers and the comparable cytotoxic potency of most of the unnatural MCBI enantiomers is inconsistent with the proposal that the rates of DNA alkylation can be related to cytotoxic potency but is entirely consistent with the proposal that the thermodynamic stability and resulting efficiency of DNA alkylation may be directly related. The unnatural enantiomers form inherently less stable adducts and are more readily reversed than the corresponding natural enantiomers. For the natural enantiomers, a single DNA alkylation subunit is sufficient to provide functionally stable adducts (i.e., TMI, CDPI$_1$) and provides fully potent agents capable of efficient DNA alkylation. For the unnatural enantiomers, the full biological potency and efficient DNA alkylation have generally been achieved only with the agents containing two large DNA binding subunits (i.e., CDPI$_2$).

Intermediate potencies are seen with the smaller agents which diminish as their size and noncovalent binding affinity decreases. Representative of such a trend is the behavior of the unnatural enantiomers of the CBI-based agents (FIG. 10). The unnatural enantiomers of MCBI follow this same trend except that they behave more like the natural enantiomers in that they are more potent and reach a plateau of cytotoxic potency with some of the simpler, single DNA binding subunit derivatives. To us, this has suggested that the C7 methoxy substituent on the alkylation subunit of the MCBI unnatural enantiomers provides sufficient additional noncovalent binding stabilization to enhance the apparent efficiency or stability of the unnatural enantiomer DNA alkylation. Consistent with this proposal, even the N-BOC-MCBI and the MCBI-TMI enantiomers were found to exhibit less distinction than those of CBI-TMI. While this impact of a single methoxy group may appear speculative, similar potentiating effects of a single methoxy substituent within the TMI subunit of (+)-duocarmycin SA have been observed. Similarly, the duocarmycin SA C6 methoxycarbonyl group may be contributing to the potentiation of the DSA unnatural enantiomers.

This interpretation and relationship of the cytotoxic potency with the efficiency of DNA alkylation and stability of the adducts is especially attractive since it is consistent with the direct relationship between cytotoxic potency and functional stability observed with derivatives of 4–9. Consistent with the interpretation that it is not the rate of DNA alkylation and functional reactivity that enhances cytotoxic potency but rather the net efficiency and relative stability of the DNA alkylation process, it is the chemically more stable agents which may most effectively reach their intracellular biological target that exhibit the more potent cytotoxic activity provided they are sufficiently reactive to alkylate DNA with the formation of functionally stable adducts.

SUMMARY

A short and efficient 12–13 step (27–30% overall) synthesis of MCBI and its immediate precursors is detailed and constitutes the first substituted CBI derivative disclosed. Its evaluation permitted the first assessment of the electronic effect of substituents on the chemical and functional reactivity of the agents and the impact this may have on their biological properties. A study of the solvolysis reactivity of N-BOC-MCBI indicated that the introduction of the strong electron-donating C7 methoxy group accelerates the rate of solvolysis by only 1.2–1.06×. This remarkably small effect indicates that protonation of the C4 carbonyl is not the rate determining step of solvolysis or acid-catalyzed nucleophilic addition and further supports the proposal that the cyclopropane ring opening reaction requires the presence and assistance of a nucleophile (S$_N$2 mechanism). No doubt this contributes to the DNA alkylation selectivity and suggests that the positioning of an accessible nucleophile (adenine N3) and not C4 carbonyl protonation or Lewis acid complexation is the rate determining step controlling the sequence selectivity of DNA alkylation. This exceptionally small electronic effect on the solvolysis rate had no impact on the solvolysis regioselectivity and stereoelectronically-controlled nucleophilic addition to the least substituted carbon of the activated cyclopropane was observed exclusively. For the natural enantiomers, this very small electronic effect on functional reactivity had little or no perceptible effect on their DNA alkylation selectivity, efficiency, and relative rates or on their biological properties when compared to the corresponding CBI-based agent. Perceptible effects of the C7 methoxy group on the unnatural enantiomers were detected and they proved to be 4–40× more effective than the corresponding CBI-based unnatural enantiomers and comparable in cytotoxic potency with the corresponding MCBI natural enantiomer. This effect on the unnatural enantiomers is most consistently rationalized not by a C7 methoxy substituent effect on functional reactivity, but rather through introduction of additional stabilizing noncovalent interactions which increase DNA alkylation efficiency and further stabilize an inherently reversible DNA alkylation reaction.

Synthetic Methods

Preparation of Ethyl 1-Hydroxy-6-methoxy-naphthalene-3-carboxylate (210) as Illustrated in FIG. 3

Method A

A solution of t-Potassium-butoxide (21.0 g, 0.19 mol, 2 equiv) in t-Butanol (81 mL) was added to a solution of m-anisaldehyde 200 (10.8 mL, 11.8 g, 0.087 mol) from Aldrich company and diethyl succinate (40.2 mL, 0.242 mol, 3 equiv) and the mixture was warmed at reflux for 45 minutes. Additional diethyl succinate (40.2 mL, 0.242 mol, 3 equiv) and t-Potassium-butoxide (21.0 g, 0.19 mol, 2 equiv) in t-Butanol (81 mL) were added and the mixture was warmed at reflux for an additional 45 minutes. The mixture was cooled, acidified with the addition of 25% aqueous HCl and extracted with Diethyl ether (3×15 mL). The organic layer was extracted with 5% aqueous $Na_2CO_3$ (6×40 mL). The resulting aqueous phase was acidified with the addition of 25% aqueous HCl and reextracted with Diethyl ether (3×30 mL). The combined organic layer was dried ($Na_2SO_4$) and concentrated under reduced pressure providing an oily product that proved to be a 2:1 mixture of the isomeric half-esters 202 (15.0 g, 23.2 g theoretical, 74%).

The mixture of 202 (15.0 g, 64 mmol) was treated with $Ac_2O$ (320 mL) and NaOAc (5.25 g, 64 mmol, 1.0 equiv) and warmed at reflux for 5 hours. The solvent was removed under reduced pressure and the residue was treated with 15% aqueous $Na_2CO_3$ (100 mL) and extracted with Ethylacetate (3×30 mL). The organic layer was dried ($Na_2SO_4$) and concentrated in vacuo. Without further purification, the dark brown oil was dissolved in Ethanol (100 mL) and treated with $K_2CO_3$ (10 g, 72.4 mmol). The mixture was warmed at reflux for 18 hours before being cooled, concentrated, diluted with $H_2O$ (40 mL), acidified to pH 6 with the addition of 10% aqueous HCl, and extracted with Ethylacetate (3×20 mL). The organic layer was dried ($Na_2SO_4$) and concentrated under reduced pressure. Flash chromatography (5×20 cm $SiO_2$, 10–30% Ethylacetate-hexane gradient elution) afforded 210 (8.90 g, 21.4 g theoretical, 42% for 3 steps) as a white solid: mp 168° C. (hexane, colorless plates); $^1$H NMR (CDCl$_3$, 400 MHz) δ8.15 (d, J=8.8 Hz, 1H, C8-H), 8.10 (s, 1H, C4-H), 7.38 (s, 1H, C2-H), 7.23 (dd, J=3.2, 8.8 Hz, 1H, C7-H), 7.20 (d, J=3.2 Hz, 1H, C5-H), 4.40 (q, J=8.0 Hz, 2H), 3.90 (s, 3H, OCH$_3$), 1.40 (t, J=8.0 Hz, 3H); $^{13}$C NMR (CDCl$_3$, 100 MHz) δ166.1, 157.5, 152.9, 134.4, 127.9, 123.3, 121.7, 119.8, 118.6, 106.0, 104.8, 60.0, 54.5, 13.7; IR (KBr) $\mu_{max}$ 385, 1683, 1608, 1397, 1283, 1225, 1028, 878, 833, 768 cm$^{-1}$; FABHRMS (NBA) m/e 246.0885 (M$^+$, $C_{14}H_{14}O_4$ requires 246.0892). Anal. Calcd for $C_{14}H_{14}O_4$: C, 68.28; H, 5.73. Found: C, 68.22; H, 5.77.

Variable amounts of 206 were also isolated. For 206: mp 88–89° C.; $^1$H NMR (CDCl$_3$, 400 MHz) δ9.32 (s, 1H, OH), 8.03 (d, J=1.5 Hz, 1H, C4-H), 7.50 (d, J=8.2 Hz, 1H, C5-H), 7.43 (d, J=1.5 Hz, 1H, C2-H), 7.37 (t, J=8.2 Hz, 1H, C6-H), 6.86 (d, J=7.6 Hz, 1H, C7-H), 4.39 (q, J=7.8 Hz, 2H), 4.09 (s, 3H, OCH$_3$), 1.39 (t, J=7.8 Hz, 3H); $^{13}$C NMR (CDCl$_3$, 100 MHz) μ166.5, 155.9, 154.6, 135.8, 129.5, 126.4, 123.1, 121.5, 117.1, 109.6, 106.0, 61.1, 56.2, 14.3; IR (film) $\mu_{max}$ 3404, 3056, 2980, 1718, 1711, 1611, 1583, 1468, 1450, 1380, 1290, 1220, 1126, 1087 cm$^{-1}$; FABHRMS (NBA-NaI) m/e 269.0786 (M$^+$+Na, $C_{14}H_{14}O_4$ requires 269.0790). Anal. Calcd for $C_{14}H_{14}O_4$: C, 68.28; H, 5.73. Found: C, 68.23; H, 5.64.

Method B, From 214

A 9:1 mixture of $CF_3CO_2H$—$H_2O$ (50 mL) at 0° C. was added to 214 (3.10 g, 9.68 mmol) and the reaction mixture was warmed to 25° C. and stirred for 2 hours. The reaction mixture was concentrated in vacuo and two separate 50 mL volumes of toluene were sequentially added and removed under reduced pressure to provide 202 (2.50 g, 2.56 g theoretical, 98%) as a colorless oil.

A mixture of 202 (2.50 g, 9.46 mmol) and NaOAc (0.750 g, 9.50 mmol) in 50 mL of $Ac_2O$ was warmed at 70° C. for 10 hours. The volatiles were removed in vacuo and a solution of the crude product and $K_2CO_3$ (1.38 g, 10.0 mmol) in 35 mL of Ethanol was warmed at reflux for 4 hours. The reaction mixture was cooled to 0° C., acidified with the addition of 1M HCl (pH 6), and extracted with Diethyl ether (4×30 mL). The organic layers were combined, washed with saturated aqueous NaCl (1×10 mL), dried ($Na_2SO_4$), and concentrated under reduced pressure. Centrifugal thin-layer chromatography ($SiO_2$, 4 mm chromatotron plate, 5–20% Ethylacetate-hexane gradient elution) provided 210 (1.79 g, 2.33 g theoretical, 76%) and 206 (0.22 g, 9%) as white crystalline solids.

The following table summarizes the results of related efforts to convert 202 derived from 214 to 210:

| conditions | reaction time (h) | ratio 210:206 | % 210 isolated |
| --- | --- | --- | --- |
| $Ac_2O$-NaOAc, 160° C.[a] | 1 | 5:1 | 61 |
| $Ac_2O$-NaOAc, 70° C.[a] | 10 | 8:1 | 76 |
| TFAA-NaOAc, 40° C.[a] | 30 | 9:1 | 57 |
| (COCl$_2$); AlCl$_3$ 0° C. | 1 | 11:1 | 38 |
| (COCl$_2$); FeCl$_3$ 0° C. | 2 | 10:1 | 46 |
| (COCl$_2$); SnCl$_4$ 0° C. | 2 | 11:1 | 54 |

[a]Subsequent treatment with $K_2CO_3$-Ethanol

Preparation of tert-Butyl E-3-Ethoxy-carbonyl-4-(3-methoxyphenyl)-3-butenoate (214)

Compound 214 as Illustrated in FIG. 3

A suspension of NaH (0.64 g, 16 mmol, 60% in oil) in 25 mL of tetrahydrofuran was added to a solution of 212 (5.00 g, 14.8 mmol) see Owten et. al. *Synth. Commun.* 1993, 23, 2119, in 40 mL of tetrahydrofuran at 0° C. and the reaction mixture was warmed to 25° C. and stirred for 10 hours. The solution was cooled to 0° C., 200 (2.00 g, 14.8 mmol) from Aldrich chemical company in 25 mL of tetrahydrofuran was added, and the mixture was warmed to 25° C. and stirred for 10 hours. A majority of the tetrahydrofuran was removed under reduced pressure and saturated aqueous NaHCO$_3$ (20 mL) was added. The aqueous layer was extracted with Ethylacetate (4×30 mL), and the organic layers were combined, washed with saturated aqueous NaCl, dried ($Na_2SO_4$), and concentrated in vacuo. Chromatography ($SiO_2$, 6×15 cm, 5–10% Ethylacetate-hexane gradient elution) provided 214 (3.65 g, 4.74 g theoretical, 77%) as a colorless oil as a single isomer by $^1$H NMR (>20:1): $^1$H NMR ($CDCl_3$, 400 MHz) $\mu$7.80 (s, 1H, C2'-H), 7.28 (t, J=7.8 Hz, 1H, C5'-H), 6.92–6.86 (m, 3H, C4-H, C4'-H, C6'-H), 4.26 (q, J=7.1 Hz, 2H), 3.79 (s, 3H, $OCH_3$), 3.44 (s, 2H, C2-$H_2$), 1.44 (s, 9H, $C(CH_3)_3$), 1.31 (t, J=7.1 Hz, 3H); $^{13}$C NMR ($CDCl_3$, 100 MHz) $\mu$170.3, 167.5, 159.6, 141.1, 136.5, 129.5, 127.0, 121.4, 114.7, 114.0, 81.0, 61.0, 55.2, 35.0, 28.0, 14.2; IR (film) 2978, 2933, 1726, 1708, 1578, 1368, 1278, 1194, 1155, 1096 $cm^{-1}$; FABHRMS (NBA) m/e 321.1716 ($M^+$+H, $C_{18}H_{24}O_5$ requires 321.1702).

Preparation of Ethyl 1-Benzyloxy-6-methoxy-naphthalene-3-carboxylate (216) as Illustrated in FIG. 4

Compound 216

A solution of 210 (900 mg, 3.65 mmol) in anhydrous dimethylformamide (12.5 mL) under $N_2$ was treated with anhydrous $K_2CO_3$ (700 mg, 5.1 mmol, 1.4 equiv), benzyl bromide (0.51 mL, 4.3 mmol, 1.2 equiv) and $Bu_4NI$ (0.7 mg). The mixture was stirred at 25° C. for 5 hours before it was concentrated under reduced pressure. Chromatography ($SiO_2$, 2–5% Ethylacetate-hexane gradient elution) provided 216 (1.20 g, 1.23 g theoretical, 98%) as a colorless semi-solid: $^1$H NMR ($CDCl_3$, 400 MHz) $\mu$8.20 (d, J=9.6 Hz, 1H, C8-H), 8.10 (s, 1H, C4-H), 7.53 (d, J=8.0 Hz, 2H), 7.40 (t, J=8.0 Hz, 1H), 7.37 (d, J=2.4 Hz, 1H, C5-H), 7.34 (m, 2H), 7.19 (dd, J=2.4, 9.6 Hz, 1H, C7-H), 7.18 (s, 1H, C2-H), 5.20 (s, 2H, $CH_2C_6H_5$), 4.40 (q, J=8.0 Hz, 2H), 3.90 (s, 3H, $OCH_3$), 1.40 (t, J=8.0 Hz, 3H); $^{13}$C NMR ($CDCl_3$, 100 MHz) $\mu$166.9, 158.6, 154.7, 136.8, 134.9, 128.6, 128.56, 128.3, 128.2, 127.6, 123.9, 122.6, 106.9, 102.4, 119.9, 106.9, 102.4, 71.1, 61.1, 55.2, 14.3; IR (film) $\mu_{max}$ 2978, 1715, 1603, 1455, 1406, 1366, 1345, 1286, 1237, 1149, 1097, 1029 $cm^{31\ 1}$; FABHRMS (NBA-CsI) m/e 469.0422 ($M^+$+Cs, $C_{21}H_{20}O_4$ requires 469.0416). Anal. Calcd for $C_{21}H_{20}O_4$: C, 74.98; H, 5.99. Found: C, 75.21; H, 5.91.

Preparation of 1-Benzyloxy-6-methoxy-naphthalene-3-carboxylic Acid (218) as Illustrated in FIG. 4

Compound 218

A solution of 216 (2.49 g, 7.40 mmol) in tetrahydrofuran-$CH_3OH$—$H_2O$ (4:1:1, 50 mL) was treated with LiOH—$H_2O$ (930 mg, 22.2 mmol, 3 equiv). The suspension was stirred at 23° C. for 18 hours before $H_2O$ (20 mL) was added. The solution was acidified with the addition of 10% aqueous HCl and the white precipitate was collected. Crystallization from Ethanol afforded 218 (2.17 g, 2.28 g theoretical, 95%, typically 95–98%) as white needles: mp 185° C. (Ethanol, white needles); $^1$H NMR (dimethylsulfoxide-$d_6$, 400 MHz) $\mu$8.15 (d, J=9.6 Hz, 1H, C8-H), 8.10 (s, 1H, C4-H), 7.57 (d, J=9.6 Hz, 2H), 7.50 (d, J=2.0 Hz, 1H, C5-H), 7.43 (t, J=9.6 Hz, 1H), 7.37 (d, J=9.6 Hz, 2H), 7.34 (s, 1H, C2-H), 7.27 (dd, J=2.0, 9.6 Hz, 1H, C7-H), 5.30 (s, 2H, $CH_2C_6H_5$), 3.90 (s, 3H, $OCH_3$); $^{13}$C NMR (DIMETHYLSULFOXIDE-$d_6$, 100 MHz) $\mu$167.6, 158.2, 154.1, 136.9, 134.8, 129.0, 128.5, 127.9, 127.5, 123.3, 122.2, 122.1, 120.0, 107.6, 102.6, 69.5, 55.4; IR (KBr) $\delta_{max}$ 2932, 2647, 2543, 1685, 1629, 1420, 1296, 1201, 1030, 891, 768, 638 $cm^{-1}$; FABHRMS (NBA) m/e 308.1040 ($M^+$, $C_{19}H_{16}O_4$ requires 308.1049).

Anal. Calcd for $C_{19}H_{16}O_4$: C, 74.01; H, 5.23. Found: C, 73.86; H, 5.33

Preparation of N-(tert-Butyloxycarbonyl)-1-(benzyloxy)-6-methoxy-3-naphthylamine (220) as Illustrated in FIG. 4

Compound 220

A solution of 218 (1.20 g, 3.91 mmol) in t-Butanol (75 mL) was treated sequentially with diphenylphosphoryl azide (DPPA, 1.29 g, 4.69 mmol, 1.2 equiv., sec Shioiri et al, *J. Am. Chem Soc.* 1972, 94, 6203) and Triethylamine (0.67 mL, 4.69 mmol, 1.2 equiv) and the mixture was stirred at reflux for 10 hours. The mixture was cooled and concentrated in vacuo. Centrifugal thin-layer chromatography ($SiO_2$, 4 mm chromatotron plate, 5–10% Ethylacetate-hexane gradient elution) afforded 220 (1.01 g, 1.48 g theoretical, 68%, typically 60–69%) as a white solid: mp 138° C. (hexane, white needles); $^1$H NMR ($CDCl_3$, 400 MHz) $\mu$8.10 (d, J=9.6 Hz, 1H, C8-H), 7.50 (d, J=8.8 Hz, 2H), 7.40 (m, 2H), 7.35 (m, 2H), 6.98 (d, J=1.9 Hz, 1H, C4-H), 6.95 (dd, J=2.5, 9.6 Hz, 1H, C7-H), 6.86 (d, J=1.9 Hz, 1H, C2-H), 6.65 (s, 1H, NH), 5.20 (s, 2H, $CH_2C_6H_5$), 3.80 (s, 3H, $OCH_3$), 1.50 (s, 9H, $C(CH_3)_3$); $^{13}$C NMR ($CDCl_3$, 100 MHz) $\mu$158.7, 155.3, 152.7, 136.9, 136.3, 129.8, 128.6, 127.9, 127.4, 123.7, 117.6, 116.0, 106.7, 105.3, 97.2, 80.6, 70.1, 55.2, 28.4; IR (KBr) $\mu_{max}$ 3323, 2978, 1698, 1591, 1549, 1422, 1346, 1228, 1148, 1024, 945, 869, 820, 756, 701 $cm^{-1}$; FABHRMS (NBA-CsI) m/e 512.0846 ($M^+$+Cs, $C_{23}H_{25}NO_4$ requires 512.0838). Anal. Calcd for $C_{23}H_{25}NO_4$: C, 72.80; H, 6.64; N, 3.69. Found: C, 72.42; H, 6.77; N, 3.92.

Preparation of N-(tert-Butyloxycarbonyl)-4-benzyloxy-1-bromo-7-methoxy-2-naphthylamine (222) as Illustrated in FIG. 4

Compound 222

A solution of 220 (620 mg, 1.63 mmol) in tetrahydrofuran (35 mL) under $N_2$ was cooled to −78° C. and treated with a solution of tetrahydrofuran (2 mL) containing 10 $\mu$L of concentrated $H_2SO_4$. After 5 minutes, a solution of NBS (320 mg, 1.80 mmol, 1.1 equiv) in tetrahydrofuran (10 mL) was added and the mixture was stirred at −78° C. for 2 hours. The mixture was diluted with Diethyl ether (50 mL) and washed with saturated aqueous $NaHCO_3$ (2×10 mL) and saturated aqueous NaCl (20 mL), dried ($Na_2SO_4$) and concentrated in vacuo. Centrifugal thin-layer chromatography ($SiO_2$, 4 mm chromatotron plate, 5–10% Ethylacetate-hexane) afforded 222 (720 mg, 747 mg theoretical, 96%, typically 90–98%) as a white solid: mp: 125–127° C. (hexane, white solid); $^1$H NMR ($CDCl_3$, 400 MHz) $\mu$8.10 (d, J=9.2 Hz, 1H, C5-H), 7.98 (s, 1H, C3-H), 7.55 (d, J=7.2 Hz, 2H), 7.40 (m, 5H), 7.02 (dd, J=2.4, 9.2 Hz, 1H, C6-H), 5.20 (s, 2H, $CH_2C_6H_5$), 3.90 (s, 3H, $OCH_3$), 1.50 (s, 9H, $C(CH_3)_3$); the 2D $^1$H-$^1$H NOESY NMR ($CDCl_3$, 400 MHz) displayed a diagnostic NOE crosspeak for C3-H/$CH_2C_6H_5$; $^{13}$C NMR ($CDCl_3$, 100 MHz) $\mu$159.8, 154.7, 152.5, 136.6, 135.6, 133.9, 128.6, 128.1, 128.0, 127.8, 124.5, 118.3, 116.3, 105.1, 97.6, 81.2, 70.3, 55.3, 28.6; IR (KBr) $\mu_{max}$ 3409, 2977, 1733, 1623, 1506, 1367, 1222, 1153, 1030, 989, 882, 829, 753 $cm^{-1}$; FABHRMS (NBA) m/e 457.0880 ($M^+$, $C_{23}H_{24}BrNO_4$ requires 457.0889).

Preparation of 2-[N-(tert-Butyloxycarbonyl)-N-(3-methyl-2-buten-1-yl)]amino-4-benzyloxy-1-bromo-7-methoxynaphthalene (224) as Illustrated in FIG. 4

Compound 224

A suspension of NaH (44 mg, 0.92 mmol, 50% in oil, 1.3 equiv) in dimethylformamide (4 mL) at 24° C. under Ar was treated with 222 (315 mg, 0.71 mmol) and the reaction mixture was stirred for 30 minutes. The mixture was cooled at 0° C. and 4-bromo-2-methyl-2-butene (0.25 mL, 2.1 mmol, 3 equiv) was added slowly. The mixture was allowed to warm to 24°0 C. and was stirred for 8 hours before being poured onto $H_2O$ (15 mL). The mixture was extracted with Ethylacetate (3×10 mL) and the combined organic extracts were washed with $H_2O$ (10 mL), saturated aqueous NaCl (5 mL), dried ($Na_2SO_4$) and concentrated in vacuo. Chromatography ($SiO_2$, 5–7% Ethylacetate-hexane gradient elution) afforded 224 (357 mg, 374 mg theoretical, 95%) as an off-white solid: mp 108–109° C. (hexane, white solid); $^1H$ NMR ($CDCl_3$, 400 MHz) mixture of amide rotamers, for the major rotamer $\mu$8.10 (d, J=9.2 Hz, 1H, C5-H), 7.56 (d, J=2.4 Hz, 1H, C8-H), 7.47 (d, J=7.2 Hz, 2H), 7.38 (m, 3H), 7.13 (dd, J=2.4, 9.2 Hz, 1H, C6-H), 6.55 (s, 1H, C3-H), 5.30 (t, J=6.8 Hz, 1H, CH=C), 5.20 (d, J=11.7 Hz, 1H, CHHC$_6$H$_5$), 5.14 (d, J=11.7 Hz, 1H, CHHC$_6$H$_5$), 4.42 (dd, J=6.1, 15.0 Hz, 1H, NCHH), 4.05–3.90 (m, 1H, NCHH), 3.96 (s, 3H, OCH$_3$), 1.53 (s, 9H, C(CH$_3$)$_3$), 1.30 (s, 6H, two CH$_3$); $^{13}C$ NMR (CDCl$_3$, 100 MHz) $\mu$159.4, 154.2, 153.9, 139.6, 136.5, 135.7, 134.3, 128.6, 128.1, 127.5, 127.2, 124.2, 119.8, 118.2, 113.6, 106.3, 106.2, 80.0, 70.3, 55.4, 46.4, 28.2, 25.7, 17.6; IR (KBr) $\mu_{max}$ 2929, 1680, 1623, 1452, 1414, 1381, 1223, 1151, 1035, 972, 916, 841, 700 cm$^{-1}$; FABHRMS (NBA) m/e 526.1569 (M$^+$+H, C$_{28}$H$_{32}$BrNO$_4$ requires 526.1593). Anal. Calcd for C$_{28}$H$_{32}$BrNO$_4$: C, 63.88; H, 6.13; N, 2.66. Found: C, 63.66; H, 6.15; N, 2.68.

Preparation of 2-[N-(tert-Butyloxycarbonyl)-N-(formylmethyl)]amino-4-benzyloxy-1-bromo-7-methoxynaphthalene (226) as Illustrated in FIG. 4

Compound 226

A solution of 224 (755 mg, 1.43 mmol) in 20% CH$_3$OH—CH$_2$Cl$_2$ (45 mL) was cooled to −78° C. and was treated with a stream of 3% O$_3$/O$_2$ (100 L/h) for 2.9 minutes. The reaction mixture was immediately quenched with the addition of 4.5 mL (61 mmol, 43 equiv) of Me$_2$S. The reaction mixture was stirred at −78° C. for 5 minutes and at 24° C. for 6 hours before the solvent was removed in vacuo. Centrifugal thin-layer chromatography (SiO$_2$, 2 mm chromatotron plate, 10–20% Ethylacetate-hexane gradient elution) afforded 226 (580 mg, 718 mg theoretical, 81%) as a white solid: mp 170° C. (dec, Ethylacetate-hexane, white solid); $^1$H NMR (CDCl$_3$, 400 MHz) two amide rotamers, $\mu$9.70 and 9.75 (two s, 1H, CHO), 8.20 and 8.10 (two d, J=9.2 Hz, 1H, C5-H), 7.50 (d, J=2.4 Hz, 1H, C8-H), 7.45 (d, J=7.6 Hz, 2H), 7.30 (m, 3H), 7.10 (dd, J=2.4, 9.2 Hz, 1H, C6-H), 6.80 and 6.75 (two s, 1H, C3-H), 5.21–5.06 (m, 2H, OCH$_2$C$_6$H$_5$), 4.58 and 4.46 (two d, J=18.8 Hz, 1H, CHHCHO), 3.90 (m, 1H, CHHCHO), 3.91 and 3.89 (two s, 3H, OCH$_3$), 1.50 and 1.30 (two s, 9H); $^{13}$C NMR (CDCl$_3$, 100 MHz) $\mu$ major rotamer 198.1, 159.7, 154.4, 139.5, 136.3, 134.3, 128.7, 128.2, 127.8, 127.4, 124.4, 118.6, 112.7, 106.3, 105.5, 105.2, 81.3, 70.4, 59.2, 55.4, 28.2; IR (KBr) $\mu_{max}$ 2977, 2911, 2850, 2835, 1735, 1695, 1624, 1599, 1458, 1417, 1365, 1225, 1155, 1107, 1026, 839, 741 cm$^{-1}$; FABHRMS (NBA) m/e 499.0969 (M$^+$, C$_{25}$H$_{26}$BrNO$_5$ requires 499.0994). Anal. Calcd for C$_{25}$H$_{26}$BrNO$_5$: C, 60.01; H, 5.24; N, 2.80. Found: C, 59.81; H, 5.19; N, 3.07.

Preparation of 2-[N-(tert-Butyl-oxycarbonyl)-N-(3-tetrahydro-pyranyloxy-2-propen-1-yl)]-amino-4-benzyloxy-1-bromo-7-methox-ynaphthalene (228) as Illustrated in FIG. 4

Compound 228

A suspension of triphenyl[(2-tetra-hydro-pyranyl-oxy)methyl]-phosphonium chloride (371 mg, 0.90 mmol, 3.0 equiv., see Schlude, H. *Tetrahedron* 1975, 31, 89) in 2 mL of tetrahydrofuran at −78° C. was treated dropwise with n-BuLi (0.727 mL, 1.18 M in hexane, 0.86 mmol, 2.86 equiv). The reaction mixture was stirred at −78° C. for 5 minutes and allowed to warm to 24° C. over 10 minutes. The mixture was recooled to −78° C. and 23 (154 mg, 0.30 mmol) in tetrahydrofuran (1 mL) was added dropwise followed by HMPA (1.2 mL, 24 equiv). The reaction mixture was stirred 20 minutes at −78° C. and 5 hours at 24° C. before being quenched with the addition of phosphate buffer (51 mL, pH 7.4). The mixture was extracted with Ethylacetate (3×20 mL) and the combined organic phase was dried (Na$_2$SO$_4$) and concentrated in vacuo. Chromatography (SiO$_2$, 5–30% Ethylacetate-hexane gradient elution containing 2% Triethylamine) afforded 228 (154 mg, 175 mg theoretical, 88%) as an oil and as a mixture of E- and Z-olefin isomers: $^1$H NMR (CDCl$_3$, 400 MHz) E- and Z-isomers and amide rotamers $\mu$8.10 (m, 1H, C5-H), 7.5–7.3 (m, 7H), 7.00 (m, 1H, C6-H), 6.7–6.5 (m, 1H, CH=CH), 6.3–6.0 (m, 1H, CH=CH), 5.2–5.0 (m, 2H, CH$_2$C$_6$H$_5$), 4.8–4.2 (m, 3H), 3.98–2.70 (m, 5H, OCH$_3$ and OCH$_2$CH$_2$), 1.6–1.3 (m, 15H); IR (film) $\mu_{max}$ 2947, 2871, 1704, 1622, 1597, 1453, 1415, 1367, 1227, 1161, 1035, 960, 901, 841, 742, 697, 651 cm$^{-1}$; FABHRMS (NBA-CsI) m/e 730.0800 (M$^+$+Cs, C$_{31}$H$_{36}$BrNO$_6$ requires 730.0780). Anal. Calcd for C$_{31}$H$_{36}$BrNO$_6$: C, 62.21; H, 6.06; N, 2.34. Found: C, 62.42; H, 6.27; N, 2.45.

Preparation of 5-(Benzyloxy)-3-(tert-butyloxycarbonyl(-8-methoxy-1-(tertrahydropyranyloxymethyl)-1,2-dihydro-3H-benz[e]indole (230) as Illustrated in FIG. 4

Compound 230

A solution of 228 (950 mg, 1.59 mmol) and AIBN (4.4 mg, 0.32 mmol, 0.2 equiv) in C$_6$H$_6$ (60 mL) at 24° C. under Ar was treated with Bu$_3$SnH (925 mg, 3.18 mmol, 2 equiv) and the reaction mixture was warmed at reflux for 2 hours. The reaction mixture was cooled and the solvent was removed in vacuo. Centrifugal thin-layer chromatography (SiO$_2$, 4 mm chromatotron plate, 5–10% Ethylacetate-hexane gradient elution containing 2% Triethylamine) afforded 230 (785 mg, 826 mg theoretical, 95%, typically 95–98%) as a pale yellow oil: $^1$H NMR (CDCl$_3$, 400 MHz) $\mu$8.10 (d, J=9.2 Hz, 1H, C6-H), 7.65 (br s, 1H, C4-H), 7.45–7.25 (m, 5H), 6.95 (d, J=2.4 Hz, 1H, C9-H), 6.88 (dd, J=2.4, 9.2 Hz, 1H, C7-H), 5.20 (br s, 2H, CH$_2$C$_6$H$_5$), 4.60 and 4.50 (two br s and m, 1H, OCHCH$_2$), 4.20–3.20 (m, 10H), 1.90–1.50 (m, 15H); $^{13}$C NMR (CDCl$_3$, 100 MHz) $\mu$158.7, 155.6, 153.0, 137.0, 132.0, 128.51, 128.45, 127.9, 127.5, 125.0, 117.4, 115.0, 101.4, 100.1, 98.3, 94.6, 70.1, 68.9, 62.7, 60.4, 55.3, 52.9, 30.6, 28.5, 25.9, 19.7, 14.2; IR (Film) $\mu_{max}$ 2942, 1700, 1623, 1451, 1405, 1368, 1228, 1141, 1029, 986, 907, 834, 737 cm$^{-1}$; FABHRMS (NBA) m/e 519.2597 (M$^+$+Cs, C$_{31}$H$_{37}$NO$_6$ requires 519.2621).

Preparation of 5-(Benzyloxy)-3-(tert-butyloxycarbonyl)-1-(hydroxymethyl)-8-methoxy-1,2-dihydro-3H-benz[e]indole (232) as Illustrated in FIG. 4

Compound 232

A solution of 230 (207 mg, 0.40 mmol) in CH$_3$OH (6.5 mL) was treated with Amberlyst 15 (12.5 mg) and the reaction mixture was warmed at 45° C. for 6 hours. The resin was removed by filtration and the solvent was concentrated in vacuo. Chromatography (SiO$_2$, 20–40% Ethylacetate-hexane gradient elution) afforded 232 (171 mg, 172.5 mg theoretical, 99%) as a colorless solid: mp 158–160° C. (hexane, colorless solid); $^1$H NMR (CDCl$_3$, 400 MHz) $\mu$8.10 (d, J=9.6 Hz, 1H, C6-H), 7.80 (br s, 1H, C4-H), 7.51 (d, J=7.2 Hz, 2H), 7.40 (t, J=7.1 Hz, 2H), 7.36–7.32 (m, 1H), 6.96 (br s, 1H, C9-H), 6.95 (dd, J=11.0, 8.4 Hz, 1H, C7-H), 5.20 (br s, 2H, CH$_2$C$_6$H$_5$), 4.17 (d, J=11.0 Hz, 1H, C2-H), 4.10 (dd, J=11.0, 8.4 Hz, 1H, C2-H), 3.93–3.90 (m, 1H, C1-H), 3.89 (s, 3H, OCH$_3$), 3.70 (m, 2H, CH$_2$OH), 1.50 (s, 9H, C(CH$_3$)$_3$); $^{13}$C NMR (CDCl$_3$, 100 MHz) $\mu$158.9, 155.0, 151.0, 128.5, 127.9, 127.6, 125.2, 114.9, 101.2, 94.6, 70.2, 64.6, 55.3, 52.4, 41.2, 28.5; IR (KBr) $\mu_{max}$ 3405, 1691, 1625, 1588, 1478, 1449, 1407, 1366, 1227, 1140, 1028 cm$^{-1}$; FABHRMS (NBA-CsI) m/e 568.1101 (M$^+$+Cs, C$_{26}$H$_{29}$NO$_5$ requires 568.1100).

Preparation of 5-(Benzyloxy)-3-(tert-butyloxycarbonyl)-1-(chloromethyl)-8-methoxy-1,2-dihydro-3H-benz[e]indole (234) as Illustrated in FIG. 4

Compound 234

A solution of 232 (112 mg, 0.25 mmol) and Ph$_3$P (135 mg, 0.50 mmol, 2 equiv) in CH$_2$Cl$_2$ (0.9 mL) at 24° C. under Ar was treated with CCl$_4$ (0.15 mL, 1.5 mmol, 6 equiv), and the reaction mixture was stirred for 20 hours at 24° C. Chromatography (SiO$_2$, 10% Ethylacetate-hexane) afforded 234 (113 mg, 113 mg theoretical, 100%) as a white solid: mp 148–150° C. (hexane, white solid); $^1$H NMR (CDCl$_3$, 400 MHz) $\mu$8.10 (d, J=9.2 Hz, 1H, C6-H), 7.70 (br s, 1H, C4-H), 7.50 (d, J=6.4 Hz, 2H), 7.40–7.35 (m, 3H), 6.97 (dd, J=2.4, 9.2 Hz, 1H, C7-H), 6.86 (d, J=2.4 Hz, 1H, C9-H), 5.20 (s, 2H, CH$_2$C$_6$H$_5$), 4.22 (m, 1H, C2-H), 4.10 (t, J=9.8 Hz, 1H, C2-H), 3.92–3.86 (m, 2H, CHHCl, C1-H), 3.91 (s, 3H, OCH$_3$), 3.40 (t, J=11.4 Hz, 1H, CHHCl), 1.58 (s, 9H, C(CH$_3$)$_3$); $^{13}$C NMR (CDCl$_3$, 100 MHz) $\mu$159.2, 156.3, 153.0, 137.0, 131.0, 128.5, 128.0, 127.6, 125.4, 118.0, 114.9, 100.8 94.5, 70.2, 55.4, 53.0, 46.2, 28.5; IR (KBr) $\mu_{max}$ 2971, 1699, 1626, 1456, 1405, 1367, 1334, 1144, 1029, 958, 907 cm$^{-1}$; FABHRMS (NBA) m/e 453.1710 (M$^+$, C$_{26}$H$_{28}$ClNO$_4$ requires 453.1706). Anal. Calcd for C$_{26}$H$_{28}$ClNO$_4$: C, 68.79; H, 6.22; N, 3.09. Found: C, 68.70; H, 6.51; N, 2.78.

Preparation of 3-(tert-Butyloxycarbonyl)-1-(chloromethyl)-5-hydroxy-8-methoxy-1,2-dihydro-3H-benz[e]indole (236) as Illustrated in FIG. 4

Compound 236

A mixture of 234 (80 mg, 0.17 mmol), HCO$_2$NH$_4$ (70 mg, 1.11 mmol, 6 equiv), 10% Pd-C (80 mg) in acetone (6 mL) was warmed at reflux for 30 minutes. The catalyst was removed by filtration and the solvent was evaporated under reduced pressure. Centrifugal thin-layer chromatography (SiO$_2$, 40% Ethylacetate-hexane) afforded 236 (61 mg, 64 mg theoretical, 95%, typically 95–100%) as a white solid; $^1$H NMR (CDCl$_3$, 400 MHz) $\mu$8.10 (d, J=9.2 Hz, 1H, C6-H), 7.50 (br s, 1H, C4-H), 6.95 (dd, J=2.4, 9.2 Hz, 1H, C7-H), 6.84 (d, J=2.4 Hz, 1H, C9-H), 6.05 (br s, 1H, OH), 4.22 (m, 1H, C2-H), 4.10 (t, J=11.6 Hz, 1H, C2-H), 3.98–3.80 (m, 2H, CHHCl, C1-H), 3.91 (s, 3H, OCH$_3$), 3.40 (t, J=11.4 Hz, 1H, CHHCl), 1.60 (s, 9H, C(CH$_3$)$_3$); IR (KBr) $\mu_{max}$ 3336, 2929, 1674, 1629, 1595, 1477, 1421, 1374, 1223, 1141, 1029, 822, 713 cm$^{-1}$; FABHRMS (NBA-CsI) m/e 496.0287 (M$^+$+Cs, C$_{19}$H$_{22}$ClNO$_4$ requires 496.0292).

Resolution of 236

The enantiomers of 236 were resolved on a HPLC semi-preparative Diacel Chiralcel OD column (10 $\mu$m, 2×25 cm) using 2% i-PrOH-hexane eluant (5 mL/min). The enantiomers eluted with retention times of 48.03 (unnatural enantiomer) and 41.05 minutes (natural enantiomer, $\mu$=1.17). Natural (1S)-236: [$\mu$]$^3$-42 (c 0.25, CH$_2$Cl$_2$), ent-(1R)-236: [$\mu$]$^3$+41 (c 0.25, CH$_2$Cl$_2$).

Preparation of N-(tert-Butyloxycarbonyl)-7-methoxy-1,2,9,9a-tetrahydrocyclopropa[c]benz[e]indol-4-one (238, N-BOC-MCBI) as Illustrated in FIG. 4

Compound 238

A solution of 236 (1.5 mg, 4.1 $\mu$mol) in tetrahydrofuran-dimethylformamide (3:1, 200 $\mu$L) at 0° C. under N$_2$ was treated with suspension of NaH (0.5 mg, 60% in an oil dispersion, 12 $\mu$mol, 3 equiv). The reaction mixture was allowed to stir at 0° C. and for 30 minutes before the addition of pH 7 phosphate buffer (0.2 M, 250 $\mu$L) and 2 mL of tetrahydrofuran. The organic layer was dried (Na$_2$SO$_4$) and concentrated in vacuo. Chromatography (SiO$_2$, 20–30% Ethylacetate-hexane gradient elution) afforded 238 (1.2 mg, 1.3 mg theoretical, 89%) as a white foam: mp 90–92° C. (hexane-Ethylacetate, colorless prisms); $^1$H NMR (CDCl$_3$, 400 MHz) $\mu$8.10 (d, J=8.7 Hz, 1H, C5-H), 6.90 (dd, J=2.4, 8.7 Hz, 1H, C6-H), 6.70 (br s, 1H, C3-H), 6.25 (d, J=2.4 Hz, 1H, C8-H), 4.10 (m, 2H, C1-H$_2$), 3.80 (s, 3H, OCH$_3$), 2.60 (dt, J=4.1, 7.6 Hz, 1H, C9a-H), 1.56 (s, 9H), 1.43 (t, J=5 Hz, 1H, C9-H), 1.23 (t, J=7.1 Hz, 1H, C9-H); $^{13}$C NMR (C$_6$D$_6$, 100 MHz) $\mu$184.5, 162.6, 157.9, 151.8, 142.6, 129.6, 127.4, 111.9, 109.4, 106.7, 82.4, 54.9, 52.4, 33.2, 28.6, 27.9, 23.1; IR (film) $\mu_{max}$ 2974, 1724, 162, 1599, 1477, 1398, 1370, 1297, 1239, 1162, 1122, 1021 cm$^{-1}$; UV (CH$_3$OH) $\mu_{max}$ 312 ($\mu$=18000), 275 nm ($\mu$=16000); UV (tetrahydrofuran) $\mu_{max}$ 301 ($\mu$=25000), 270 nm ($\mu$=20000); FABHRMS (NBA) m/e 328.1561 (M$^+$+H, C$_{19}$H$_{21}$NO$_4$ requires 328.1549). Natural (+)-238: [$\mu$]$^3$+144 (c 0.043, tetrahydrofuran) ent-(-)-238: [$\mu$]$^3$-142 (c 0.031, tetrahydrofuran).

Preparation of 7-Methoxy-1,2,9,9a-tetrahydrocyclopropa[c]benz[e]indol-4-one (240) as Illustrated in FIG. 4

Compound 240

Phenol 236 (5 mg, 1.37 $\mu$mol) was treated with anhydrous 3N HCl-Ethylacetate (0.4 mL) at 24° C. for 20 minutes. The solvent was removed in vacuo to afford the crude, unstable amine hydrochloride. This residue was treated with 5% aqueous NaHCO$_3$ (0.4 mL) and tetrahydrofuran (0.4 mL) at 24° C. under N$_2$, and the two phase mixture was stirred for 1.5 hours (24° C.). The reaction mixture was extracted with Ethylacetate (3×2 mL) and the combined extracts were washed with H$_2$O (2 mL), dried (Na$_2$SO$_4$) and concentrated in vacuo. Chromatography (SiO$_2$, 10% CH$_3$OH—CH$_2$Cl$_2$) afforded 240 (2.9 mg, 3.1 mg theoretical, 93%) as a tan oil: $^1$H NMR (CDCl$_3$, 400 MHz) $\mu$8.10 (d, J=8.7 Hz, 1H, C5-H), 6.87 (dd, J=2.4, 8.7 Hz, 1H, C6-H), 6.27 (d, J=2.4 Hz, 1H, C8-H), 5.65 (s, 1H, C3-H), 4.80 (br s, 1H, NH), 3.80 (s, 3H, OCH$_3$), 3.79 (dd, J=5.2, 10.2 Hz, 1H, C1-H), 3.63 (d, J=10.2 Hz, 1H, C1-H), 2.78 (dt, J=7.8, 4.6 Hz, 1H, C9a-H), 1.40 (dd, J=4.0, 7.8 Hz, 1H, C9-H), 1.23 (t, J=4.4 Hz, 1H, C9-H); IR (film) $\mu_{max}$ 3384, 2917, 2848 1738, 1611, 1525, 1462, 1361, 1236, 1028 cm$^{-1}$; FABHRMS (NBA) m/e 228.1023 (M$^+$+H, C$_{14}$H$_{13}$NO$_2$ requires 228.1025). Natural (+)–240 : [$\mu$]$^3$ +200 (c 0.04, tetrahydrofuran)ent-(-)-240: [$\mu$]$^3$ –194 (c 0.05 tetrahydrofuran).

Preparation of N-(tert-Butyloxycarbonyl)-4-benzyloxy-1-iodo-7-methoxy-2-naphthylamine (242) as illustrated in FIG. 5

Compound 242

A solution of 220 (985 mg, 2.60 mmol) in 40 mL of a 1:1 mixture of tetrahydrofuran-CH$_3$OH was cooled to −78° C.

and 30 mg of P-toluenesulfonic acid-$H_2O$ in 1 mL of tetrahydrofuran was added. N-Iodosuccinimide (642 mg, 2.90 mmol) in 10 mL of tetrahydrofuran was introduced by cannula over 5 minutes. Upon complete reaction (ca. 3 hours at −78° C.), 10 mL of saturated aqueous $NaCHO_3$ and 50 mL of Diethyl ether were added. The reaction was warmed to 25° C. and solid NaCl was added to saturate the aqueous layer. The organic layer was separated and the aqueous layer was extracted with Diethyl ether (3×10 mL). The organic layers were combined, washed with saturated aqueous $NaHCO_3$ (1×10 mL) and saturated aqueous NaCl (2×10 mL), dried ($Na_2SO_4$), and concentrated. Chromatography ($SiO_2$, 2×4 cm, 20% Ethylacetate-hexane) provided 242 (1.17 g, 1.31 g, theoretical, 89%, typically 85–95%) as a crystalline white solid: mp 139–141° C. (Ethylacetate-hexane, needles); $^1H$ NMR ($CDCl_3$, 400 MHz) $\mu$ 8.12 (d, J=9.1 Hz, 1H, C5-H), 7.90 (s, 1H, C3-H), 7.52 (d, J=7.1 Hz, 2H), 7.41 (t, J=7.6 Hz, 2H), 7.36 (d, J=2.4 Hz, 1H, C8-H), 7.34 (t, J=7.4 Hz, 1H), 7.28 (br s, 1H, NH), 6.99 (dd, J=9.1, 2.4 Hz, 1H, C6-H), 5.24 (s, 2H, $OCH_2Ph$), 3.95 (s, 3H, $OCH_3$), 1.56 (s, 9H, $C(CH_3)_3$); $^{13}C$ NMR ($CDCl_3$, 100 MHz) $\mu$ 160.1, 155.8, 152.7, 138.9, 136.6, 136.4, 128.5, 128.0, 127.8, 124.6, 118.5, 116.3, 110.8, 98.1, 81.1, 79.4, 70.3, 55.3, 18.3; IR (film) $\mu_{max}$ 3387, 2978, 2923, 1730, 1621, 1602, 1572, 1503, 1366, 1230, 1152 $cm^{-1}$; FAB-HRMS (NBA-CsI) m/e 637.9836 ($M^+$+Cs, $C_{23}H_{24}INO_4$ requires 637.9804). Anal. Calcd for $C_{23}H_{24}INO_4$:C, 54.67; H, 4.79; N, 2.77. found: C, 54,61; H, 4.85, N. 2.92.

Preparation of 2-[N-(tert-Butyloxycarbonyl)-N-(2-propenyl)]amino-4-benzyloxy-1-iodo-7-methoxy-2-naphthylamine (246) as illustrated in FIG. 5

Compound 246

A solution of 242 (820 mg, 1.62 mmol) in 25 mL of dimethylformamide cooled to 0° C. was treated with NaH (80 mg, 60% in oil, 2.0 mmol) in several portions over 10 minutes. After 45 minutes, allyl bromide (605 mg, 5 mmol) was added and the reaction mixture was allowed to warm to 25° C. and stirred for 3 hours. The reaction mixture was quenched by addition of saturated aqueous $NaHCO_3$ (15 mL) and the aqueous layer was extracted with Ethylacetate (4×15 mL). The organic layers were combined, washed with $H_2O$ (2×10 mL) and saturated aqueous NaCl (2×10 mL), dried ($Na_2SO_4$), filtered, and concentrated under reduced pressure. Centrifugal thin-layer chromatography ($SiO_2$, 4 mm chromatotron plate, 5–15% Ethylacetate-hexane gradient elution) provided 246 (822 mg, 884 mg theoretical, 93%, typically 90–95%) as a crystalline white solid (mixture of amide rotamers in $CDCl_3$): mp 112–113° C. (Ethylacetate-hexane); $^1H$ NMR ($CDCl_3$, 400 MHz) major rotamer $\mu$ d 8.21 (d, J=9.1 Hz, 1H, C5-H), 7.53 (s, 1H, C8-H), 7.46 (d, J=7.2 Hz, 2H), 7.39 (t, J=7.0 Hz, 2H), 7.33 (t, J=7.2 Hz, 1H), 7.13 (dd, J=9.1, 1.8 Hz, 1H, C6-H), 6.60 (s, 1H, C3-H), 5.97-5.87 (m, 1H, CH=$CH_2$), 5.28-4.98 (m, 4H, $CH_2Ph$, C=$CH_2$), 4.51 (dd, J=15.0, 5.9 Hz, 1H, NCHH), 3.97 (s, 3H, $OCH_3$), 3.81 (dd, J=15.0, 7.2 Hz, 1H, NCHH), 1.30 (s, 9H, $C(CH_3)_3$); $^{13}C$ NMR ($CDCl_3$, 100 MHz) $\mu$ 159.9, 155.1, 153.9, 143.6, 137.0, 136.5, 133.6, 128.6, 128.1, 127.2, 124.4, 120.2, 118.3, 117.9, 111.9, 106.3, 93.9, 80.3, 70.2, 55.4, 52.2, 28.3; IR (film) 3077, 2976, 2923, 1703, 1621, 1594, 1450, 1410, 1367, 1324, 1263, 1226, 1149, 1030 $cm^{-1}$; FABHRMS (NBA-CsI) m/e 678.0089 ($M^{30}$+Cs, $C_{26}H_{28}INO_4$ requires 678.0017). Anal. Calcd for $C_{26}H_{28}INO_4$:C, 57.26; H, 5.17; N, 2.57. Found 57.16; H, 5.25; N, 2.54.

Preparation of 5-(Benzyloxy)-3-(tert-butyloxycarbonyl)-8-methoxy-1-(2',2',6',6'-tetramethyl-piperidinyl-N-oxymethyl)-1,2-dihydro-3H-benz[e]indole (248) as illustrated in FIG. 5

Compound 248

A solution of 246 (720 mg, 1.32 mmol) and Tempo (619 mg, 3.96 mmol) in 45 mL of freshly distilled benzene (Na/benzophenone) under $N_2$ was treated with $Bu_3SnH$ (384 mg, 1.32 mmol). The solution was warmed at 70° C. and three additional equivalents of Tempo (3×206 mg) and $Bu_3SnH$ (4×384 mg) were added sequentially in four portions over the next 45 minutes. After 1 hour, the solution was cooled to 25° C. and the volatiles were removed under pressure. Centrifugal thin-layer chromatography ($SiO_2$, 4 mm chromatotron plate, 0–10% Ethylacetate-hexanes gradient elution) provided 248 (622 mg, 758 mg theoretical, 82%, typically 75–90%) as a white solid: mp 128–130° C. (hexane, white needles); $^1H$ NMR (DIMETHYLSULFOXIDE-$d_6$, 400 MHz) $\mu$ 8.01 (d, J=9.2 Hz, 1H, C6-H), 7.62 (br s, 1H, C4-H), 7.52 (br, s, 2H), 7.42 (t, J=7.2 Hz, 2H), 7.35 (t, J=7.3 Hz, 1H), 7.01 )d, J=2.4 Hz, 1H, C9-H), 6.95 (dd, J=9.2, 2.4 Hz, 1H, C7-H), 5.23 (s, 2H, $OCH_2Ph$), 4.16 (d, J=11.0 Hz, 1H, C2-H), 4.01 (t, J=11.0 Hz, 1H, C2-H), 3.92 (dd, J=8.1, 4.6 Hz, 1H, CHHOR), 3.82 (s, 3H, $OCH_3$), 3.79-3.70 (m, 2H, CHHOR and C1-H), 1.51 (s, 9H, $C(CH_3)_3$), 1.46-1.19 (m, 6H, piperidine-($CH_2$)$_3$—), 1.14 (s, 3H, $CH_3$), 1.02 (s, 3H, $CH_3$), 0.91 (s, 3H, $CH_3$), 0.82 (s, 3H, $CH_3$); $^{13}C$ NMR (dimethylsulfoxide-$d_6$, 100 MHz) $\mu$ 158.7, 155.5, 152.7, 141.5, 137.0, 131.9, 128.5, 127.9, 127.5, 125.0, 117.4, 115.3, 112.8, 100.9, 94.6, 80.4, 70.1, 59.8, 59.7, 55.0, 52.8, 39.6, 39.5, 38.4, 33.2, 32.9, 31.2, 28.5, 20.14, 20.52, 17.0; IR (film) $\mu_{max}$ 2974, 2923, 1697, 1620, 1584, 1471, 1446, 1400, 1359, 1323, 1220, 1169, 1133, 1031 $cm^{-1}$; FABHRMS (NBA-NaI) m/e 597.3288 ($M^+$+Na, $C_{35}N_{46}N_2O_5$ requires 597.3304). Anal. Calcd for $C_{35}H_{46}N_2O_5$: C, 73.13; H, 8.07; N, 4.88. Found: C, 73.30; H, 7.94; N, 4.85.

Preparation of 3-(tert)-Butyloxycarbonyl)-1-(hydroxymethyl)-5-hydroxy-8-methoxy-1,2-dihydro-3H-benz[e]indole (230) as illustrated in FIG. 5

Method B, from 248

Compound 230

A solution of 248 (750 mg, 1.30 mmol) in 30 mL of a 3:1:1 mixture of HOAc-tetrahydrofuran-$H_2O$ was treated with zinc powder (1.05 g, 16 mmol) and the resulting suspension was warmed at 70° C. with vigorous stirring. After 2 hours, the reaction mixture was cooled to 25° C. and the zinc was removed by filtration. The volatiles were removed under reduced pressure and the resulting residue was dissolved in 30 mL of Ethylacetate and filtered. The solution was concentrated and subjected to centrifugal thin-layer chromatography ($SiO_2$, 4 mm chromatotron plate, 15–35% Ethylacetate-hexane gradient elution) to provide 230 (487 mg, 566 mg theoretical, 86%, typically 80–90%) as a white solid identical in all respects to authentic material.

Preparation of seco-MCBI-TMI (252) as illustrated in FIG. 6

Compound 252

A solution of 236 (3.5 mg, 9.6 $\mu$mol) in 4 M HCl-Ethylacetate (300 $\mu$L) at 0° C. was stirred for 30 minutes before the volatiles were removed by a stream of $N_2$ and the residue was dried under vacuum (0.02 mm) for 15 minutes. The resulting crude 250 was dissolved in dimethylformamide (200 $\mu$L) and treated sequentially with 300 (2.7 mg, 10.6 $\mu$mol, for preparation see Boger et. al., *J. Org. Chem.* 1990, 55,, 4499) and 1-(3-dimethylaminopropyl)-3-ethylcarbodiimide hydrochloride (EDCI) (5.5 mg, 29 $\mu$mol, 3 equiv) and the reaction mixture was stirred for 10 hours at 25° C. Water (0.5 mL) was added to the reaction mixture and the aqueous phase was extracted with Ethylacetate (4×1 mL). The organic layers were combined, dried ($Na_2SO_4$), and concentrated in vacuo. Preparative thin-layer chromatography ($SiO_2$, 20 cm×20 cm×0.25 mm, 5% dimethylformamide-toluene, $R_f$=0.60) afforded 252 (4.1 mg, 4.8 mg theoretical, 85%) as a white solid: $^1$H NMR (dimethylsulfoxide-$d_6$, 400 MHz) μ 11.48 (d, J=2.0 Hz, 1H, NH), 10.35 (s, 1H, OH), 8.02 (d, J=9.2 Hz, 1H, C6-H), 7.74 (br s, 1H, C4-H), 7.12 (d, J=2.4 Hz, 1H, C9-H), 7.08 (d, J=2.0 Hz, 1H, C3'-H), 7.00 (d, J=9.2, 2.4 Hz, 1H, C7-H), 6.98 (s, 1H, C4'-H), 4.72 (t, J=10.5 Hz, 1H, C2-H), 4.47 (dd, J=11.1, 1.3 Hz, 1H, C2-H), 4.19-4.15 (m, 1H, C1-H), 4.05 (dd, J=11.3, 3.3 Hz, 1H, CHHCl), 3.95 (s, 3H, $OCH_3$), 3.93 (s, 3H, $OCH_3$), 3.84 (s, 3H, $OCH_3$), 3.82 (s, 3H, $OCH_3$), 3.80 (dd, J=10.4, 5.5 Hz, 1H, CHHCl), IR (film) $\mu_{max}$ 3238, 2946, 1631, 1585, 1522, 1493, 1463, 1388, 1313, 1220 cm⁻; FABHRMS (NBA) m/e 497.1500 ($M^+$+H, $C_{26}H_{25}ClN_2O_6$ requires 497.1479). Natural (1S)-252: $[\mu]^3$ -23 (c 0.07, dimethylformamide)ent-(1R)-252: $[\mu]^3$ +23 (c 0.10, dimethylformamide).

Preparation of MCBI-TMI (254) as illustrated in
FIG. 6

Compound 254

A solution of 252 (3.5 mg, 7.04 μmol) in tetrahydrofuran-dimethylformamide (3:1, 350 μL) at 0° C. was treated with NaH (0.85 mg, 60% in oil, 21 μmol, 3 equiv). The reaction mixture was stirred for 30 minutes at 0° C. before the addition of pH 7 phosphate buffer (0.2 M, 400 μL) and 3 mL of tetrahydrofuran. The organic solution was dried ($Na_2SO_4$), concentrated in vacuo, and the crude product was purified by preparative thin-layer chromatography ($SiO_2$, 20 cm×20 cm×0.25 mm, 5% dimethylformamide-toluene, $R_f$=0.55) to provide 254 (2.9 mg, 3.2 mg theoretical, 90%) as a white solid: $^1$H NMR (DIMETHYLSULFOXIDE-$d_6$, 400 MHz) μ 11.60 (s, 1H, NH), 7.91 (d, J=8.8 Hz, 1H, C5-H), 7.08 (d, J=2.0 Hz, 1H, C3'-H), 6.97 (dd, J=8.7, 2.4 Hz, 1H, C6-H), 6.92 (s, 1H, C4'-H), 6.70 (d, J=2.4 Hz, 1H, C8-H), 6.60 (s, 1H, C3-H), 4.50 (dd, J=10.5, 5.0 Hz, 1H, C1-H), 4.32 (d, J=10.5 Hz, 1H, C1-H), 3.90 (s, 3H, $OCH_3$), 3.84 (s, 3H, $OCH_3$), 3.80 (s, 3H, $OCH_3$), 3.79 (s, 3H, $OCH_3$), 3.32–3.28 (m, 1H, C9a-H, partially obscured by $H_2O$), 1.78 (dd, J=7.7, 4.0 Hz, 1H, C9-H), 1.69 (t, J=4.3 Hz, 1H, C9-H); IR (film) $\mu_{max}$ 2937, 1646, 1626, 1595, 1533, 1518, 1467, 1446, 1394, 1302, 1270, 1232, 1108 cm⁻¹; FABHRMS (NBA) m/e 461.1732 ($M^+$+H, $C_{26}H_{24}N_2O_6$ requires 461.1713). Natural (+)-254: $[\mu]^3$ -206 (c 0.05, tetrahydrofuran).

Preparation of seco-MCBI-indole₂ (256) as
illustrated in FIG. 6

Compound 256

A solution of 236 (4.3 mg, 11.8 μmol) in 4 M HCl-Ethylacetate (350 μL) at 0° C. was stirred for 30 minutes before the volatiles were removed by a stream of $N_2$ and the residue was dried under vacuum (0.02 mm) for 15 minutes. The resulting crude 250 was dissolved in dimethylformamide (250 μL) and treated sequentially with 58 (4.2 mg, 13.0 μmol, as prepared herein) and 1-(3-DIMETHYLAMINOPROPYL)-3-ETHYL-CARBODIIMIDE HYDROCHLORIDE (EDCI) (6.8 mg, 35 μmol, 3 equiv) and the mixture was stirred for 10 hours at 25° C. Water (0.5 mL) was added to the reaction mixture and the aqueous phase was extracted with Ethylacetate (4×1 mL). The organic layers were combined, dried ($Na_2SO_4$), and concentrated in vacuo. Preparative thin-layer chromatography (20 cm×20 cm×0.25 mm, 15% dimethylformamide-toluene, $R_f$=0.45) afforded 256 (5.2 mg, 6.7 mg theoretical, 78%) as a tan solid: $^1$H NMR (dimethylsulfoxide-$d_6$, 400 MHz) μ 11.72 (s, 2H, NH), 10.32 (s, 1H, OH), 10.16 (s, 1H, NH), 8.22 (s, 1H, C4'-H), 8.02 (d, J=9.2 Hz, 1H, C6-H), 7.82 (br, s, 1H, C4-H), 7.67 (d, J=8.2 Hz, 1H, C4"-H), 7.58 (dd, J=8.9, 1.8 Hz, 1H, C6'-H), 7.49 (d, J=8.4 Hz, 1H, C7"-H), 7.47 (d, J=7.8 Hz, 1H, C7'-H), 7.42 (s, 1H, C3' or C3"-H), 7.23 (s, 1H, C3' or C3"-H), 7.21 (t, J=8.1 Hz, 1H, C6"-H), 7.12 (d, J=2.2 Hz, 1H, C9-H), 7.06 (t, J=7.2 Hz, 1H, C5"-H), 6.98 dd, J=9.2, 2.4 Hz, 1H, C7-H), 4.79 (t, J=10.4 Hz, 1H, C2-H), 4.57 (d, J=10.1 Hz, 1H, C2-H), 4.25–4.21 (m, 1H, C1-H), 4.04 (dd, J=11.0, 3.0 Hz, 1H, CHHCl), 3.86 (dd, J=11.0, 6.3 Hz, 1H, CHHCl), 3.91 (s, 3H, $OCH_3$); IR (film) $\mu_{max}$ 3280, 2920, 1693, 1647, 1630, 1589, 1518, 1455, 1417, 1308, 1220 cm⁻¹; FABHRMS (NBA-CsI) m/e 565.1655 ($M^+$+H, $C_{32}H_{25}ClN_4O_4$ requires 565.1643). Natural (1S)-256: $[\mu]^3$ +54 (c 0.08, dimethylformamide ). ent-(1R)-256: $[\mu]^3$ -55 (c 0.07, dimethylformamide).

Preparation of MCBI-indole₂ (258) as illustrated in
FIG. 6

Compound 258

A solution of 256 (2.8 mg, 4.95 μmol) in tetrahydrofuran-dimethylformamide (3:1, 250 μL) at 0° C. was treated with NaH (0.59 mg, 60% in oil, 15 μmol, 3 equiv) and the mixture was stirred for 30 minutes at 0° C. The reaction mixture was quenched with the addition of pH 7 phosphate buffer (0.2 M, 250 μL) and 3 mL of tetrahydrofuran. The organic solution was dried ($Na_2SO_4$), concentrated in vacuo, and purified by preparative thin-layer chromatography (20 cm×20 cm×0.25 mm, 15% dimethylformamide-toluene, $R_f$=0.40) to provide 258 (2.25 mg, 2.62 mg theoretical, 86%) as a tan solid: $^1$H NMR (dimethylsulfoxide-$d_6$, 400 MHz) μ 11.82 (s, 1H, NH), 11.70 (s, 1H, NH), 10.17 (s, 1H, NH), 8.21 (s, 1H, C4'-H), 7.94 (d, J=8.7 Hz, 1H, C5-H), 7.66 (d, J=8.0 Hz, 1H, C4"-H), 7.59 (dd, J=8.8, 1.7 Hz, 1H, C6'-H), 7.47 (apparent d, J=9.2 Hz, 2H, C7'-H and C7"-H), 7.41 (s, 1H, C3'-H or Cb 3"-H), 7.27 (d, J=1.6 Hz, 1H, C3' or C3"-H), 7.21 (t, J=7.2 Hz, 1H, C6"-H), 7.06 ((t, J=7.2 Hz, 1H, C5"-H), 6.98 (dd, J=8.7, 2.3 Hz, 1H, C6'-H), 6.89 (s, 1H, C3-H), 6.72 (d, J=2.3 Hz, 1H, C8-H), 4.62 (dd, J=10.3, 5.0 Hz, 1H, C1-H), 4.49 (d, J=10.3 Hz, 1H, C1-H), 3.92-3.87 (m, 1H, C9a-H), 3.85 (s, 3H, $OCH_3$), 1.77 (dd, J=7.7, 4.0 Hz, 1H, C9-H), 1.67 (d, J=4.0 Hz, 1H, C9-H); IR (film) $\mu_{max}$ 2944, 1647, 1586, 1550, 1517, 1391, 1234, 1137, 1067, 1025 cm⁻¹; FABHRMS (NBA) m/e 529.1889 ($M^+$+H, $C_{32}H_{24}N_4O_4$ requires 529.1876). Natural (+)-258: $[\mu]^3$+122 (c 0.04, dimethylformamide) ent-(-)-258: $[\mu]^3$ -120 (c 0.07, dimethylformamide).

Preparation of seco-MCBI-CDPI₁ (260) as
illustrated in FIG. 6

Compound 260

A solution of 236 (3.9 mg, 10.7 μmol) in 4 M HCl-Ethylacetate (300 μL) at 0° C. was stirred for 30 minutes before the volatiles were removed by a stream of $N_2$ and the residue was dried under vacuum (0.02 mm) for 15 in. The resulting crude 250 was dissolved in dimethylformamide (200 μL) and treated sequentially with 320 (2.9 mg, 11.8 μmol, as prepared in Boger et. al *J. Org. Chem.,* 1987,52, 1521) and 1-(3-DIMETHYLAMINOPROPYL)-3-ETHYLCARBODIIMIDE HYDROCHLORIDE (EDCI)

(6.1 mg, 32 μmol, 3 equiv) and the mixture was stirred at 25° C. for 12 hours. Water (0.5 mL) was added to the reaction mixture and the aqueous phase was extracted with Ethylacetate (4×1 mL). The organic layers were combined, dried ($Na_2SO_4$), and concentrated in vacuo. Preparative thin-layer chromatography (20 cm×20 cm×0.25 mm, 30% dimethylformamide-toluene, $R_f$=0.65) afforded 260 (3.7 mg, 5.2 mg theoretical, 71%) as a light yellow solid: $^1$H NMR (DIMETHYLSULFOXIDE-$d_6$, 400 MHz) μ11.60 (d, J=2.0 Hz, 1H, NH), 10.31 (s, 1H, OH), 8.01 (d, J=9.2 Hz, 1H, C6-H), 7.99 (d, J=8.9 Hz, 1H, C4'-H), 7.80 (br s, 1H, C4-H, 7.23 (d, J=8.9 Hz, 1H, C5'-H), 7.10 (d, J=2.4 Hz, 1H, C9-H), 7.00 (d, J=1.5 Hz, 1H, C8'-H), 6.98 (dd, J=9.2, 2.4 Hz, 1H, C7'-H), 6.10 (br s, 2H, $NH_2$), 4.77 (t, J=10.8 Hz, 1H, C2-H), 4.54 (dd, J=11.0, 1.4 Hz, 1H, C2-H), 4.22-4.17 (m, 1H, C1-H), 4.04 (dd, J=11.1, 3.1 Hz, 1H, CHHCl), 3.98 (t, J=8.8 Hz, 2H, C2'-$H_2$), 3.92 (s, 3H, $OCH_3$), 3.86 (dd, J=11.1, 7.2 Hz, 1H, CHHCl), 3.25 (t, J=8.8 Hz, 2H, C1'-$H_2$ partially obscured by $H_2O$); IR (film) $\mu_{max}$ 3292, 2923, 1659, 1630, 1595, 1504, 1446, 1415, 1384, 1224 cm$^{-1}$; FABHRMS (NBA) m/e 490.1411 ($M^+$, $C_{26}H_{23}ClN_4O_4$ requires 490.1408). Natural (1S)-260: $[\mu]^3$ +74 (c 0.09, dimethylformamide) ent-(1R)-260: $[\mu]^3$ −76 (c 0.11, dimethylformamide).

Preparation of MCBI-$CDPI_1$ (262) as illustrated in FIG. 6

Compound 262

A solution of 260 (1.8 mg, 3.67 μmol) in tetrahydrofuran-dimethylformamide (3:1, 200 μL) at 0° C. was treated with NaH (0.44 mg, 60% in oil, 11 μmol, 3 equiv). The mixture was stirred at 0° C. for 30 minutes before the reaction was quenched with the addition of pH 7 phosphate buffer (0.2 M, 200 μL) and 3 mL of tetrahydrofuran. The organic solution was dried ($Na_2SO_4$), concentrated in vacuo, and purified by preparative thin-layer chromatography) 20 cm×20 cm×0.25 mm, 30% dimethylformamide-toluene, $R_f$=0.65) to provide 262 (1.50 mg, 1.67 mg theoretical, 90%) as a light yellow solid: $^1$H NMR (DIMETHYLSULFOXIDE-$d_6$, 400 MHz) μ 11.70 (s, 1H, NH), 8.01 (d, J=9.2 Hz, 1H, C4'-H), 7.93 (d, J=8.4 Hz, 1H, C5-H), 7.21 (d, J=8.8 Hz, 1H, C5'-H), 7.06 (s, 1H, C8'-H), 6.98 (dd, J=8.6, 2.2 Hz, 1H, C6-H), 6.86 (s, 1H, C3-H), 6.71 (d, J=2.2 Hz, 1H, C8-H), 6.11 (br s, 2H, $NH_2$), 4.58 (dd, J=10.3, 4.9 Hz, 1H, C1-H), 4.46 (d, J=10.3 Hz, 1H, C1-H), 3.97 (t, J=8.5 Hz, 2H, C2'-$H_2$), 3.85 (s, 3H, $OCH_3$), 3.38-3.30 (m, 3H, C9a, C1'-$H_2$ partially obscured by $H_2O$), 1.77 (dd, J=7.8, 4.1 Hz, 1H, C9-H), 1.66 (t, J=4.1 Hz, 1H, C9-H); IR (film) $\mu_{max}$ 3375, 2937, 1652, 1597, 1572, 1501, 1455, 1426, 1388, 1359, 1334, 1300, 1267, 1229, cm$^{-1}$; FABHRMS (NBA) m/e 455.1730 ($M^+$+H, $C_{26}H_{22}N_4O_4$ requires 455.1719). Natural (+)-262 $[\mu]^3$ +183 (c 0.07, dimethylformamide) ent-(−)-262: $[\mu]^3$ −187 (c 0.08, dimethylformamide).

Preparation of seco-MCBI-$CDPI_2$ (264) as illustrated in FIG. 6

Compound 264

A solution of 236 (3.6 mg, 9.8 μmol) in 4 M HCl-Ethylacetate (300 μL) at 0° C. was stirred for 30 minutes before the volatiles were removed by a stream of $N_2$ and the residue was dried under vacuum (0.02 mm) for 15 minutes. The resulting crude 250 was dissolved in dimethylformamide (200 μL) and treated sequentially with 340 (4.6 mg, 10.7 μmol as prepared in Boger et. al., *J. Org. Chem.*, 1984, 49, 2240) and 1-(3-dimethylaminopropyl)-3-ethylcarbodiimide hydrochloride (EDCI) (5.6 mg, 29 μmol, 3 equiv) and the mixture was stirred by 6 hours at 25° C. The solvent was removed under vacuum, water (0.5 mL) was added to the mixture, and the insoluble crude product was collected by centrifugation. Preparative thin-layer chromatography (20 cm×20 cm×0.25 mm, 33% dimethylformamide-toluene, $R_f$=0.50) afforded 264 (4.5 mg, 6.6 mg theoretical, 68%) as a light yellow solid: $^1$H NMR (DIMETHYLSULFOXIDE-$d_6$, 400 MHz) μ 11.80 (d, J=1.6 Hz, 1H, NH), 11.55 (d, J=1.2 Hz, 1H, NH), 10.31 (s, 1H, OH), 8.28 (d, J=7.0 Hz, 1H, C4'-H), 8.01 (d, J=9.2 Hz, 1H, C6-H), 7.97 (d, J=8.9 Hz, 1H, C4"-H), 7.82 (br s, 1H, C4-H), 7.38 (d, J=9.0 Hz, 1H, C5"-H), 7.22 (d, J=8.8 Hz, 1H, C5'-H), 7.16 (d, J=1.3 Hz, 1H, C8"-H), 7.12 (d, J=2.3 Hz, 1H, C9-H), 6.98 (dd, J=9.2, 2.4 Hz, 1H, C7-H), 6.97 (s, 1H, C8'-H), 6.10 (br s, 2H, $NH_2$), 4.80 (t, J=10.8 Hz, 1H, C2-H), 4.66 (t, J=8.3 Hz, 2H, C2'-$H_2$), 4.57 (d, J=11.0 Hz, 1H, C2-H), 4.23-4.21 (m, 1H, C1-H), 4.05 (dd, J=11.0, 3.0 Hz, 1H, CHHCl), 3.96 (t, J=8.8 Hz, 2H, C2"-$H_2$), 3.91 (s, 3H, $OCH_3$), 3.87 (dd, J=11.0, 4.2 Hz, 1H, CHHCl), 3.52-3.35 (m, 4H, C1'-$H_2$, C1"-$H_2$ partially obscured by $H_2O$); IR (film) $\mu_{max}$ 3374, 2913, 2851, 1662, 1651, 1605, 1446, 1425, 1359, 1282, 1241, 1164 cm$^{-1}$; FABHRMS (NBA) m/e 675.2143 ($M^+$+H, $C_{37}H_{31}ClN_6O_5$ requires 675.2123). Natural (1S)-264: $[\mu]^3$ +50 (c 0.05 dimethylformamide) ent-(1R)-264: $[\mu]^3$ −52 (c 0.04, dimethylformamide).

Preparation of MCBI-$CDPI_2$ (266) as illustrated in FIG. 6

Compound 266

A solution of 264 (0.57 mg, 0.84 μmol) in tetrahydrofuran-dimethylformamide (3:1 50 μL) at 0° C. was treated with NaH (0.10 mg, 2.5 μmol, 3 equiv) and the mixture was stirred at 0° C. for 30 minutes. The reaction mixture was quenched with the addition of pH 7 phosphate buffer (0.2 M,, 50 μL) and 2 mL of tetrahydrofuran. The organic solution was dried ($Na_2SO_4$), concentrated in vacuo, and purified by preparative thin-layer chromatography (5 cm ×20 cm×0.25 mm, 33% dimethylformamide-toluene, $R_f$=0.45) to provide 266 (0.51 mg, 0.54 mg theoretical, 94%) as a light yellow solid: $^1$H NMR (DIMETHYLSULFOXIDE-$d_6$, 400 MHz) μ 11.90 (d, J=2.0 Hz, 1H, NH), 11.55 (d, J=2.0 Hz, 1H, NH), 8.29 (d, J=8.1 Hz, 1H, C4'-H), 7.97 (d, J=8.9 Hz, 1H, C4"-H), 7.93 (d, J=8.8 Hz, 1H, C5-H), 7.36 (d, J=8.9 Hz, 1H, C5"-H), 7.22 (d, J=1.7 Hz, 1H, C8"-H), 7.21 (d, J=8.7 Hz, 1H, C5"-H), 6.98 (dd, J=8.8, 2.4 Hz, 1H, C7-H), 6.96 (d, J=1.3 Hz, 1H, C8'-H), 6.88 (s, 1H, C3-H), 6.73 (d, J=2.4 Hz, 1H, C8-H), 6.10 (br s, 2H, $NH_2$), 4.65 (t, J=8.2 Hz, 2H, C2'-$H_2$), 4.61 (dd, J=10.5, 4.8 Hz, 1H, C1-H), 4.50 (d, J=10.5 Hz, 1H, C1-H), 3.98 (t, J=8.7 Hz, 2H, C2"-$H_2$), 3.86 (s, 3H, $OCH_3$), 3.50-3.35 (m, 5H, C1'-$H_2$, C1"-$H_2$, C9a-H partially obscured by $H_2O$), 1.78 (dd, J=7.8, 4.0 Hz, 1H, C9-H), 1.68 (t, J=4.3 Hz, 1H, C9-H); IR (film) $\mu_{max}$ 3372, 2920, 1656, 1602, 1581, 1501, 1430, 1392, 1363, 1338, 1267, 1229, 1141, 1019 cm$^{-1}$; FABHRMS (NBA-CsI) m/e 771.1244 ($M^+$+Cs, $C_{37}H_{30}N_6O_5$ requires 771.1332). Natural (+)-266: $[\mu]^3$ +145 (c 0.01, dimethylformamide)ent-(−)-266: $[\mu]^3$ −149 (c 0.01, dimethylformamide).

Solvolysis Reactivity

N-BOC-MCBI (238, 0.1 mg) was dissolved in $CH_3OH$ (1.5 mL) and mixed with pH 3 aqueous buffer (1.5 mL). The buffer contained 4:1:20 (v:v:v) 0.1 M citric acid, 0.2 M $Na_2HPO_4$, and $H_2O$, respectively. The solvolysis solution was sealed and kept at 25° C. protected from light. The UV spectrum was measured at regular intervals every 2 hours during the first day, every 12 hours for another week, and every 24 hours for an additional week. The decrease in the long-wavelength absorption at 324 nm and the increase in the short-wavelength absorption at 266 nm were monitored, FIG. 1. The solvolysis rate constant (k=2.41×10⁻⁶ s⁻¹) and half-life ($t_{1/2}$=80 hours) were calculated from data recorded at the short wavelength from the least squares treatment (r=0.995) of the slope of the plot of time versus 1−[(A−$A_i$)/ $A_f$−$A_i$)].

Similarly, MCBI (240, 0.1 mg) was dissolved in $CH_3OH$ (1.5 mL) and mixed with pH aqueous buffer (1.5 mL). The solvolysis solution was sealed and stirred at 25° C. in the dark. The UV spectrum was recorded every 24 hours for two months. The decrease in the long-wavelength absorption at 340 nm and the increase in absorption at 268 nm were monitored, FIG. 1. The solvolysis rate constant (k=5.76× 10⁻⁷ s⁻¹) and half-life ($t_{1/2}$=334 hours) were determined as detailed above (r=0.98).

Solvolysis Regioselectivity 3-(tert-Butyloxycarbonyl)-5-hydroxy-8-methoxy-1-methoxymethyl-1,2-dihydro-3H-benz[e]indole (268) as illustrated in FIG. 7

Compound 268

A solution of 238 (10.1 mg, 30.8 μmol) in 2.5 mL of $CH_3OH$ was cooled to 0° C. and $CF_3SO_3H$—$CH_3OH$ (185 μL, 0.02 M, 0.12 equiv) was added. After 3 hours, the reaction was quenched by the addition of $NaHCO_3$ (10 mg) and the mixture was warmed to 25° C., filtered, and the solution was concentrated. Centrifugal thin-layer chromatography ($SiO_2$, 0.3 mm chromatotron plate, 30% Ethylacetate-hexane) provided 268 (10.5 mg, 11.1 mg theoretical, 95%) as a white solid: mp 157–159° C. (hexane, white prisms); $^1$H NMR ($C_6D_6$, 400 MHz) $\mu$ 8.46 (d, J=8.3 Hz, 1H, C6-H), 8.15 (br s, 1H, C4-H), 7.06 (dd, J=9.2, 2.4 Hz, 1H, C7-H), 6.99 (d, J=2.4 Hz, 1H, C9H), 6.95 (br, s, 1H, OH), 4.22 (d, J=10.6 Hz, 1H, C2-H), 3.85-3.80 (m, 1H, C2-H), 3.66-3.63 (m, 1H, $CHHOCH_3$), 3.55 (dd, J=9.2, 3.7 Hz, 1H, $CHHOCH_3$), 3.41 (s, 3H, $OCH_3$) 3.01-2.95 (m, 1H, C1-H), 2.97 (s, 3H, $OCH_3$), 1.44 (s, 9H, $C(CH_3)_3$); $^{13}$C NMR ($C_6D_6$, 100 MHz) $\mu$ 159.4, 154.5, 153.4, 142.4, 132.9, 125.9, 117.5 115.1, 114.4, 102.0, 98.0, 80.8, 74.7, 58.5, 54.7, 53.3, 37.8, 28.4; IR (film) $\mu_{max}$ 3329, 2974, 2932, 1697, 1674, 1629, 1590, 1476, 1418, 1368, 1331, 1224, 1141, 1028 cm⁻¹; FABHRMS (NBA-NaI) m/e 359.1720 (M³⁰, $C_{20}H_{25}NO_5$ requires 359.1733).

Anomalous Relative Rates of DNA Alkylation

Figure 18:
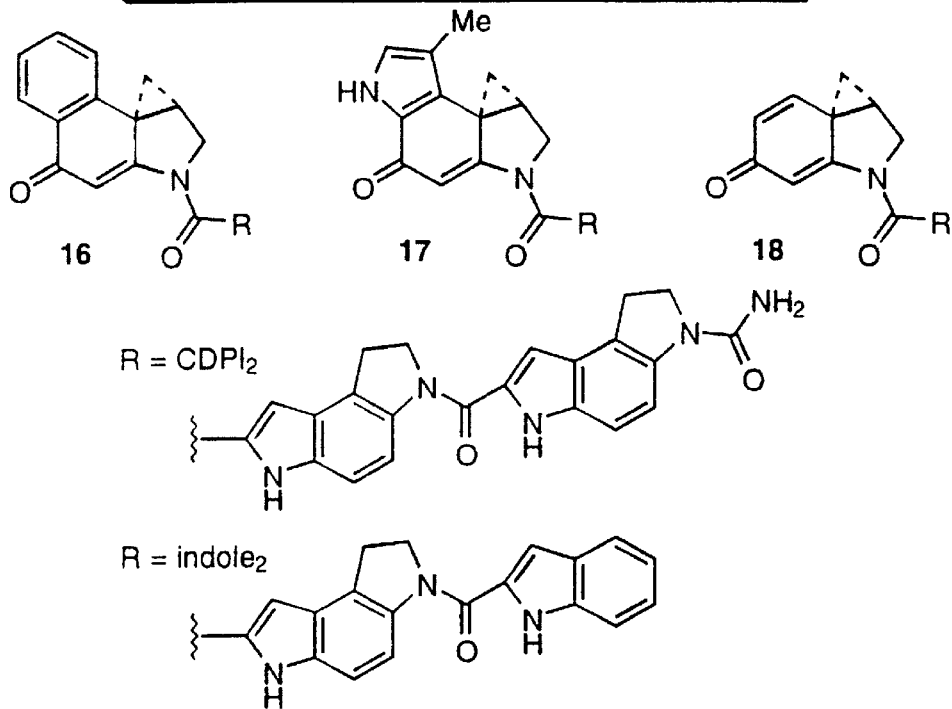
FIG. 18 illustrates that the relative rates of DNA alkylation, for the various agents, do not follow the relative rates of acid-catalyzed solvolysis (k=respective rate constant).
Figure 18:
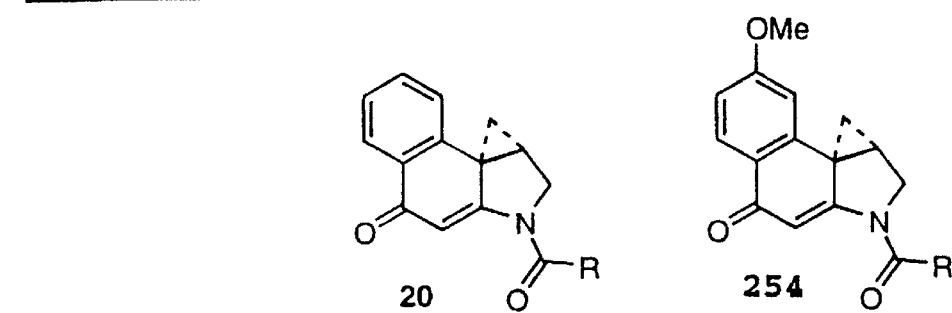

It has been observed that the relative rates of DNA alkylation do not follow the relative rates of acid-catalyzed solvolysis (FIG. 18). Although this was first disclosed with a series of agents (16–18) that possessed sufficiently different structures that the origin of the effects was unclear, the latter series (20 and 254) are so closely related that the subtle structural differences are unlikely to be contributing to an alteration of the expected order of reactivity. Rather, the unexpected order of DNA alkylation rates observed with the latter agents may be influenced by a previously unrecognized effect intimately linked to catalysis. In this latter series, the impact of the C7 substituent (20 and 254, R=$OCH_3$>H) is related to its simple presence rather than its electronic nature (R=$OCH_3$>H). We now suggest this impact is due to the extended length of the alkylation subunit and the corresponding increase in the inherent twist of the linking N2 amide that would accompany DNA minor groove binding thus providing a nonobvious role for the methoxy group.

What is claimed:
1. A compound represented by the following structure:

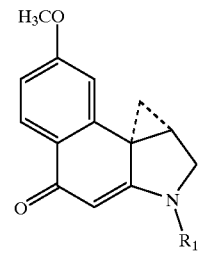

wherein:

$R_1$ is selected from the group consisting of hydrogen, tert-butoxycarbonyl and a radical represented by the following structure:

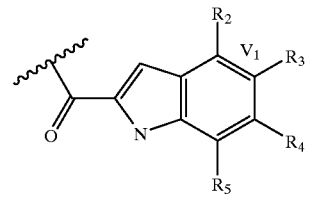

$R_2$ is selected from the group consisting of hydrogen, hydroxyl, O-alkyl (C1–C6), and a first N-substituted pyrrolidine ring;

$R_3$ is selected from the group consisting of hydrogen, hydroxyl, O-alkyl (C1–C6), the first N-substituted pyrrolidine ring and a radical represented by the following structure:

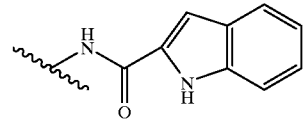

$R_4$ is selected from the group consisting of hydrogen, hydroxyl and O-alkyl (C1–C6); and $R_5$ is selected from the group consisting of hydrogen, hydroxyl and O-alkyl (C1–C6); and $V_1$ represents a first vinylene group between $R_2$ and $R_3$; with the following provisos:
  if $R_2$ participates in the first N-substituted pyrrolidine ring, the $R_3$ also participates in the first N-substituted pyrrolidine ring;
  if $R_3$ participates in the first N-substituted pyrrolidine ring, the $R_2$ also participates in the first N-substituted pyrrolidine ring;
  if $R_2$ and $R_3$ participate in the first N-substituted pyrrolidine ring, the $R_4$ and $R_5$ are hydrogen;
  if $R_2$ is hydrogen, then $R_4$ and $R_5$ are hydrogen and $R_3$ is a radical represented by the following structure:

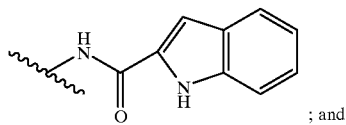 ; and wherein the first N-substituted pyrrolidine ring is fused to the first vinylene group between $R_2$ and $R_3$ and is represented by the following structure:

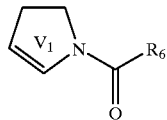

wherein $V_1$ represents the first vinylene group between $R_2$ and $R_3$; and $R_6$ is selected from the group consisting of —$NH_2$ and a radical represented by the following structure:

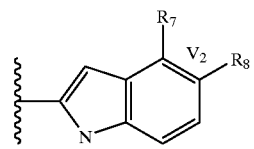

wherein:

$R_7$ is selected from the group consisting of hydrogen, hydroxyl, O-alkyl (C1–C6), and a second N-substituted pyrrolidine ring;

$R_8$ is selected from the group consisting of hydrogen, hydroxyl, O-alkyl (C1–C6), and the second N-substituted pyrrolidine ring;

$V_2$ represents the second vinylene group between $R_7$ and $R_8$;

with the following provisos:

if $R_7$ participates in the N-substituted pyrrolidine ring, then $R_8$ also participates in the N-substituted pyrrolidine ring;

if $R_8$ participates in the N-substituted pyrrolidine ring only if $R_7$ also participates in the N-substituted pyrrolidine ring; and wherein the second N-substituted pyrrolidine ring is fused to the second vinylene group between $R_7$ and $R_8$ and is represented by the following structure:

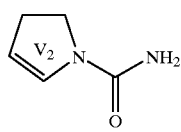

wherein:

$V_2$ represents the second vinylene group between $R_7$ and $R_8$.

2. A compound as described in claim 1 represented by the following structure:

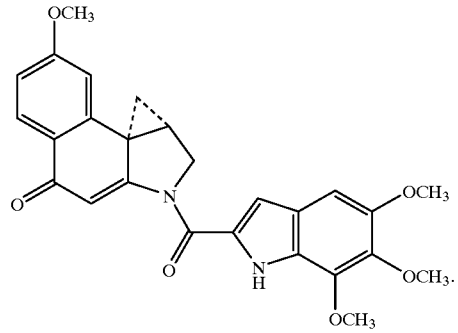

3. A compound as described in claim 1 represented by the following structure:

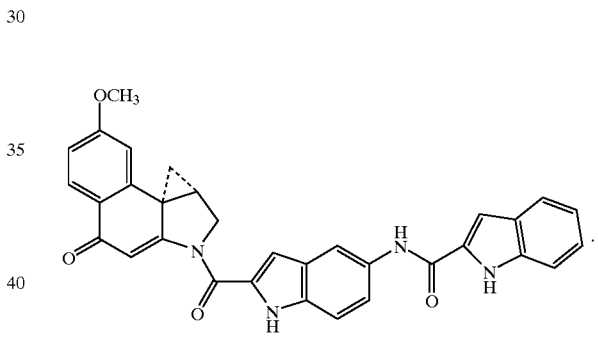

4. A compound as described in claim 1 represented by the following structure:

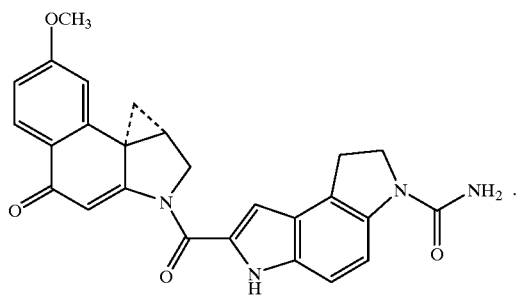

5. A compound as described in claim 1 represented by the following structure:

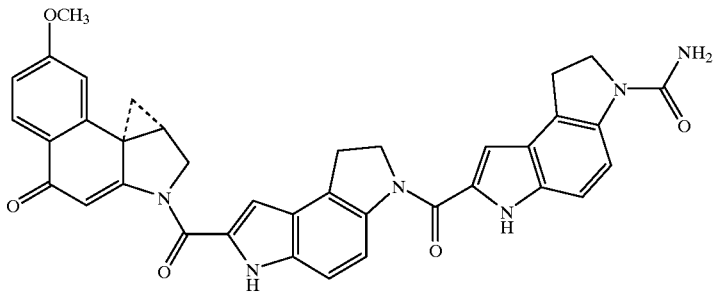

6. A compound represented by the following structure:

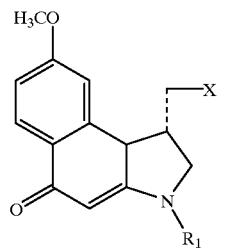

wherein:
X is selected from the group consisting of chlorine, bromine, iodine, and OTOS; and
$R_1$ is selected from the group consisting of hydrogen, tert-butoxycarbonyl and a radical represented by the following structure:

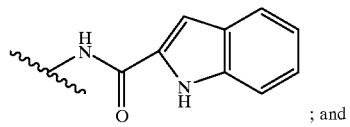

$R_2$ is selected from the group consisting of hydrogen, hydroxyl, O-alkyl (C1–C6), and a first N-substituted pyrrolidine ring;
$R_3$ is selected from the group consisting of hydrogen, hydroxyl, O-alkyl (C1–C6), the first N-substituted pyrrolidine ring and a radical represented by the following structure:

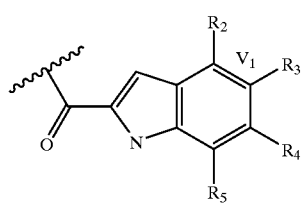

$R_4$ is selected from the group consisting of hydrogen, hydroxyl and O-alkyl (C1–C6); and
$R_5$ is selected from the group consisting of hydrogen, hydroxyl and O-alkyl (C1–C6); and
$V_1$ represents a first vinylene group between $R_2$ and $R_3$;
with the following provisos:
if $R_2$ participates in the first N-substituted pyrrolidine ring, the $R_3$ also participates in the first N-substituted pyrrolidine ring;
if $R_3$ participates in the first N-substituted pyrrolidine ring, the $R_2$ also participates in the first N-substituted pyrrolidine ring;
if $R_2$ and $R_3$ participate in the first N-substituted pyrrolidine ring, the $R_4$ and $R_5$ are hydrogen;
if $R_2$ is hydrogen, then $R_4$ and $R_5$ are hydrogen and $R_3$ is a radical represented by the following structure:

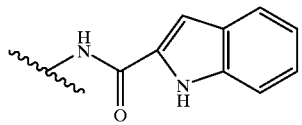
; and wherein the first N-substituted pyrrolidine ring is fused to the first vinylene group between $R_2$ and $R_3$ and is represented by the following structure:

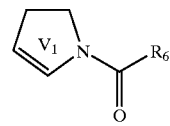

wherein
$V_1$ represents the first vinylene group between $R_2$ and $R_3$; and
$R_6$ is selected from the group consisting of —$NH_2$ and a radical represented by the following structure:

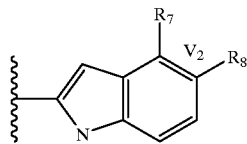

wherein:
$R_7$ is selected from the group consisting of hydrogen, hydroxyl, O-alkyl (C1–C6), and a second N-substituted pyrrolidine ring;
$R_8$ is selected from the group consisting of hydrogen, hydroxyl, O-alkyl (C1–C6), and the second N-substituted pyrrolidine ring;
$V_2$ represents the second vinylene group between $R_7$ and $R_8$;
with the following provisos:
if $R_7$ participates in the N-substituted pyrrolidine ring, then $R_8$ also participates in the N-substituted pyrrolidine ring;
if $R_8$ participates in the N-substituted pyrrolidine ring only if $R_7$ also participates in the N-substituted pyrrolidine ring; and wherein the second N-substituted pyrrolidine ring is fused to the second vinylene group between $R_7$ and $R_8$ and is represented by the following structure:

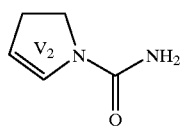

wherein:

$V_2$ represents the second vinylene group between $R_7$ and $R_8$.

7. A compound as described in claim 6 represented by the following structure:

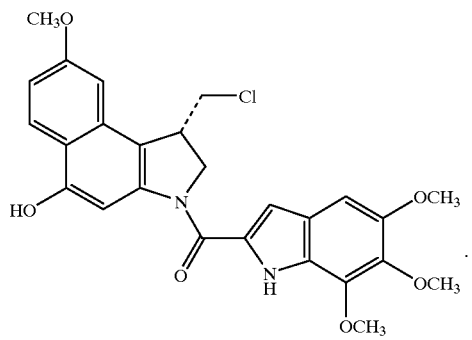

8. A compound as described in claim 6 represented by the following structure:

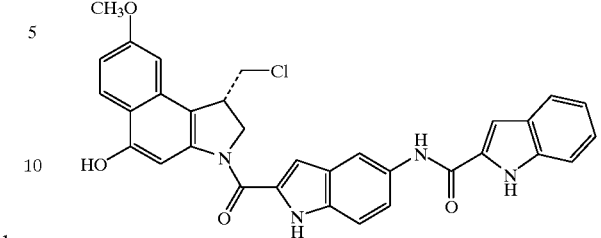

9. A compound as described in claim 6 represented by the following structure:

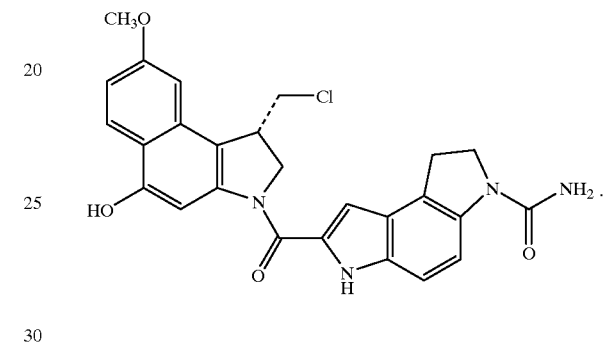

10. A compound as described in claim 6 represented by the following structure:

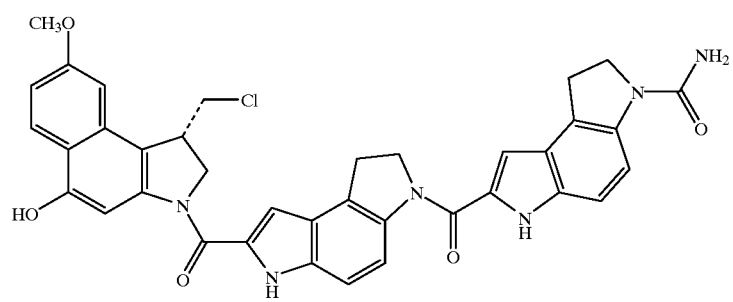

11. A method for alkylating DNA employing a step wherein the compounds of claims 1 or 6 are contacted with DNA under alkylating conditions.

* * * * *